(12) United States Patent
Denkinger et al.

(10) Patent No.: US 11,730,812 B2
(45) Date of Patent: Aug. 22, 2023

(54) ANTI-IL-36R ANTIBODY FORMULATIONS

(71) Applicant: Boehringer Ingelheim International GmbH, Ingelheim am Rhein (DE)

(72) Inventors: Sandra Nicole Denkinger, Biberach an der Riss (DE); Anna Maria Steiner, Eberhardzell (DE); Derrick Spencer Katayama, Timnath, CO (US); Rajni Prasad Mehra, Pleasanton, CA (US); Ingo Michael Presser, Biberach an der Riss (DE); Ravija Singh, Fremont, CA (US); Sara Kay Wright, Castro Valley, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/809,606

(22) Filed: Mar. 5, 2020

(65) Prior Publication Data

US 2020/0282053 A1    Sep. 10, 2020

Related U.S. Application Data

(60) Provisional application No. 62/815,405, filed on Mar. 8, 2019.

(51) Int. Cl.
| | |
|---|---|
| *A61K 39/395* | (2006.01) |
| *A61K 9/00* | (2006.01) |
| *A61K 9/19* | (2006.01) |
| *C07K 16/24* | (2006.01) |
| *A61K 47/18* | (2017.01) |
| *A61K 47/26* | (2006.01) |
| *A61K 47/34* | (2017.01) |
| *A61K 47/14* | (2017.01) |

(52) U.S. Cl.
CPC ...... *A61K 39/39591* (2013.01); *A61K 9/0019* (2013.01); *A61K 9/19* (2013.01); *A61K 47/183* (2013.01); *A61K 47/26* (2013.01); *C07K 16/244* (2013.01); *A61K 47/14* (2013.01); *A61K 47/34* (2013.01); *C07K 2317/565* (2013.01)

(58) Field of Classification Search
None
See application file for complete search history.

(56) References Cited

U.S. PATENT DOCUMENTS

| | | |
|---|---|---|
| 5,595,756 A | 1/1997 | Bally et al. |
| 6,416,973 B1 | 7/2002 | Bakker et al. |
| 6,953,843 B2 | 10/2005 | Bakker et al. |
| 7,332,574 B2 | 2/2008 | Bakker et al. |
| 8,034,771 B2 | 10/2011 | Sims et al. |
| 8,481,021 B2 | 7/2013 | Sims et al. |
| 9,023,995 B2 * | 5/2015 | Brown ............ C07K 16/2866 530/387.1 |
| 2004/0110930 A1 | 6/2004 | Reinl et al. |
| 2004/0132085 A1 | 7/2004 | Bakker et al. |
| 2004/0177391 A1 | 9/2004 | Bakker et al. |
| 2005/0084900 A1 | 4/2005 | Bakker et al. |
| 2007/0041905 A1 | 2/2007 | Hoffman et al. |
| 2007/0071675 A1 | 3/2007 | Wu et al. |
| 2008/0171035 A1 | 7/2008 | Bakker et al. |
| 2008/0292623 A1 | 11/2008 | Bakker et al. |
| 2009/0263403 A1 | 10/2009 | Bakker et al. |
| 2010/0129374 A1 | 5/2010 | Bakker et al. |
| 2010/0150945 A1 | 6/2010 | Bigler et al. |
| 2010/0221252 A1 | 9/2010 | Bigler et al. |
| 2011/0110852 A1 | 5/2011 | Miller et al. |
| 2011/0159011 A1 | 6/2011 | Carrier et al. |
| 2012/0177647 A1 | 7/2012 | Bigler et al. |
| 2012/0244158 A1 * | 9/2012 | Brige ............ A61K 39/39591 424/135.1 |
| 2013/0186797 A1 * | 7/2013 | Walsh ............ A61K 9/0019 206/459.5 |
| 2013/0236471 A1 | 9/2013 | Brown et al. |
| 2018/0273627 A1 | 9/2018 | Boecher et al. |
| 2019/0284273 A1 | 9/2019 | Boecher et al. |

FOREIGN PATENT DOCUMENTS

| | | |
|---|---|---|
| EP | 1003861 A2 | 5/2000 |
| EP | 2152750 A1 | 2/2010 |
| EP | 2176294 A1 | 4/2010 |
| EP | 2337799 A2 | 6/2011 |
| WO | 9906557 A2 | 2/1999 |
| WO | 2008033333 A2 | 3/2008 |
| WO | 2008133857 A1 | 11/2008 |
| WO | 2009006112 A1 | 1/2009 |
| WO | 2010025369 A2 | 3/2010 |
| WO | 2013074569 A1 | 5/2013 |
| WO | 2016168542 A1 | 10/2016 |
| WO | 2019177883 A2 | 9/2019 |
| WO | 2019177888 A1 | 9/2019 |
| WO | 2020136101 A1 | 7/2020 |
| WO | 2020185479 A1 | 9/2020 |

OTHER PUBLICATIONS

Vajdos et al. (J Mol Biol. Jul. 5, 2002;320(2):415-28) (Year: 2002).*
Brown et al. (J Immunol. May 1996;156(9):3285-91) (Year: 1996).*
Chang, B.S. and Hershenson, S. 2002. Practical approaches to protein formulation development in "Rationale Design of stable protein formulations-theory and practice" (J.F. Carpenter and M.C. Manning eds.) Kluwer Academic/Plenum publishers, New York. pp. 1-25. (Year: 2002).*
International Search Report PCT/US2020/021059 dated Jun. 23, 2020.
Anonymous Anti-IL36 gamma/IL—1 F9 antibody (OT12F4) (ab156783), Jan. 1, 2019, XP055650144, 6 pgs.

(Continued)

*Primary Examiner* — Brian Gangle
*Assistant Examiner* — Andrea K McCollum
(74) *Attorney, Agent, or Firm* — Wendy M. Gombert

(57) ABSTRACT

The present invention relates to anti-interleukin-36 receptor (anti-IL-36R1) antibody formulations for administration to a subject.

40 Claims, 10 Drawing Sheets

Specification includes a Sequence Listing.

(56) References Cited

OTHER PUBLICATIONS

Su, Zhi et al. "IL-36 receptor antagonistic antibodies inhibit inflammatory responses in preclinical models of psoriasiform dermatitis" (2019) Experimental Dermatology, 28, 113-120.
Tortola, Luigi et al. "Psoriasiform dermatitis is driven by IL-36-mediated DC-keratinocyte crosstalk" The Journal of Clinical Investigation (2012) vol. 122, No. 11, pp. 3965-3976.
Towne, Jennifer E. et al. "Interieukin (IL)-1F6, IL-1F8, and IL-1F9 Signal through IL-1Rrp2 and IL-1RAcP to Activate the Pathway Leading to NF-kB and MAPKs*" The Journal of Biological Chemistry (2004) vol. 279, No. 14, pp. 13677-13688.
Towne, Jennifer E. et al. "Interleukin-36 (IL-36) Ligands Require Processing for Full Agonist (IL-36a, IL-36b, and IL-36g) or Antagonist (IL-36Ra) Activity" The Journal of Biological Chemistry (2011) vol. 286, No. 49, pp. 42594-42602.
Tsai, Ya-Chu et al. "Anti-interleukin and interieukin therapies for psoriasis: current evidence and clinical usefulness" (2017) Therapeutic Advances in Musculoskeletal Disease, vol. 9 (11), 277-294.
Vajdos et al., "Comprehensive Functional Maps of the Antigenbinding Site of an Anti-Erb82 Antibody Obtained with Shotgun Scanning Mutagenesis", J. Mol. Biol., 2002, 320, pp. 415-428.
Wang, Wei et al. "Antibody Structure, Instability and Formulation" (2007) Journal of Pharmaceutical Sciences, vol. 96, No. 1, 1-26.
Warzocha, Krzysztof et al. "Antisense Strategy: Biological Utility and Prospects in the Treatment of Hematological Malignancies" (1997) Leukemia and Lymphoma, vol. 24, 267-281.
Wong, Chi Heem et al. "Estimation of clinical trial success rates and related parameters" (2019) Biostatistics, 20, 2, 273-286.
Aagaard, Lars et al. "RNAi therapeutics: Principles, prospects and challenges" (2007) Advanced Drug Delivery Reviews, vol. 59, 75-86.
Andoh, Akira et al. "Increased Expression of Interleukin-36 in the Inflamed Mucosa of Inflammatory Bowel Disease" Abstract 1812, (2015) The American Journal of Gastroenterology, vol. 110, Supplement 1, S770.
Arend, William P. et al. "IL-1, IL-18, and IL-33 families of cytokines" Immunological Reviews (2008) vol. 223, pp. 20-22.
Blumberg, Hal et al. "IL-1RL2 and Its Ligands Contribute to the Cytokine Network in Psoriasis" The Journal of Immunology (2010) vol. 185, pp. 4354-4362.
Blumberg, Hal et al. "Opposing activities of two novel members of the IL-1 ligand family regulate skin inflammation" The Journal of Experimental Medicine (2007) vol. 204, No. 11, pp. 2603-2614.
Body Mass Index Table from www.nhlbi.nih.gov/health/educational/lose_wt/BMI/bmi_tbl.pdf <http://www.nhlbi.nih.gov/health/educational/lose_wt/BMI/bmi_tbl.pdf>, viewed Sep. 16, 2021.
Born, Teresa et al. "Identification and characterization of two members of a novel class of the interleukin-1 receptor (IL-1R) family. Delineation of a new class of IL-1R-related proteins based on signaling" The Journal of Biological Chemistry (2000), vol. 275, pp. 29946-29954.
Bowie, James U. et al. "Deciphering the Message in Protein Sequences: Tolerance to Amino Acid Substitutions" Science (1990) vol. 247, pp. 1306-1310.
Brown et al., "Tolerance to Single, but Not Multiple, Amino Acid Replacements in Antibody VH CDR2", J. Immunol., 1996, 156, pp. 3285-3291.
Burgess, Wilson H. et al. "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue" Journal of Cell Biology, (1990) vol. 111, pp. 2129-2138.
Chustz, Regina T. et al. "Regulation and Function of the IL-1 Family Cytokine IL-1F9 in Human Bronchial Epithelial Cells" Am J Respir Cell Mol Biol (2011) vol. 45, pp. 145-153.
Clark, James D. et al. "Discovery and Development of Janus Kinase (JAK) Inhibitors for Inflammatory Diseases" (2014) American Chemical Society, 5023-5038.

Clinical Trials "A Study in Patients with Atopic Eczema to Test How Effective BI 655130 Is and How Well It Is Tolerated" (2021) Last Update Posted, NCT03822832, 11 pgs.
Clinical Trials "A Study to Evaluate the Efficacy and Safety of ANB019 in Subjects With Palmoplantar Pustulosis (PPP)" NCT03633396, (2019) clinicaltrails.gov, 8 pgs.
Clinical Trials "BI655130 Single Dose in Generalized Pustular Psoriasis" (2018) Identifier: NCT02978690, 6 pgs.
Clinical Trials "History of Changes for Study: NCT03135548, Initial Dosing of BI 655130 in Palmoplantar Pustulosis Patients" (2020) clinicaltrials.gov, 5 pgs.
Clinical Trials "History of Changes for Study: NCT03782792, A Study to Test BI 655130 in Patients iwth Flare-up of a Skin Disease called Generalized Pustular Psorasis" (2018) clinicaltrials.gov, 6 pgs.
Clinical Trials "This Study Tests How Bl 655130 Works in Patients with Active Ulcerative Colitis. The Study also Tests how well BI 655130 is Tolerated and Whether it Helps the Patients" (2020) NCT03100864, 28 pgs.
Creative Diagnostics "Mouse anti-IL1RL2 Monoclonal Antibody" Product Information. Gene ID 8808. mRNA Ref Seq NM_00 3854. (2004).
Debets, Reno et al. "Two Novel IL-1 Family Members, IL-1d and IL-1e Function as an Antagonist and Agonist of NF-kB Activation Through the Orphan IL-1 Receptor-Related Protein 21" The Journal of Immunology (2001) vol. 167, pp. 1440-1446.
Dinarello, Charles et al. "IL-1 family nomenclature" Nature Immunology (2010) vol. 11, pp. 973-974.
Ding, Liping et al. "IL-36 cytokines in autoimmunity and inflammatory disease" (2018) Oncotarget, vol. 9, No. 2, 2895-2901.
Guido, Rafael V.C. et al. "Virtual Screening and Its Integration with Modern Drug Design Technologies" (2008) Current Medicinal Chemistry, vol. 15, 37-46.
International Search Report for PCT/US2012/064933 filed Nov. 14, 2012, dated Feb. 7, 2013.
International Search Report for PCT/US2019/021296 dated Feb. 27, 2020.
International Search Report PCT/EP2019/086521 dated Apr. 6, 2020.
International Search Report PCT/US2018/024296 dated Jun. 22, 2018.
International Search Report PCT/US2021/032713 dated Aug. 30, 2021, 12 pgs.
Johnston, Andrew et al. "IL-1 and IL-36 are dominant cytokines in generalized pustular psoriasis" (2017) J Allergy Clin Immunol, 109-120.
Johnston, Andrew et al. "IL-1F5, -F6, -F8, and -F9: A Novel IL-1 Family Signaling System that is Active in Psoriasis and Promotes Keratinocyte Antimicrobial Peptide Expression" The Journal of Immunology (2011) vol. 186, pp. 2613-2622.
Lazar, Eliane et al. "Transforming Growth Factor a: Mutation of Aspartic Acid 47 and Leucine 48 Results in Different Biological Activities" Molecular and Cellular Biology (1988) vol. 8, No. 3, pp. 1247-1252.
Lingel, Andreas et al. "Structure of IL-33 and its Interaction with the ST2 and IL-1RAcP Receptors—Insight into Heterotrimeric IL-1 Signaling Complexes" Structure (2009) vol. 17, pp. 1398-1410.
Lovenberg, Timothy W. et al. "Cloning of a cDNA encoding a novel interleukin-1 receptor related protein (IL1R-rp2)" Journal of Neuroimmunology, (1996) vol. 70, pp. 113-122.
Magne, David et al. "The new IL-1 Family Member IL-1F8 stimulates production of inflammatory mediators by synovial fibroblasts and articular chondrocytes" Arthritis Research & Therapy (2006) vol. 8:R80, 11 pgs.
Marrakchi, Slaheddine et al. "lnterleukin-36-Receptor Antagonist Deficiency and Generalized Pustular Psoriasis" New England Journal of Medicine (2011) vol. 365 pp. 620-628.
Matsuba et al., "Preparation of Super-High Affinity Rabbit Monoclonal Antibodies Against Estradiol.: Application to Highly Sensitive Estradiol Measurement", TOSOH Research & Technol. Review 2008, vol. 52, pp. 3-9.
McKeaugue, Maureen et al. "Challenges and Opportunities for Small Molecule Aptamer Development" (2012) Journal of Nucleic Acids, Article ID: 748913, 20 pgs.

(56) References Cited

OTHER PUBLICATIONS

McMahan, Catherine J. et al. "A Novel IL-1 receptor, cloned from B cells by mammalian expression, is expressed in many cell types" EMBO Journal (1991) vol. 10, No. 10, pp. 2821-2832.
NCBI Gene databases (IL1RL2 interleukin 1 receptor-like 2 [*Homo sapiens* (human)]; http:www.ncbi.nlm.nib.gov/gene/8808; downloaded May 18, 2014, 8 pgs.
Nishida, Atsushi et al. "Increased Expression of Interleukin-36, a Member of the Interleukin-1 Cytokine Family, in Inflammatory Bowel Disease" (2016) Inflamm Bowel Dis, vol. 22, No. 2, 303-314.
Nolan, S. et al. "505 Therapeutic activity of an anti-IL36R blocking antibody in inhibiting atopic dermatitis-like skin inflammation in mice" (2019) Journal of Investigative Dermatology, Society for Investigative Dermatology (SID) 2019, Meeting Abstract Supplement, 2 pgs.
Patrick, Garrett et al. "Epicutaneous Staphylococcus aureaus induces IL-36 to enhance IgE production and ensuing allergic disease" (2021) The Journal of Clinical Investigation, 1-15.
Puar, Neha et al. "New treatments in atopic dermatitis" (2020) Annals Allergy Asthma Immunology, 126, 21-21.
Qin, Jian-Zhong et al. "Role of NF-kB in the Apoptotic-resistant Phenotype of Keratinocytes" (1999) vol. 274, No. 53, 37957-37964.
Ramadas, Ravisankar A. et al. "IL-36a Exerts Pro-Inflammatory Effects in the Lungs of Mice" PLOS one (2012) vol. 7, Issue 9, e45784, 17 pgs.
Ramadas, Ravisankar A. et al. "Interleukin-1 Family Member9 Stimulates Chemokine Production and Neutrophil Influx in Mouse Lungs" Am J Respir Cell Mol Biol (2011) vol. 44, pp. 134-145.
Russell, Se et al. "IL-36a expression is elevated in ulcerative colitis and promotes colonic inflammation" (2016) Mucosal Immunology, vol. 9, No. 5, 1193-1204.
Scheibe, Kristina et al. "Inhibiting Interleukin 36 Receptor Signaling Reduces Fibrosis in Mice with Chronic Intestinal Inflammation" (2019) Gastroenterology, vol. 156, No. 4, 1082-1097.
Steidl et al., "In vitro affinity maturation of human GM-CSF antibodies by targeted CDR-diversification", Mol. Immunol, 2008, vol. 46, pp. 135-144.
Wang et al., J Pharm Sci., "Antibody Structure, Instability, and Formulation", (2007), 96(1):1-26.
Dinarello, Charles A. "Immunological and Inflammatory Functions of the Interleukin-1 Family" The Annual Review of Immunology (2009) vol. 27, pp. 519-550.
Boehringer Ingelheim "Boehringer Ingelheim R&D pushes to Transcend Disease Boundaries" (2018) Business Wire, 4 pgs.
Lacy, et al. "Correlation between Antibody Affinity and Activity: Understanding the Molecular Basis for a Picomolar to Femtomolar Increase in Affinity" (2009) Abstract, 1621-Pos, Board B465, vol. 96, Issue 3, S1, 317a-318a.
Bachelez, Herve et al. "Inhibition of the Interleukin-36 Pathway for the Treatment of Generalized Pustular Psoriasis" (2019) The New England Journal of Medicine, 380: 10, 981-983.
Satoh T K et al: "Are neutrophilic dermatoses autoinflammatory disorders?" (2018) The British Journal of Dermatology, vol. 178, No. 3, pp. 603-613.
Marzano Angelo V. et al: "Mechanisms of Inflammation in Neutrophil-Mediated Skin Diseases", (2019) Frontiers in Immunology, vol. 18, 2019, p. 1859.
Mrowietz Ulrich et al.: "Spesolimab, an Anti-Interleukin-36 Receptor Antibody, in Patients with Palmoplantar Pustulosis: Results of a Phase IIa, Multicenter, Double-Blind, Randomized,Placebo-Controlled Pilot Study", (2021) Dermatology and Therapy, vol. 11, No. 2, 571-585.
International Search Report PCT/US2021/041734 dated Nov. 11, 2021, 4 pgs.
"Interleukin-1 receptor-like 2 isoform a precursor", downloaded from https://ncbi.nlm.nlh.gov/protein/NP_003845.2?report+girevhist on Sep. 21, 2022.
Elias, IL-36 in chronic inflammation and fibrosis, JCI, vol. 131, 2021, 14 pages.
Melton, Interleukin-36 Cytokine/Receptor Signaling, Int. J. of Molecular Sci., vol. 21, 2020, 22 pages.
Neufert, Rationale for IL-36 receptor antibodies in ulcertaive colitis, Expert opinion on Biological Therapy, vol. 20, 2020, 5 pages, https://doi.org/10.1080.14712598.2020.1695775.
Scheibe, Inhibiting Interleukin 36 receptor signaling reduces fibrosis in mice with chronic intestinal inflammation, Gastroenterology, vol. 156, 2019, 27 pages.
International Search Report and Written Opinion for PCT.US2022/074888 dated Nov. 29, 2022.
International Search Report and Written Opinion for PCT/US2022/019742 dated Oct. 21, 2022.
Baliwag, Cytokines in psoriasis, Cytokine, vol. 73, 2015, 9 pages.
Baum, Generalized Pustular psoriasis and palmoplantar pustulosis both slow upregulation of the IL-36, neutrophil chemokine, and innate pathways that are modulated by spesolimab, and anti-IL-36 receptor antibody treatment, Journal of Investigative Dermatology, Adaptive and Auto-Immunity, www.jidonline.org., vol. 140, 2020, p. S5.
Baum, Treatment with spesolimab, an anti-interleukin-36 receptor antibody, in patients with generalized pustular psoriasis, ESDR 2019 Annual Meeting, Retrieved from Internet: URL:https://www.sciencedirect.com/science/article/pii/S0022202X19322444/pdfft?md5=main.pdf on Jun. 23, 2022, 1 page.
Baum, Pustular psoriasis: molecular pathways and effects of spesolimab in generalized pustular psoriasis, Journal of Allergy and clinical immunology, vol. 149. 2021, p. 1402-1412.
Brenner, Gernalized pustular psoriasis induced by systemic glucocorticosteroids, Bristish Journal of Dermatology, vol. 161, 2009, p. 964-963.
Yuan, Biology of IL-36 Signaling and its role in systemic Inflammatory Diseases, Frontiers in Immunology, vol. 10, 2019, p. 2532.
Zeng, Integrated analysis of gene expression profiles identifies transcription factors potentially involved in psoriasis pathogenesis, J. of Cellular Biochem., vol. 120, 2019, p. 12582-12594.
Tortola, Psoriasiform dermatitis is driven by IL-36-mediated DC-keratinocyte crosstalk, The J. of Clinical Investigation, vol. 122, 2012, p. 3965-3976.
Foster, IL-36 promotes myeloid cell infiltration activation and inflammatory activity in skin, The j. of immunolgy, vol. 192, 2014, p. 6053- 6061.
Swindell, 7th International Congress of psoriais: from gene to clinic: The Queen Elizabeth II Conference Centre, London, UK, Dec. 11-13, 2014, British Journal of Dermatology, vol. 171, 2014, 20 pages.
Kang, Rapid Formulation Development for Monoclonal Antibodies, BioProcess Chem., vol. 14, 2016, 4 pages.

* cited by examiner

ANTI-IL-36R ANTIBODY FORMULATIONS

SEQUENCE LISTING

The instant application contains a Sequence Listing which has been submitted in ASCII format via EFS-Web and is hereby incorporated by reference in its entirety. Said ASCII copy, created on Mar. 2, 2020 and is named 09-0694-US-2-SL.txt and is 146,026 bytes in size.

FIELD OF THE INVENTION

The present invention relates to a pharmaceutical formulation for a therapeutic antibody. More specifically, the present invention relates to a pharmaceutical formulation for an anti-IL-36R antibody disclosed herein.

BACKGROUND OF THE INVENTION

The anti-IL-36R antibodies described herein reduce or block IL36 ligand-mediated signaling and are useful in treating diseases or conditions associate with such signaling. There is a need for a stable liquid or lyophilized antibody formulation for the anti-IL-36R antibodies, which is suitable for parenteral administration, including intravenous, intramuscular, or subcutaneous injection to a human.

Therapeutic antibodies are large and complex molecules and, as such, subject to degradation processes, particularly in the liquid state. While antibody production and purification is a well-controlled process, developing a formulation which is stable and is suitable for delivery to the patient is a challenge. The instabilities of antibodies are a major obstacle for commercial development of antibody drugs. For instance, antibody preparations can have short shelf lives and antibodies may lose biological activity resulting from chemical and physical degradation during the storage. Chemical degradation processes include deamidation, racemization, hydrolysis, oxidation, beta elimination and disulfide exchange. Physical degradation processes include denaturation, aggregation, precipitation and adsorption (Cleland et al., Critical Reviews in Therapeutic Drug Carrier Systems, 1993, 10(4): 307-377). Although antibodies share certain structural similarities, development of commercially viable antibody pharmaceuticals has not been straightforward because of their unique and somewhat unpredictable solution behavior. Due to the significant difference in the primary sequence among different antibodies, the relative severity of the degradation pathways (e.g., denaturation, aggregation, surface adsorption, deamidation, oxidation, isomerization, fragmentation, etc.) can be significantly different. (Wang et al., J Pharm Sci., Antibody Structure, Instability, and Formulation, 2007, 96(1):1-26).

A number of formulation references are listed below.

U.S. Pat. No. 10,166,993 describes a reduced-viscosity concentrated protein formulation including a protein in an amount of at least about 80 mg/mL, a buffer in an amount of at least about 50 mM, so as to have a pH of about 4.2 to about 4.9 or about 7.1 to about 12.0 and having kinematic viscosity of about 50 cs or less at 25° C., which makes the formulation suitable for subcutaneous administration.

WO 2011/109365 describes a formulation comprising a concentrated protein in an amount greater than 100 mg/mL or less than about 200 mg/mL, a tonicifier of a salt and a buffer present in a combined amount of from about 110 mM to about 120 mM and a surfactant, wherein the formulation is hypotonic (having an osmolality of less than 290 milliOsmol (mOsm)).

U.S. Pat. No. 9,517,226 describes a formulation for anti-c-Met antibody. It discloses a liquid formulation of an anti-c-Met antibody, which contains a surfactant, a buffer, and a liquid medium, and the buffer includes succinic acid, citric acid or a combination thereof.

WO 2016/128564 describes pharmaceutical composition including an antibody, at least one buffer agent selected from the group consisting of acetate and histidine, at least one amino acid selected from the group consisting of glycine, asparagine and glutamine, and/or at least one excipient selected from the group consisting of trehalose, and mannitol, and a surfactant, wherein the pH of the composition is 5.0 to 6.5.

Despite the information these or similar references provide, it is conventionally understood that antibodies with different sequences behave unpredictably under a variety of conditions including shaking, long-term storage, exposure to light, freeze-thawing process, lyophilization process, etc. It is unpredictable how one antibody would behave in a formulation that was prepared specifically with or for another antibody or protein. For example, a slight variation in formulation can destabilize a protein and result in aggregation. Protein aggregates generally have reduced activity and more importantly, greater immunogenicity potential because of the multiplicity of epitopes and/or conformational changes. Immunoglobulin aggregates have been shown to cause serious renal failure and anaphylactoid reactions such as headache, fever, and chills (Wang et al., supra).

Accordingly, there exists a need for stable formulation of the anti-IL-36R antibodies described herein that exhibit for instance increased stability, low to undetectable levels of physical or chemical degradation, and little to no loss of the biological activity of the antibodies, even during long periods of storage.

SUMMARY OF THE INVENTION

The present invention addresses the above needs by providing stable liquid or lyophilized pharmaceutical formulations of anti-IL-36R antibody as described further below. In particular, the present invention provides stable liquid or powder pharmaceutical formulations of the anti-IL-36R antibodies disclosed herein. The anti-IL-36R antibody formulations of the present invention are useful for administration to mammals, particularly humans or patients suffering from autoimmune or other malignant diseases. The formulation according to the present invention has improved properties compared to other formulations existing in the art, as will be described below.

In a first aspect, the present invention provides a pharmaceutical formulation of an anti-IL-36R antibody, wherein said formulation comprises a therapeutic amount of an anti-IL-36R antibody or an antigen binding fragment thereof (disclosed herein) and i) a pharmaceutically acceptable buffer; or ii) a pharmaceutically acceptable tonicifying agent; or iii) a pharmaceutically acceptable stabilizing agent; or iv) a pharmaceutically acceptable salt; or v) a pharmaceutically acceptable surfactant; or vi) a pharmaceutically acceptable buffer and a pharmaceutically acceptable tonicifying agent; or vii) a pharmaceutically acceptable buffer, a pharmaceutically acceptable tonicifying agent and a pharmaceutically acceptable stabilizing agent; or viii) a pharmaceutically acceptable buffer, a pharmaceutically acceptable tonicifying agent, a pharmaceutically acceptable stabilizing agent and a pharmaceutically acceptable salt; or ix) a pharmaceutically acceptable buffer, a pharmaceutically acceptable tonicifying agent, a pharmaceutically acceptable stabilizing agent, a pharmaceutically acceptable salt and a pharmaceutically acceptable surfactant; each in pharmaceutically acceptable quantities and at a pharmaceutically acceptable pH.

In a second aspect, the present invention relates to a pharmaceutical formulation of a therapeutic anti-IL-36R antibody or antibody fragment (disclosed herein), wherein said formulation comprises: (a) the anti-IL-36R antibody or an antigen binding fragment thereof present at a concentration within the range from about 0.5 mg/mL to about 220 mg/mL and (b) a pharmaceutically acceptable buffer; wherein the formulation is characterized by a pH within the range from about 5 to about 8. In an embodiment relating to this aspect, the buffer is present at a concentration within the range from about 20 mM to about 80 mM. In another embodiment relating to this aspect, the formulation further comprises a pharmaceutically acceptable tonicifying agent. In a related embodiment, the tonicifying agent is present at a concentration of about 100 mM to about 250 mM.

In a third aspect, the present invention provides a pharmaceutical product comprising a vial or syringe and devices (e.g. autoinjector, needle safety device) for administration, the pharmaceutical product comprises the pharmaceutical formulation according to any of the first or second aspect the present invention.

In a forth aspect, the present invention relates to a method of making a pharmaceutical formulation of the present invention, said method comprising: a) culturing mammalian cells having stably incorporated into their genome one or more nucleic acids encoding the light and heavy chains of an anti-IL-36R antibody (as disclosed herein) so that the cells secrete the antibody into the cell culture media, and purifying the antibody from the cell culture media; and b) preparing the formulation according to any of the first or second aspects.

In a fifth aspect, the present invention relates to a method of reducing aggregation and/or fragmentation of an anti-IL-36R antibody disclosed herein, comprising formulating the antibody in a buffer system and surfactant and evaluating data (e.g. any antibody aggregation) before and after the antibody is formulated. In an embodiment relating to the fifth aspect, the antibody is formulated according to any of the embodiments of the first or second aspects.

In a sixth aspect, the present invention relates to a kit of parts, including at least a container including a pharmaceutical formulation according to any of aspects first or second, and an injection device according to aspect third. In an embodiment relating to the sixth aspect, the injection device is a pre-assembled injection device including an autoinjector or a needle safety device. In a related embodiment, the autoinjector or needle safety device each includes: (a) about 300 mg of the antibody in a total volume of about 2 mL; (b) about 225 mg of the antibody in a total volume of about 1.5 mL; (c) about 150 mg of the antibody in a total volume of about 1 mL; (d) about 75 mg of the antibody in a total volume of about 0.5 mL; or (e) about 60 mg of the antibody in a total volume of about 0.4 mL.

According to yet another aspect of the present invention, the use of a formulation according to the invention, of a pre-assembled injection device according to the invention or of a kit of parts according to the invention, for infusion, intravenous and/or subcutaneous administration is provided.

According to yet another aspect of the present invention, the use of a formulation according to the invention, of a pre-assembled injection device according to the invention or of a kit of parts according to the invention, for treatment of at least one disease selected from the group consisting of autoimmune disorders and/or malignant diseases is provided. Non-restricting examples for autoimmune disorders covered by said definition include psoriasis, rheumatoid arthritis, inflammatory bowel disease or psoriatic arthritis, chronic obstructive pulmonary disorder (COPD), asthma, scleroderma, palmoplantar pustulosis, generalized pustular psoriasis, atopic dermatitis, diabetic nephropathy, lupus nephritis, scleroderma, ankylosing spondylitis, deficiency in the IL-36 receptor antagonist autoimmune disease (DITRA), deficiency in the IL-1 receptor antagonist autoimmune disease (DIRA) or cryopyrin associated periodic syndromes (CAPS), rheumatoid arthritis (RA), systemic lupus erythematosus (SLE), scleroderma, Sjogren's syndrome, multiple sclerosis, psoriasis, psoriatic arthritis, inflammatory bowel disease (e.g., ulcerative colitis and Crohn's disease), pulmonary inflammation, asthma, idiopathic thrombocytopenic purara (ITP) epithelial inflammatory disorders, fibrosis and ankylosing spondylitis. In a further preferred embodiment the kit comprises instructions for subcutaneous or intramuscular administration of the formulation to a subject.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

DETAILED DESCRIPTION OF THE INVENTION

Figure 1:
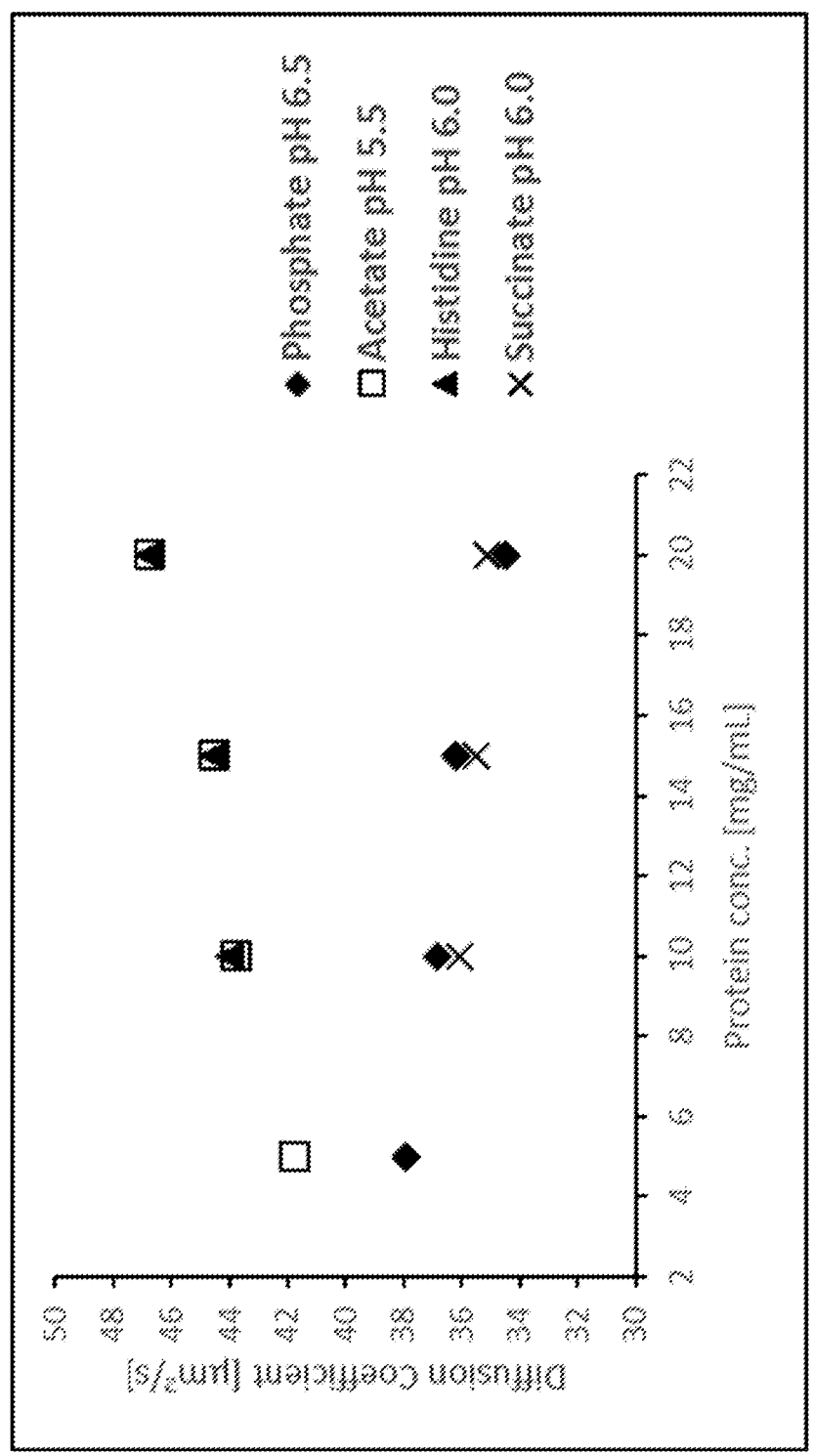
FIG. 1 shows the colloidal stability by diffusion coefficient, measured by DLS. Protein concentration in the respective buffers was varied from 5 to 20 mg/mL, as shown on X-axis. Diffusion coefficient is shown on the Y-axis of the tested buffers.

Without wishing to be bound by any theory or mechanism, the present invention is in part based on the unexpected discovery that showed that an anti-IL-36R formulation of the present invention with the lowest melting temperature value (Tm) correlated with the most promising properties, i.e., minimized protein-protein interaction, highest degree of diffusivity and increased long-term stability. See the Examples. This is contrary to the conventional notion that an increased Tm correlates with an increased long-term stability of the proteins studied (see, e.g., He et al., J Pharm Sci 2011; 100:1330-40).

As discussed earlier, physical and chemical instability of antibodies is a complex function of solution conditions, temperature and their primary structure. Antibodies are for example susceptible to deamidation, isomerization, oxidation, proteolysis, aggregation and other modifications. These phenomena are suspected to result in decreasing efficacy or even potential clinical side-effects or toxicity, since aggregates can reduce the efficacy and enhance the immunogenicity of the protein drug. Antibody aggregation is also a source of batch to batch variability in the antibody production chain and its control leads to regulatory and quality control burden which have extremely costly consequences. Further, aggregation of antibodies affects their stability in storage, including shelf-life and their useable administration time, once removed from optimum storage conditions.

An aqueous antibody formulation usually requires at least a buffer to maintain a given pH range, and a tonicifying agent to ensure that the formulation has a similar osmolality as physiological liquids.

It is desirable to provide therapeutic antibodies for the treatment of chronic diseases in a form that they can be administered by the patient himself or herself ("home use" or "self-administration" or "self-injection"), because, in many cases, the drug will have to be administered frequently for a long time. The suitability of a formulation for self-administration will thus increase patient compliance and reduce costs, as the patient does not have to see medical personnel each time he or she needs the drug injected.

In solutions, which are not stored at optimum conditions, such as at increased temperatures above the recommended range of 2-8° C., unwanted degradation occurs, which includes the formation of insoluble and/or soluble aggregates. Those insoluble and soluble aggregates are likely to be formed in the liquid state by association of the antibody molecules. In cases when a liquid formulation is stored for a long period of time, the bioactivity of the antibody molecules can be reduced due to e.g. aggregation or oxidation. The cycle of freezing and thawing may also lead to the formation of degraded and aggregated antibody molecules.

As a result the solutions may exhibit lowered activity, increased toxicity, and/or increased immunogenicity. Indeed, polypeptide precipitation can lead to thrombosis, non-homogeneity of dosage form, and immune reactions. Thus, the safety and efficacy of any pharmaceutical formulation of a polypeptide is directly related to its stability.

However, the suitability for self-administration creates new challenges with respect to shelf life. The patient will have to store considerable amounts of drug at home, where storage conditions are often less suitable than in a medical practice. A formulation comprising a therapeutic antibody, which is suitable for self-administration will thus have to exceed existing formulations in terms of storage stability even under suboptimal conditions, e.g. break in the cooling chain or condition under which the formulation or drug product should remain.

For home use and/or self-administration, the patient needs to administer the drug subcutaneously or intramuscularly. In order to deliver the required amount, the drug dose for home use often requires a higher protein concentration than needed for intravenous use due to injection volume limitations. A higher protein concentration, however, increases the viscosity of the solution. As the viscosity increases, the drug delivery by a syringe needle becomes challenging. Additionally, some buffer solutions are known to cause pain when present in products administered subcutaneously or intramuscularly.

Thus, there is a need for stable, antibody formulations that provide dosing advantages and administrative advantages, particularly with respect to improved stability in storage, including shelf-life and their useable administration.

The above-mentioned problems are solved by the embodiments characterized in the claims and described further below.

Definitions

A phrase such as "an aspect" does not imply that such aspect is essential to the present invention or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure.

The term "about" shall generally mean an acceptable degree of error or variation for the quantity measured given the nature or precision of the measurements. Typical, exemplary degrees of error or variation are within 5% or within 3% or within 1% of a given value or range of values. For example, the expression of "about 100" includes 105 and 95 or 103 and 97 or 101 and 99, and all values in between (e.g., 95.1, 95.2, etc. for range of 95-105; or 97.1, 97.2, etc. for the range of 97-103; 99.1, 99.2, etc. for the range of 99-101). Numerical quantities given herein are approximates unless stated otherwise, meaning that the term "about" can be inferred when not expressly stated.

The general embodiments "comprising" or "comprise" as used herein encompass the more specific embodiment "consisting of". Furthermore, singular and plural forms are not used in a limiting way. As used herein, the singular forms "a", "an" and "the" designate both the singular and the plural, unless expressly stated to designate the singular only.

A "pharmaceutical formulation" or "formulation" refers to the process but also the product of a process in which an active drug or agent is combined with chemical substances to produce a final medicinal or drug product, the final formulation therefore refers to medicinal products such as liquids, powders or compositions. Therefore, in one embodiment, a pharmaceutical formulation is a pharmaceutical composition.

A "pharmaceutical composition" refers in this context to a liquid or powder preparation which is in such form as to permit the biological activity of the active ingredient(s) to be unequivocally effective, and which contains no additional components which are significantly toxic to the subjects to which the composition would be administered. Such compositions are sterile. A "powder" refers to a freeze-dried or lyophilized or a spray-dried pharmaceutical composition for parenteral use. The powder is reconstituted or dissolved typically in water. Lyophilisation is a low temperature dehydration process which involves freezing the product, lowering pressure, then removing the ice by sublimation. Freeze drying results in a high quality product because of the low temperature used in processing. For a well-developed lyophilized formulation, the shape and appearance of the product is maintained over time and the quality of the rehydrated product is excellent. Spray drying is a method of producing a dry powder from a liquid or slurry by rapidly drying with a hot gas and with the goal of achieving a consistent particle size distribution.

As used herein, the term "Water" refers to water for injection.

The "Pharmaceutically acceptable" excipients (vehicles, additives) are those which are suitable for parenteral administration to a subject.

In one embodiment, the pharmaceutical formulation of the present invention is stable.

"Stability" refers to chemical stability and physical stability and can be evaluated qualitatively and/or quantitatively using various analytical techniques that are described in the art and are reviewed in for example Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Those methods include the evaluation of aggregate and particle formation (for example using size exclusion chromatography, by measuring turbidity, sub-visible particles by light obscuration of or microflow imaging, and/or by visual inspection); by assessing charge heterogeneity using cation exchange chromatography or capillary isoelectric focusing; mass spectrometric analysis; capillary gel electrophoresis (CGE) analysis to compare reduced and intact antibody; peptide map (for example tryptic or Lys-C digest) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomerization), clipping/hydrolysis/fragmentation (e.g. hinge region fragmentation), succinimide formation, unpaired cysteine(s), etc. A "deamidated" monoclonal antibody herein is one in which one or more asparagine residue thereof has been modified, e.g. to an aspartic acid or an isoaspartic acid by a post-translational modification. In order to measure stability, a sample of the formulation of the invention may be tested in a stability study, wherein a sample is exposed for a selected time period to a stress condition followed by quantitative and qualitative analysis of the chemical and physical stability using an adequate analytical technique.

Accordingly, stability can be measured at a selected temperature for a selected time period for instance by storing a sample at different temperatures such as −40° C., 5° C., 25° C. and 40° C. for up to 2 months and by using for instance HP-SEC, CEX, light obscuration, CGE or Binding activity for qualitative and quantitative analysis.

According to the above, a "stable formulation" is one in which the antibody is physically and chemically stable and/or retains its biological activity upon storage.

"Chemical stability" can be assessed by detecting and quantifying chemically altered forms of the antibody. Chemical alteration may involve size modification (e.g. clipping) which can be evaluated by, for example, using size exclusion chromatography, CGE and/or matrix-assisted laser desorption ionization/time-of-flight mass spectrometry (MALDI/TOF MS). Other types of chemical alteration include charge alteration (e.g. occurring as a result of deamidation) which can be evaluated for example by ion-exchange chromatography. In context of the invention chemical stability is for example measured by cationic exchange chromatography (CEX), wherein a change of for example 5% may be considered as significant.

"Physical stability" refers substantially in context of the invention to an antibody having little or no signs of aggregation, precipitation and/or denaturation. Methods to access the physical stability are for example size exclusion chromatography (SEC), light obscuration (LO) and color and clarity. For size exclusion chromatography (SEC) a difference of for example ≥0.1% of the content might be considered as significantly different in the context of the invention under the tested conditions depending on the column used, operating pressure, flow rate of the buffer.

An antibody "retains its biological activity" in a pharmaceutical formulation, if the antibody in a pharmaceutical formulation is biologically active for its intended purpose. For example, biological activity is retained if the biological activity of the antibody in the pharmaceutical composition is within about 30%, about 20%, or about 10% (within the errors of the assay) of a reference standard (e.g., as determined in an antigen binding assay). As known by those skilled in the art, the percentage of monomeric antibodies maintained in the solution is of utmost importance for a suitable pharmaceutically active composition. Since aggregates may be responsible for causing several as well as severe side effects, the content of monomers displays the actual pharmaceutically active amount of the drug or the antibody or antibody fragment thereof.

The term "stress" or "stress condition" in context of the invention refers to e.g. mechanical stress, thermal stress, light stress or stress resulting from freezing and thawing. Methods and conditions to simulate mechanical stress, thermal stress, light stress or stress resulting from freezing and thawing are diverse and known to those skilled in the art. Mechanical stress may be for example shaking with 300 rpm at room temperature for up to 48 hrs. Thermal stress refers for example to the storage at decreased or increased temperatures for an amount of time, in one example samples may be stored at 5° C., 25° C. and 40° C., wherein for instance 25° C. and 40° C. refer to a stress condition. Light stress might be for example storing the samples at a light intensity of about 1100 lux for 5 days at room temperature. Samples might be exposed to stress from freezing and thawing by exposing the samples to several cycles of freezing, e.g. at −40° C. for 24 hrs and thawing at room temperature for 2 hrs, wherein the cycles are repeated 3 times.

As used herein "buffer" refers to a buffered solution that resists changes in pH by the action of its acid-base conjugate components. The "pH" herein refers to the acidity or basicity of the composition at room temperature. Standard methods to measure the pH of a composition are known to the skilled in the art. Typically, measuring pH consists of calibrating the instrument, placing the electrodes in a well-mixed sample, and then reading the pH directly from the pH meter. The exemplary buffers of the present invention include acetate, citrate, histidine, succinate, phosphate and Tris.

As used herein, the term "tonicifying agent" or "tonicity agent" or "tonicifyer" refers to substances providing an osmotic pressure equivalent to that of serum in the body including salts (e.g. sodium chloride, potassium chloride, magnesium chloride, magnesium sulfate ($MgSO_4$)) or sugars/polyols (e.g. sucrose, trehalose, sorbitol, glycerol, mannitol or dextrose). In addition, sugars/polyols present in the solution act as a cryoprotectant for the protein which allows the drug substance to be frozen without damage. This permits shipment in the frozen form and long-term storage of the drug substance prior to the filling of drug product.

The exemplary tonicifying agents of the present invention include sodium chloride, potassium chloride, magnesium chloride, magnesium sulfate ($MgSO_4$) (salts) and/or sucrose, trehalose, sorbitol, glycerol, mannitol or dextrose (sugars/polyols). In certain embodiments the tonicifying agent is a sugar or a polyol selected from the group consisting of sucrose, trehalose, sorbitol, glycerol, mannitol and dextrose.

As used herein, the term "stabilizer" or "stabilizing agent" refers to substances contributing to the stability of the active ingredient in a pharmaceutical formulation. The exemplary stabilizing agents of the present invention include arginine, histidine, glycine, cysteine, proline, methionine, lysine, or pharmaceutically acceptable salts thereof.

As used herein, the term "surfactant" refers to substances which tend to reduce the surface tension of a liquid in which they are dissolved. The exemplary surfactants of the present invention include poloxamer 188, polysorbate 20, polysorbate 40, polysorbate 60 or polysorbate 80.

The present invention relates to anti-IL-36R antibody formulations for administration to mammals, in particular humans. The formulations of the present invention include humanized antibodies disclosed herein that bind to IL-36 receptor (IL-36R). In specific embodiments herein, the sequences of these humanized antibodies are identified.

The formulations of this invention minimize the formation of antibody aggregates and turbidity and insure that the antibody maintains its bioactivity over time. In particular the inventors of the present invention made the surprising finding as demonstrated in the Examples that the content of monomers of the formulated antibody is more stable and the formation of aggregates is far less pronounced in some of the formulations of the present invention at 40° C. when stored up to 3 months compared to other formulations tested. See Example 7.

As a result, in a first aspect, the present invention provides a pharmaceutical formulation of an anti-IL-36R antibody, wherein said formulation comprises a therapeutic amount of an anti-IL-36R antibody or an antigen binding fragment thereof (disclosed herein) and i) a pharmaceutically acceptable buffer; or ii) a pharmaceutically acceptable tonicifying agent; or iii) a pharmaceutically acceptable stabilizing agent; or iv) a pharmaceutically acceptable salt; or v) a pharmaceutically acceptable surfactant; or vi) a pharmaceutically acceptable buffer and a pharmaceutically acceptable tonicifying agent; or vii) a pharmaceutically acceptable buffer, a pharmaceutically acceptable tonicifying agent and a pharmaceutically acceptable stabilizing agent; or viii) a pharmaceutically acceptable buffer, a pharmaceutically acceptable tonicifying agent, a pharmaceutically acceptable stabilizing agent and a pharmaceutically acceptable salt; or ix) a pharmaceutically acceptable buffer, a pharmaceutically acceptable tonicifying agent, a pharmaceutically acceptable stabilizing agent, a pharmaceutically acceptable salt and a pharmaceutically acceptable surfactant; each in pharmaceutically acceptable quantities and at a pharmaceutically acceptable pH. The formulation according to the present invention has improved properties as will be described below.

In the following Table, typical concentration ranges of the components of the formulations according to the present invention are provided:

TABLE I

Typical concentration ranges of the components of the formulations

| Component | Concentration Range |
|---|---|
| Anti-IL-36R antibody | 0.5 to 220 mg/mL |
| Buffer: acetate, citrate, histidine, succinate, phosphate, TRIS | 20 to 80 mM |
| Tonicity agent: e.g. sucrose, trehalose, sorbitol, glycerol, mannitol, dextrose and combinations thereof | 100 to 250 mM |
| Stabilizer: arginine, histidine, glycine, proline, methionine, lysine, cysteine or pharmaceutically acceptable salts thereof | 0 to 80 mM |
| Salt: NaCl, $MgCl_2$, $MgSO_4$, KCl | 0 to 150 mM |
| Surfactants: polysorbates (20, 40, 60, 80), poloxamer (188) | 0.1 to 1.5 g/L (equal to 0.01 to 0.15% (w/v)) |

Following Tables provide exemplary formulations of the present invention and reference formulations XI and XIb:

TABLE 1a

Exemplary formulations

| Formula | Anti-IL-36R antibody | Buffer | Tonicifier Agent | Stabilizer | Salt | Surfactant | pH |
|---|---|---|---|---|---|---|---|
| I | 20 mg/ml | 40 mM Histidine | 120 mM Sucrose | 50 mM L-Arginine | 5 mM NaCl | 1.0 g/L Polysorbate 20 | 6.0 |
| II | 60 mg/mL | 45 mM Acetate | 150 mM Sucrose | 25 mM L-Arginine | — | 0.4 g/L Polysorbate 20 | 5.5 |

TABLE 1a-continued

Exemplary formulations

| Formula | Anti-IL-36R antibody | Buffer | Tonicifier Agent | Stabilizer | Salt | Surfactant | pH |
|---|---|---|---|---|---|---|---|
| III | 20 mg/mL | 45 mM Acetate | 180 mM Sucrose | 25 mM Glycine | — | 0.4 g/L Polysorbate 80 | 5.5 |
| IV | 150 mg/mL | 25 mM Citrate | 150 mM Trehalose | 25 mM Methionine | — | 0.2 g/L Polysorbate 20 | 6.0 |
| V | 60 mg/mL | 25 mM Histidine | 160 mM Sucrose, 20 mM Mannitol | — | — | 0.2 g/L Polysorbate 20 | 6.0 |
| VI | 20 mg/mL | 25 mM Citrate | 200 mM Sucrose | — | — | 0.4 g/L Polysorbate 80 | 6.5 |
| VII | 150 mg/mL | 45 mM acetate | 150 mM sucrose | 25 mM L-Arginine | — | 0.4 g/L Polysorbate 20 | 5.5 |
| VIII | 15 mg/mL | 35 mM Histidine | 180 mM Trehalose | 25 mM L-Arginine | 3 mM NaCl | 0.4 g/L Polysorbate 80 | 6.0 |
| IX | 80 mg/mL | 25 mM Acetate | 100 mM Mannitol | — | 50 mM NaCl | 0.2 g/L Polysorbate 20 | 5.5 |
| X | 100 mg/mL | 20 mM Succinate | 220 mM Sucrose | — | — | 0.1 g/L Polysorbate 80 | 6.0 |
| XI | 60 mg/mL | 25 mM Citrate | — | — | — | 0.4 g/L Polysorbate 20 | 6.5 |

TABLE 1b

Exemplary formulations

| Formula | Anti-IL-36R antibody | Buffer | Tonicifier Agent | Stabilizer | Salt | Surfactant | pH |
|---|---|---|---|---|---|---|---|
| Ib | 20 mg/mL to 150 mg/mL | 40 mM Histidine | 120 mM Sucrose | 50 mM L-Arginine | 5 mM NaCl | 1.0 g/L Polysorbate 20 | 6.0 |
| IIb | 20 mg/mL to 150 mg/mL | 45 mM Acetate | 150 mM Sucrose | 25 mM L-Arginine | — | 0.4 g/L Polysorbate 20 | 5.5 |
| IIIb | 20 mg/mL to 150 mg/mL | 45 mM Acetate | 180 mM Sucrose | 25 mM Glycine | — | 0.4 g/L Polysorbate 80 | 5.5 |
| IVb | 20 mg/mL to 150 mg/mL | 25 mM Citrate | 150 mM Trehalose | 25 mM Methionine | — | 0.2 g/L Polysorbate 20 | 6.0 |
| Vb | 20 mg/mL to 150 mg/mL | 25 mM Histidine | 160 mM Sucrose, 20 mM Mannitol | — | — | 0.2 g/L Polysorbate 20 | 6.0 |
| VIb | 20 mg/mL | 25 mM Citrate | 200 mM Sucrose | — | — | 0.4 g/L Polysorbate 80 | 6.5 |
| VIIb | 20 mg/mL to 150 mg/mL | 45 mM acetate | 150 mM sucrose | 25 mM L-Arginine | — | 0.4 g/L Polysorbate 20 | 5.5 |
| VIIIb | 20 mg/mL to 150 mg/mL | 35 mM Histidine | 180 mM Trehalose | 25 mM L-Arginine | 3 mM NaCl | 0.4 g/L Polysorbate 80 | 6.0 |
| IXb | 20 mg/mL to 150 mg/mL | 25 mM Acetate | 100 mM Mannitol | — | 50 mM NaCl | 0.2 g/L Polysorbate 20 | 5.5 |
| Xb | 20 mg/mL to 150 mg/mL | 20 mM Succinate | 220 mM Sucrose | — | — | 0.1 g/L Polysorbate 80 | 6.0 |

TABLE 1b-continued

Exemplary formulations

| Formula | Anti-IL-36R antibody | Buffer | Tonicifier Agent | Stabilizer | Salt | Surfactant | pH |
|---|---|---|---|---|---|---|---|
| XIb | 20 mg/mL to 150 mg/mL | 25 mM Citrate | — | — | — | 0.4 g/L Polysorbate 20 | 6.5 |

In accordance with the above, in one embodiment the pharmaceutical composition of the present invention having at least one feature selected from the group consisting of:
(a) significantly decreased percentage of aggregates as measured by High Performance Size Exclusion Chromatography (HP-SEC),
(b) significant higher percentage of monomers after storage at about 40° C. as measured by HP-SEC,
(c) higher percentage of main peak, which correlates to less chemical degradation, measured by CEX,
(d) lower turbidity by visual assessment and/or lower turbidity value in Formazine Nephelometry Units (FNU) and
(e) lower values of subvisible particles (≥10 μm and ≥25 μm), as compared to a reference formulation.

In accordance with the present invention the terms "decreased", "higher", "less", "smaller", "increased", "lower" or "less" the like, e.g., which denote quantitative differences between two states, which includes significant differences between the two states.

In accordance with the present invention, the term "reference formulation" refers to formulation XI in Table Ia and/or formulation XIb in Table Ib. In an embodiment, the reference formulation comprises an anti-IL-36R antibody or an antigen binding fragment thereof as disclosed herein e.g. present in the same concentration as that to which the formulation is compared but with a different amount and/or type of a buffer system and/or a different amount and/or type of tonicifying agent (and/or a different amount and/or type of surfactant), such as in formulation XI in Table Ia and/or formulation XIb in Table Ib; wherein the formulation is characterized by a pH within the range from about 5 to about 7 when in aqueous form.

In an embodiment, the formulations of the present invention have decreased amount of aggregates after storage at about 40° C. by at least about 10%, 25% or 50% as compared to the amount of aggregates of a reference formulation, as measured by High Performance Size Exclusion Chromatography (HP-SEC). For example, if an experimental value decreases from 1.0% to 0.9%, the relative decrease is 10% in accordance to the previous sentence.

In an embodiment, the formulations of the present invention have higher amount of monomers after storage at about 40° C. by at least about 10%, 25% or 50% as compared to a reference formulation, after storage at about 40° C. as measured by HP-SEC.

In an embodiment, the formulations of the present invention have increased main peak amounts (less chemical degradation) after storage at about 40° C. by at least about 10%, 25% or 50% as compared to a reference formulation, as measured by CEX.

In an embodiment, the formulations of the present invention have lower turbidity value by at least about 10%, 25% or 50% as compared to a reference formulation, in Formazine Nephelometry Units (FNU).

In an embodiment, the formulations of the present invention have less increase in sub-visible particles (such as ≥10 μm and ≥25 μm) by at least about 10%, 25%, 50%, 75% or 100% as compared to a reference formulation.

In an embodiment relating to the first aspect, the anti-IL-36R antibody or antigen binding fragment thereof is present in the formulation at a concentration within the range from about 0.5 mg/mL to about 220 mg/mL, or a range from about 10 to about 175 mg/mL, or a range from about 10 to about 30 mg/mL, or a range from about 45 to about 75 mg/mL, or a range from about 125 to about 175 mg/mL, or at a concentration of about 15 mg/mL, about 20 mg/mL, about 25 mg/mL, about 30 mg/mL, about 60 mg/mL, about 75 mg/mL, about 80 mg/mL, about 100 mg/mL or about 150 mg/mL. In one embodiment, the anti-IL-36R antibody or antigen binding fragment thereof is present in the formulation at a concentration of about 20 mg/mL. In another embodiment, the anti-IL-36R antibody or antigen binding fragment thereof is present in the formulation at a concentration of about 60 mg/mL. In yet another embodiment, the anti-IL-36R antibody or antigen binding fragment thereof is present in the formulation at a concentration of about 150 mg/mL.

In another related embodiment, the pharmaceutically acceptable buffer is present in the formulation at a concentration within the range from about 20 mM to about 80 mM, or a range from about 20 to about 70 mM, or a range from about 20 to about 60 mM, or a range from about 20 mM to about 50 mM, or at a concentration of about 20 mM, about 25 mM, about 35 mM, about 40 mM, about 45 mM, about 50 mM, about 60 mM. The buffer may comprise histidine, phosphate, succinate, citrate, acetate or TRIS. In certain embodiments the buffer is selected from the group consisting of histidine, phosphate, succinate, citrate, acetate and TRIS, particularly acetate and citrate. In one embodiment the buffer is citrate. In another embodiment the buffer is histidine. In yet another embodiment the buffer is acetate.

In another related embodiment, the pharmaceutically acceptable tonicifying agent is present in the formulation at a concentration within the range from about 100 mM to about 250 mM, or a range from about 120 to about 220 mM, or a range from about 130 to about 190 mM, or a range from about 140 to about 190 mM, or at a concentration of about 100 mM, about 120 mM, about 150 mM, about 180 mM, about 200 mM, about 220 mM. The tonicifying agent may be a salt, a sugar or a polyol. In one embodiment the tonicifying agent is one or more sugar and/or a polyol. The tonicifying agent may one or more sugar and/or polyol comprising sucrose, trehalose, sorbitol, glycerol, mannitol or dextrose, particularly sucrose or trehalose. In one embodiment the tonicifying agent is one or more sugar and/or polyol selected from the group consisting of sucrose, trehalose, sorbitol, glycerol, mannitol or dextrose, particularly sucrose and trehalose, particularly the tonicifying agent is sucrose or the tonicifying agent is trehalose.

In another related embodiment, a pharmaceutically acceptable stabilizing agent is present in the formulation at a concentration within the range from about 0 mM to about 80 mM, or a range from about 0 to about 70 mM, or a range from about 0 to about 60 mM, or a range from about 0 to about 50 mM. In case a stabilizing agent is present, it may be present at a concentration within the range from about 5 mM to about 80 mM, or from about 10 mM to 70 mM, or from about 20 mM to 50 mM, or at a concentration of about 25 mM, or about 50 mM. In an embodiment, the stabilizing agent is present in the formulation at a concentration of about 20 mM, or about 25 mM, or about 30 mM, or about 35 mM, or about 40 mM or about 45 mM. The stabilizing agent may comprise an amino acid, such as arginine, histidine, glycine, cysteine, proline, methionine, lysine, aspartate, glutamate or pharmaceutically acceptable salts thereof, more particularly arginine. In one embodiment, the stabilizing agent is selected from the group consisting of arginine, histidine, glycine, cysteine, proline, methionine, lysine, aspartate, glutamate and a pharmaceutically acceptable salt thereof. In yet another embodiment, the stabilizing agent is L-arginine or a pharmaceutically acceptable salt thereof.

In another related embodiment, the pharmaceutically acceptable salt is present in the formulation at a concentration of within the range from about 0 to about 150 mM, or a range from about 0 to about 120 mM, or a range from about 0 to about 90 mM, or a range from about 0 to about 10 mM, or at a concentration of about 3 mM, 5 mM, 10 mM, 25 mM or 50 mM. In another related embodiment, the pharmaceutically formulation comprises one or more sugar and/or polyol as a tonicifying agent and further a pharmaceutically acceptable salt at a concentration of within the range from about 3 to about 150 mM, or a range from about 3 to about 120 mM, or a range from about 3 to about 90 mM, or a range from about 3 to about 10 mM, or at a concentration of about 3 mM, 5 mM, 10 mM, 25 mM or 50 mM. The salt may comprise sodium chloride (NaCl), magnesium chloride (MgCl$_2$), magnesium sulfate (MgSO$_4$), potassium chloride (KCl), lithium chloride (LiCl), calcium chloride (CaCl$_2$), boric acid salts or zinc chloride (ZnCl$_2$). In one embodiment the salt is selected from the group consisting of sodium chloride (NaCl), magnesium chloride (MgCl$_2$), magnesium sulfate (MgSO$_4$), potassium chloride (KCl), lithium chloride (LiCl), calcium chloride (CaCl$_2$), boric acid salts and zinc chloride (ZnCl$_2$). In a specific embodiment the salt is sodium chloride.

In another related embodiment, the pharmaceutically acceptable surfactant is present in the formulation at a concentration within the range from about 0 g/L to about 1.5 g/L, or a range from about 0.1 g/L to about 1.5 g/L, or a range from about 0.1 to about 1.0 g/L, or a range from about 0.1 to about 0.6 g/L, or a range from about 0.15 to about 0.5 g/L, or at a concentration of about 0.1 g/L, 0.2 g/L, 0.4 g/L, 0.5 g/L or 1 g/L. The surfactant may comprise polysorbate 20, polysorbate 40, polysorbate 60 or polysorbate 80. In one embodiment the surfactant is selected from the group consisting of polysorbate 20, polysorbate 40, polysorbate 60 and polysorbate 80, particularly selected from the group consisting of polysorbate 20 and polysorbate 80.

In an embodiment related to the first aspect, the formulation is characterized by a pH within the range from about 5 to about 8, or a range from about 5 to about 7, or a range from about 5 to about 6.5. In another related embodiment, the pH is about 5, about 5.5, about 6, about 6.5, about 7, about 7.5 or about 8. The person skilled in the art will understand that the pH of the formulation refers to the pH of the formulation when in aqueous form.

In an embodiment related to the first aspect, the anti-IL-36R antibody or antigen binding fragment thereof comprises a light chain variable region comprising the amino acid sequence of SEQ ID NO: 80; and a heavy chain variable region comprising the amino acid sequence of SEQ ID NO: 87; or a light chain variable region comprising the amino acid sequence of SEQ ID NO: 80; and a heavy chain variable region comprising the amino acid sequence of SEQ ID NO: 88; or a light chain variable region comprising the amino acid sequence of SEQ ID NO: 80; and a heavy chain variable region comprising the amino acid sequence of SEQ ID NO: 89. In one embodiment the anti-IL-36R antibody comprises a light chain comprising an amino acid sequence set forth as SEQ ID NO:118 and a heavy chain comprising an amino acid sequence set forth as SEQ ID NO:125; or a light chain comprising an amino acid sequence set forth as SEQ ID NO:118 and a heavy chain comprising an amino acid sequence set forth as SEQ ID NO:126; or a light chain comprising an amino acid sequence set forth as SEQ ID NO:118 and a heavy chain comprising an amino acid sequence set forth as SEQ ID NO:127. In a particular embodiment, the anti-IL-36R antibody comprises a light chain variable region comprising the amino acid sequence of SEQ ID NO: 80; and a heavy chain variable region comprising the amino acid sequence of SEQ ID NO: 89. In another particular embodiment, the anti-IL-36R antibody consists of a light chain comprising an amino acid sequence set forth as SEQ ID NO:118 and a heavy chain comprising an amino acid sequence set forth as SEQ ID NO:127.

In an embodiment related to the first aspect, the anti-IL-36R antibody consists of a light chain variable region comprising the amino acid sequence of SEQ ID NO: 80; and a heavy chain variable region comprising the amino acid sequence of SEQ ID NO: 87. In another related embodiment, the anti-IL-36R antibody consists of a light chain variable region comprising the amino acid sequence of SEQ ID NO: 80; and a heavy chain variable region comprising the amino acid sequence of SEQ ID NO: 88. In another related embodiment, the anti-IL-36R antibody consists of a light chain variable region comprising the amino acid sequence of SEQ ID NO: 80; and a heavy chain variable region comprising the amino acid sequence of SEQ ID NO: 89. In another related embodiment, the anti-IL-36R antibody consists of a light chain comprising an amino acid sequence set forth as SEQ ID NO:118 and a heavy chain comprising an amino acid sequence set forth as SEQ ID NO:125. In another related embodiment, the anti-IL-36R antibody consists of a light chain comprising an amino acid sequence set forth as SEQ ID NO:118 and a heavy chain comprising an amino acid sequence set forth as SEQ ID NO:126. In another related embodiment, the anti-IL-36R antibody consists of a light chain comprising an amino acid sequence set forth as SEQ ID NO:118 and a heavy chain comprising an amino acid sequence set forth as SEQ ID NO:127.

In a second aspect, the present invention relates to a pharmaceutical formulation of a therapeutic anti-IL-36R antibody or antibody fragment (disclosed herein), wherein said formulation comprises: (a) the anti-IL-36R antibody or an antigen binding fragment thereof present at a concentration within the range from about 0.5 mg/mL to about 220 mg/mL and (b) a pharmaceutically acceptable buffer; wherein the formulation is characterized by a pH within the range from about 5 to about 8. In an embodiment relating to this aspect, the buffer is present at a concentration within the range from about 20 mM to about 80 mM. In another embodiment relating to this aspect, the formulation further comprises a pharmaceutically acceptable tonicifying agent.

In a related embodiment, the tonicifying agent is present at a concentration of about 100 mM to about 250 mM. Thus, in one embodiment the pharmaceutical formulation comprises (a) an anti-IL-36R antibody or an antigen binding fragment thereof present at a concentration within the range from about 0.5 mg/mL to about 220 mg/mL; (b) a buffer present at a concentration within the range from about 20 mM to about 80 mM; (c) a tonicifying agent present at a concentration within the range from about 100 mM to about 250 mM; wherein the formulation is characterized by a pH with the range from about 5 to about 8 when in aqueous form.

In an embodiment relating to the second aspect, the pharmaceutical formulation of the present invention comprises a) an anti-IL-36R antibody or an antigen binding fragment thereof as disclosed herein, wherein the antibody or an antigen binding fragment thereof is present at a concentration of about 20 mg/mL, 60 mg/mL or 150 mg/mL; b) an acetate buffer present at a concentration of about 25 to 50 mM; c) sucrose or trehalose present at a concentration of about 150 mM to 200 mM; and optionally d) L-arginine or pharmaceutically acceptable salts thereof present at a concentration of about 25 mM; and/or e) polysorbate 20 or polysorbate 80 present at a concentration of about 0.4 g/L; wherein the formulation is characterized by a pH within the range from about 5 to about 7 when in aqueous form.

In another embodiment relating to the second aspect, the anti-IL-36R antibody or antigen binding fragment thereof is present in the formulation at a concentration within the range from about 0.5 mg/mL to about 220 mg/mL, or a range from about 10 to about 175 mg/mL, or a range from about 10 to about 30 mg/mL, or a range from about 45 to about 75 mg/mL, or a range from about 125 to about 175 mg/mL, or at a concentration of about 15 mg/mL, about 20 mg/mL, about 25 mg/mL, about 30 mg/mL, about 60 mg/mL, about 75 mg/mL, about 80 mg/mL, about 100 mg/mL or about 150 mg/mL. In one embodiment, the anti-IL-36R antibody or antigen binding fragment thereof is present in the formulation at a concentration of about 20 mg/mL. In another embodiment at a concentration of about 60 mg/mL. In yet another embodiment at a concentration of about 150 mg/mL.

In another related embodiment, the pharmaceutically acceptable buffer is present in the formulation at a concentration within the range from about 20 mM to about 80 mM, or a range from about 20 to about 70 mM, or a range from about 20 to about 60 mM, or a range from about 20 mM to about 50 mM, or at a concentration of about 20 mM, about 25 mM, about 35 mM, about 40 mM, about 45 mM, about 50 mM, about 60 mM. The buffer may comprise histidine, phosphate, succinate, citrate, acetate or TRIS. In certain embodiments the buffer is selected from the group consisting of histidine, phosphate, succinate, citrate, acetate and TRIS, particularly acetate and citrate. In one embodiment the buffer is citrate. In another embodiment the buffer is histidine. In yet another embodiment the buffer is acetate.

In another related embodiment, the pharmaceutically acceptable tonicifying agent is present in the formulation at a concentration within the range from about 100 mM to about 250 mM, or a range from about 120 to about 220 mM, or a range from about 130 to about 190 mM, or a range from about 140 to about 190 mM, or at a concentration of about 100 mM, about 120 mM, about 150 mM, about 180 mM, about 200 mM, about 220 mM. The tonicifying agent may be a salt, a sugar or a polyol. In one embodiment the tonicifying agent is one or more sugar and/or a polyol. The tonicifying agent may one or more sugar and/or polyol comprising sucrose, trehalose, sorbitol, glycerol, mannitol or dextrose, particularly sucrose or trehalose. In one embodiment the tonicifying agent is one or more sugar and/or polyol selected from the group consisting of sucrose, trehalose, sorbitol, glycerol, mannitol or dextrose, particularly sucrose and trehalose, particularly the tonicifying agent is sucrose or the tonicifying agent is trehalose.

In another related embodiment, the pharmaceutically acceptable stabilizing agent is present in the formulation at a concentration within the range from about 0 mM to about 80 mM, or a range from about 0 to about 70 mM, or a range from about 0 to about 60 mM, or a range from about 0 to about 50 mM. In case a stabilizing agent is present, it may be present at a concentration within the range from about 5 mM to about 80 mM, or from about 10 mM to 70 mM, or from about 20 mM to 50 mM or at a concentration of about 25 mM, or about 50 mM. The stabilizing agent may comprise an amino acid, such as arginine, histidine, glycine, cysteine, proline, methionine, lysine, aspartate, glutamate or pharmaceutically acceptable salts thereof, more particularly arginine. In one embodiment the stabilizing agent is selected from the group consisting of arginine, histidine, glycine, cysteine, proline, methionine, lysine, aspartate, glutamate and a pharmaceutically acceptable salt thereof. In a specific embodiment the stabilizing agent is L-arginine or a pharmaceutically acceptable salt thereof.

In another related embodiment, the pharmaceutically acceptable salt is present in the formulation at a concentration of within the range from about 0 to about 150 mM, or a range from about 0 to about 120 mM, or a range from about 0 to about 90 mM, or a range from about 0 to about 10 mM, or at a concentration of about 3 mM, 5 mM, 10 mM, 25 mM or 50 mM. In another related embodiment, the pharmaceutically acceptable formulation comprises one or more sugar and/or polyol as a tonicifying agent and further an pharmaceutically acceptable salt at a concentration of within the range from about 3 to about 150 mM, or a range from about 3 to about 120 mM, or a range from about 3 to about 90 mM, or a range from about 3 to about 10 mM, or at a concentration of about 3 mM, 5 mM, 10 mM, 25 mM or 50 mM. The salt may comprise sodium chloride (NaCl), magnesium chloride ($MgCl_2$), magnesium sulfate ($MgSO_4$), potassium chloride (KCl), lithium chloride (LiCl), calcium chloride ($CaCl_2$), boric acid salts or zinc chloride ($ZnCl_2$). In one embodiment the salt is selected from the group consisting of sodium chloride (NaCl), magnesium chloride ($MgCl_2$), magnesium sulfate ($MgSO_4$), potassium chloride (KCl), lithium chloride (LiCl), calcium chloride ($CaCl_2$), boric acid salts and zinc chloride ($ZnCl_2$). In a specific embodiment the salt is sodium chloride.

In another related embodiment, the pharmaceutically acceptable surfactant is present in the formulation at a concentration within a range from about 0 g/L to about 1.5 g/L, a range from about 0.1 g/L to about 1.5 g/L, or a range from about 0.1 to about 1.0 g/L, or a range from about 0.1 to about 0.6 g/L, or a range from about 0.15 to about 0.5 g/L, or at a concentration of about 0.1 g/L, 0.2 g/L, 0.4 g/L, 0.5 g/L or 1 g/L. The surfactant may comprise polysorbate 20, polysorbate 40, polysorbate 60 or polysorbate 80. In one embodiment the surfactant is selected from the group consisting of polysorbate 20, polysorbate 40, polysorbate 60 and polysorbate 80, particularly selected from the group consisting of polysorbate 20 and polysorbate 80.

In an embodiment related to the first aspect, the formulation is characterized by a pH within the range from about 5 to about 8, or a range from about 5 to about 7, or a range from about 5 to about 6.5. In another related embodiment, the pH is about 5, about 5.5, about 6, about 6.5, about 7, about 7.5 or about 8.

In an embodiment related to the second aspect, the anti-IL-36R antibody or antigen binding fragment thereof comprises a light chain variable region comprising the amino acid sequence of SEQ ID NO: 80; and a heavy chain variable region comprising the amino acid sequence of SEQ ID NO: 87; or a light chain variable region comprising the amino acid sequence of SEQ ID NO: 80; and a heavy chain variable region comprising the amino acid sequence of SEQ ID NO: 88; or a light chain variable region comprising the amino acid sequence of SEQ ID NO: 80; and a heavy chain variable region comprising the amino acid sequence of SEQ ID NO: 89. In one embodiment the anti-IL-36R antibody comprises a light chain comprising an amino acid sequence set forth as SEQ ID NO:118 and a heavy chain comprising an amino acid sequence set forth as SEQ ID NO:125; or a light chain comprising an amino acid sequence set forth as SEQ ID NO:118 and a heavy chain comprising an amino acid sequence set forth as SEQ ID NO:126; or a light chain comprising an amino acid sequence set forth as SEQ ID NO:118 and a heavy chain comprising an amino acid sequence set forth as SEQ ID NO:127. In a particular embodiment, the anti-IL-36R antibody comprises a light chain variable region comprising the amino acid sequence of SEQ ID NO: 80; and a heavy chain variable region comprising the amino acid sequence of SEQ ID NO: 89. In another particular embodiment, the anti-IL-36R antibody consists of a light chain comprising an amino acid sequence set forth as SEQ ID NO:118 and a heavy chain comprising an amino acid sequence set forth as SEQ ID NO:127.

In an embodiment related to the second aspect, the anti-IL-36R antibody consists of a light chain variable region comprising the amino acid sequence of SEQ ID NO: 80; and a heavy chain variable region comprising the amino acid sequence of SEQ ID NO: 87. In another related embodiment, the anti-IL-36R antibody consists of a light chain variable region comprising the amino acid sequence of SEQ ID NO: 80; and a heavy chain variable region comprising the amino acid sequence of SEQ ID NO: 88. In another related embodiment, the anti-IL-36R antibody consists of a light chain variable region comprising the amino acid sequence of SEQ ID NO: 80; and a heavy chain variable region comprising the amino acid sequence of SEQ ID NO: 89. In another related embodiment, the anti-IL-36R antibody consists of a light chain comprising an amino acid sequence set forth as SEQ ID NO:118 and a heavy chain comprising an amino acid sequence set forth as SEQ ID NO:125. In another related embodiment, the anti-IL-36R antibody consists of a light chain comprising an amino acid sequence set forth as SEQ ID NO:118 and a heavy chain comprising an amino acid sequence set forth as SEQ ID NO:126. In another related embodiment, the anti-IL-36R antibody consists of a light chain comprising an amino acid sequence set forth as SEQ ID NO:118 and a heavy chain comprising an amino acid sequence set forth as SEQ ID NO:127.

Various other examples or embodiments relating to the first and second aspects of the present invention are described as numbered clauses (1, 2, 3, etc.) below for convenience. These are provided as examples and do not limit the subject technology. It is noted that any of the dependent clauses may be combined in any combination, and placed into a respective independent clause, e.g., clause 1. The other clauses can be presented in a similar manner.

1. A pharmaceutical formulation including:
   a. An anti-IL-36R antibody or an antigen binding fragment thereof, as disclosed herein, present at a concentration within the range from about 0.5 mg/mL to about 220 mg/mL; and
   b. A pharmaceutically acceptable buffer present at a concentration within the range from about 20 mM to about 80 mM;
   wherein the formulation is characterized by a pH within the range from about 5 to about 8 when in aqueous form.
2. The formulation of clause 1, wherein the formulation is in liquid or powder form.
3. The formulation of clause 1 or 2, wherein the anti-IL-36R antibody is present at a concentration of within the range from about 10 mg/mL to about 200 mg/mL.
4. The formulation of clause 1, wherein the anti-IL-36R antibody is present at a concentration of about 20 mg/mL.
5. The formulation of clause 1, wherein the anti-IL-36R antibody is present at a concentration of about 60 mg/mL.
6. The formulation of clause 1, wherein the anti-IL-36R antibody is present at a concentration of about 150 mg/mL.
7. The formulation of any one of clauses 1 to 6, wherein the buffer includes histidine, phosphate, succinate, citrate, acetate or TRIS.
8. The formulation of clause 7, wherein the buffer comprises citrate or acetate.
9. The formulation of clause 7, wherein the buffer comprises histidine.
10. The formulation of clause 8, wherein the buffer comprises acetate.
11. The formulation of any one of clauses 1 to 10, wherein the formulation further comprises a pharmaceutically acceptable tonicifying agent present at a concentration within the range from about 100 mM to about 250 mM.
12. The formulation of clause 11, wherein the tonicifying agent is one or more sugar and/or polyol.
13. The formulation of clause 12, wherein the tonicifying agent is one or more sugar and/or polyol selected from the group consisting of sucrose, trehalose, sorbitol, glycerol, mannitol or dextrose.
14. The formulation of clause 13, wherein the tonicifying agent is sucrose or trehalose.
15. The formulation of clause 14, wherein the tonicifying agent is sucrose.
16. The formulation of clause 14, wherein the tonicifying agent is trehalose.
17. The formulation of any one of clauses 1 to 16, wherein the formulation further comprises a pharmaceutically acceptable stabilizer present at a concentration within the range from about 0 mM to about 80 mM or from about 5 mM to about 80 mM.
18. The formulation of clause 17, wherein the stabilizer comprises an amino acid selected from the group consisting of arginine, histidine, glycine, cysteine, proline, methionine, lysine, aspartate, glutamate or pharmaceutically acceptable salts thereof.
19. The formulation of clause 17, wherein the stabilizer is L-arginine or pharmaceutically acceptable salts thereof.
20. The formulation of any one of clauses 11 to 16, wherein the formulation further comprises a pharmaceutically acceptable salt present at a concentration of within the range from about 0 to about 150 mM.
21. The formulation of clause 20, wherein the salt comprises sodium chloride (NaCl), magnesium chloride ($MgCl_2$), magnesium sulfate ($MgSO_4$), potassium chloride (KCl), lithium chloride (LiCl), calcium chloride (CaCl$_2$)), boric acid salts or zinc chloride (ZnCl$_2$).

22. The formulation of clause 20, wherein the salt is sodium chloride (NaCl).

23. The formulation of any one of clauses 1 to 22, wherein the formulation further comprises a pharmaceutically acceptable surfactant present at a concentration within the range from about 0.1 g/L to about 1.5 g/L.

24. The formulation of clause 23, wherein the surfactant comprises poloxamer 188, polysorbate 20, polysorbate 40, polysorbate 60 or polysorbate 80.

25. The formulation of clause 23, wherein the surfactant is selected from the group consisting of polysorbate 20, polysorbate 40, polysorbate 60 or polysorbate 80.

26. The formulation of clause 23, wherein the surfactant is polysorbate 20.

27. The formulation of clause 23, wherein the surfactant is polysorbate 80.

28. A pharmaceutical formulation including:
    a. an anti-IL-36R antibody or an antigen binding fragment thereof, as disclosed herein, present at a concentration within the range from about 10 mg/mL to about 200 mg/mL;
    b. an acetate and/or histidine buffer present at a concentration within the range from about 20 mM to about 80 mM;
    c. sucrose and/or trehalose present at a concentration within the range from about 100 mM to about 250 mM;
    d. L-arginine and/or pharmaceutically acceptable salts thereof present at a concentration within the range from about 0 mM to about 80 mM;
    e. sodium chloride (NaCl) present at a concentration of within the range from about 0 to about 150 mM; and
    f. polysorbate 20 and/or polysorbate 80 present at a concentration within the range from about 0 g/L to about 1.5 g/L or from about 0.1 g/L to about 1.5 g/L;
    wherein the formulation is characterized by a pH within the range from about 5 to about 7 when in aqueous form.

29. A pharmaceutical formulation including:
    a. an anti-IL-36R antibody or an antigen binding fragment thereof, as disclosed herein, present at a concentration of about 20 mg/mL;
    b. an citrate buffer present at a concentration at a concentration of about 25 mM;
    c. sucrose and/or trehalose present at a concentration of about 200 mM;
    d. polysorbate 80 present at a concentration of about 0.4 g/L; wherein the formulation is characterized by a pH within the range from about 6 to about 7 when in aqueous form.

30. A pharmaceutical formulation including:
    a. an anti-IL-36R antibody or an antigen binding fragment thereof, as disclosed herein, present at a concentration of about 60 mg/mL;
    b. an acetate buffer present at a concentration at a concentration of about 45 mM;
    c. sucrose and/or trehalose present at a concentration of about 150 mM;
    d. L-arginine or pharmaceutically acceptable salts thereof present at a concentration of about 25 mM; and
    e. polysorbate 20 present at a concentration of about 0.4 g/L;
    wherein the formulation is characterized by a pH within the range from about 5 to about 6 when in aqueous form.

31. A pharmaceutical formulation including:
    a. an anti-IL-36R antibody or an antigen binding fragment thereof, as disclosed herein, present at a concentration of about 150 mg/mL;
    b. an acetate buffer present at a concentration at a concentration of about 45 mM;
    c. sucrose or trehalose present at a concentration of about 150 mM;
    d. L-arginine or pharmaceutically acceptable salts thereof present at a concentration of about 25 mM; and
    e. polysorbate 20 present at a concentration of about 0.4 g/L; wherein the formulation is characterized by a pH within the range from about 5 to about 6 when in aqueous form.

32. The pharmaceutical formulation of any one of clauses 1-31, wherein the formulation is characterized by an osmolality within the range from about 210 mOsmol/kg to about 390 mOsm/kg.

33. The pharmaceutical formulation of any one of clauses 1-32, wherein less than about 5% of the antibody is present in an aggregate form in the formulation.

34. The pharmaceutical formulation of any one of clauses 1-33, wherein the formulation is sterile.

35. The pharmaceutical formulation of any one of clauses 1-34, wherein the formulation is stable upon freezing and thawing.

36. The pharmaceutical formulation of any of clauses 1-35, wherein the formulation comprises water or is reconstituted with water.

37. The pharmaceutical formulation of any of clauses 1-36, wherein the formulation has a pH of between about 5 to about 6 in liquid form or when reconstituted with water.

38. The pharmaceutical formulation of any of clauses 1-37, wherein the formulation has a pH of about 6 in liquid or when reconstituted with water.

39. The pharmaceutical formulation of any of clauses 1-37, wherein the formulation has at least one feature selected from the group consisting of:
    (i) Increased shelf life
    (ii) better temperature stability,
    (iii) decreased formation of aggregates,
    (iv) better chemical stability,
    (v) decreased viscosity, and as compared to a reference formulation.

40. The pharmaceutical formulation of any of clauses 1-37, wherein the formulation having at least one feature selected from the group consisting of:
    (a) decreased percentage of aggregates as measured by High Performance Size Exclusion Chromatography (HP-SEC),
    (b) higher percentage of monomers as measured by HP-SEC,
    (c) higher percentage of main peak (less degradation of charge variants) measured by CEX,
    (d) lower percentage of subvisual particles such as ≥10 μm and ≥25 μm, and
    (e) lower turbidity value in Formazine Nephelometry Units (FNU), after storage at about 40° C. as compared to the reference formulation.

41. A pharmaceutical formulation comprising:
    an anti-IL-36R antibody or antigen-binding fragment thereof, comprising:
    i. a light chain comprising an amino acid sequence set forth as SEQ ID NO:118 and a heavy chain comprising an amino acid sequence set forth as SEQ ID NO:125; or ii. a light chain comprising an amino acid sequence set forth as SEQ ID NO:118 and a heavy chain comprising an amino acid sequence set forth as SEQ ID NO:126; or
iii. a light chain comprising an amino acid sequence set forth as SEQ ID NO:118 and a heavy chain comprising an amino acid sequence set forth as SEQ ID NO:127;
wherein the formulation is selected from the group consisting of:
I. formulation comprising about 20 mg/mL of the anti-IL-36R antibody, about 40 mM histidine, about 120 mM sucrose, about 50 mM L-Arginine, about 5 mM NaCl and about 1.0 g/L Polysorbate 20, with a pH of about 6.0;
II. formulation comprising about 60 mg/mL of the anti-IL-36R antibody, about 45 mM acetate, about 150 mM sucrose, about 25 mM L-Arginine, about 0.4 g/L Polysorbate 20, with a pH of about 5.5;
III. formulation comprising about 20 mg/mL of the anti-IL-36R antibody, about 45 mM acetate, about 180 mM sucrose, about 25 mM Glycine, about 0.4 g/L Polysorbate 80, with a pH of about 5.5;
IV. formulation comprising about 150 mg/mL of the anti-IL-36R antibody, about 25 mM citrate, about 150 mM trehalose, about 25 mM methionine, about 0.2 g/L Polysorbate 20, with a pH of about 6.0;
V. formulation comprising about 60 mg/mL of the anti-IL-36R antibody, about 25 mM histidine, about 160 mM sucrose, about 20 mM mannitol, about 0.2 g/L Polysorbate 20, with a pH of about 6.0;
VI. formulation comprising about 20 mg/mL of the anti-IL-36R antibody, about 25 mM citrate, about 200 mM sucrose, about 0.4 g/L Polysorbate 80, with a pH of about 6.5;
VII. formulation comprising about 150 mg/mL of the anti-IL-36R antibody, about 45 mM acetate, about 150 mM sucrose, about 25 mM L-Arginine, about 0.4 g/L Polysorbate 20, with a pH of about 5.5;
VIII. formulation comprising about 15 mg/mL of the anti-IL-36R antibody, about 35 mM histidine, about 180 mM trehalose, about 25 mM L-Arginine, about 3 mM NaCl, about 0.4 g/L Polysorbate 80, with a pH of about 6.0;
IX. formulation comprising about 80 mg/mL of the anti-IL-36R antibody, about 25 mM acetate, about 100 mM mannitol, about 50 mM NaCl, about 0.2 g/L Polysorbate 20, with a pH of about 5.5; and
X. formulation comprising about 100 mg/mL of the anti-IL-36R antibody, about 20 mM succinate, about 220 mM sucrose, about 0.1 g/L Polysorbate 80, with a pH of about 6.0

42. A pharmaceutical formulation comprising:
an anti-IL-36R antibody or antigen-binding fragment thereof, comprising:
i. a light chain comprising an amino acid sequence set forth as SEQ ID NO:118 and a heavy chain comprising an amino acid sequence set forth as SEQ ID NO:125; or
ii. a light chain comprising an amino acid sequence set forth as SEQ ID NO:118 and a heavy chain comprising an amino acid sequence set forth as SEQ ID NO:126; or
iii. a light chain comprising an amino acid sequence set forth as SEQ ID NO:118 and a heavy chain comprising an amino acid sequence set forth as SEQ ID NO:127;
wherein the formulation includes about 20 mg/mL of the anti-IL-36R antibody, about 40 mM histidine, about 120 mM sucrose, about 50 mM L-Arginine, about 5 mM NaCl and about 1.0 g/L Polysorbate 20, with a pH of about 6.0.

43. A pharmaceutical formulation comprising:
an anti-IL-36R antibody or antigen-binding fragment thereof, comprising:
i. a light chain comprising an amino acid sequence set forth as SEQ ID NO:118 and a heavy chain comprising an amino acid sequence set forth as SEQ ID NO:125; or
ii. a light chain comprising an amino acid sequence set forth as SEQ ID NO:118 and a heavy chain comprising an amino acid sequence set forth as SEQ ID NO:126; or
iii. a light chain comprising an amino acid sequence set forth as SEQ ID NO:118 and a heavy chain comprising an amino acid sequence set forth as SEQ ID NO:127;
wherein the formulation includes about 60 mg/mL of the anti-IL-36R antibody, about 45 mM acetate, about 150 mM sucrose, about 25 mM L-Arginine, about 0.4 g/L Polysorbate 20, with a pH of about 5.5.

44. A pharmaceutical formulation comprising:
an anti-IL-36R antibody or antigen-binding fragment thereof, comprising:
i. a light chain comprising an amino acid sequence set forth as SEQ ID NO:118 and a heavy chain comprising an amino acid sequence set forth as SEQ ID NO:125; or
ii. a light chain comprising an amino acid sequence set forth as SEQ ID NO:118 and a heavy chain comprising an amino acid sequence set forth as SEQ ID NO:126; or
iii. a light chain comprising an amino acid sequence set forth as SEQ ID NO:118 and a heavy chain comprising an amino acid sequence set forth as SEQ ID NO:127;
wherein the formulation includes about 20 mg/mL of the anti-IL-36R antibody, about 45 mM acetate, about 180 mM sucrose, about 25 mM Glycine, about 0.4 g/L Polysorbate 80, with a pH of about 5.5.

45. A pharmaceutical formulation comprising:
an anti-IL-36R antibody or antigen-binding fragment thereof, comprising:
i. a light chain comprising an amino acid sequence set forth as SEQ ID NO:118 and a heavy chain comprising an amino acid sequence set forth as SEQ ID NO:125; or
ii. a light chain comprising an amino acid sequence set forth as SEQ ID NO:118 and a heavy chain comprising an amino acid sequence set forth as SEQ ID NO:126; or iii. a light chain comprising an amino acid sequence set forth as SEQ ID NO:118 and a heavy chain comprising an amino acid sequence set forth as SEQ ID NO:127;
   wherein the formulation includes about 150 mg/mL of the anti-IL-36R antibody, about 25 mM citrate, about 150 mM trehalose, about 25 mM methionine, about 0.2 g/L Polysorbate 20, with a pH of about 6.0.

46. A pharmaceutical formulation comprising:
   an anti-IL-36R antibody or antigen-binding fragment thereof, comprising:
   i. a light chain comprising an amino acid sequence set forth as SEQ ID NO:118 and a heavy chain comprising an amino acid sequence set forth as SEQ ID NO:125; or
   ii. a light chain comprising an amino acid sequence set forth as SEQ ID NO:118 and a heavy chain comprising an amino acid sequence set forth as SEQ ID NO:126; or
   iii. a light chain comprising an amino acid sequence set forth as SEQ ID NO:118 and a heavy chain comprising an amino acid sequence set forth as SEQ ID NO:127;
      wherein the formulation includes about 60 mg/mL of the anti-IL-36R antibody, about 25 mM histidine, about 160 mM sucrose, about 20 mM mannitol, about 0.2 g/L Polysorbate 20, with a pH of about 6.0.

47. A pharmaceutical formulation comprising:
   an anti-IL-36R antibody or antigen-binding fragment thereof, comprising:
   i. a light chain comprising an amino acid sequence set forth as SEQ ID NO:118 and a heavy chain comprising an amino acid sequence set forth as SEQ ID NO:125; or
   ii. a light chain comprising an amino acid sequence set forth as SEQ ID NO:118 and a heavy chain comprising an amino acid sequence set forth as SEQ ID NO:126; or
   iii. a light chain comprising an amino acid sequence set forth as SEQ ID NO:118 and a heavy chain comprising an amino acid sequence set forth as SEQ ID NO:127;
      wherein the formulation includes about 20 mg/mL of the anti-IL-36R antibody, about 25 mM citrate, about 200 mM sucrose, about 0.4 g/L Polysorbate 80, with a pH of about 6.5.

48. A pharmaceutical formulation comprising:
   an anti-IL-36R antibody or antigen-binding fragment thereof, comprising:
   i. a light chain comprising an amino acid sequence set forth as SEQ ID NO:118 and a heavy chain comprising an amino acid sequence set forth as SEQ ID NO:125; or
   ii. a light chain comprising an amino acid sequence set forth as SEQ ID NO:118 and a heavy chain comprising an amino acid sequence set forth as SEQ ID NO:126; or
   iii. a light chain comprising an amino acid sequence set forth as SEQ ID NO:118 and a heavy chain comprising an amino acid sequence set forth as SEQ ID NO:127;
      wherein the formulation includes about 150 mg/mL of the anti-IL-36R antibody, about 45 mM acetate, about 150 mM sucrose, about 25 mM L-Arginine, about 0.4 g/L Polysorbate 20, with a pH of about 5.5.

49. A pharmaceutical formulation comprising:
   an anti-IL-36R antibody or antigen-binding fragment thereof, comprising:
   i. a light chain comprising an amino acid sequence set forth as SEQ ID NO:118 and a heavy chain comprising an amino acid sequence set forth as SEQ ID NO:125; or
   ii. a light chain comprising an amino acid sequence set forth as SEQ ID NO:118 and a heavy chain comprising an amino acid sequence set forth as SEQ ID NO:126; or
   iii. a light chain comprising an amino acid sequence set forth as SEQ ID NO:118 and a heavy chain comprising an amino acid sequence set forth as SEQ ID NO:127;
      wherein the formulation includes about 15 mg/mL of the anti-IL-36R antibody, about 35 mM histidine, about 180 mM trehalose, about 25 mM L-Arginine, about 3 mM NaCl, about 0.4 g/L Polysorbate 80, with a pH of about 6.0.

50. A pharmaceutical formulation comprising:
   an anti-IL-36R antibody or antigen-binding fragment thereof, comprising:
   i. a light chain comprising an amino acid sequence set forth as SEQ ID NO:118 and a heavy chain comprising an amino acid sequence set forth as SEQ ID NO:125; or
   ii. a light chain comprising an amino acid sequence set forth as SEQ ID NO:118 and a heavy chain comprising an amino acid sequence set forth as SEQ ID NO:126; or
   iii. a light chain comprising an amino acid sequence set forth as SEQ ID NO:118 and a heavy chain comprising an amino acid sequence set forth as SEQ ID NO:127;
      wherein the formulation includes about 80 mg/mL of the anti-IL-36R antibody, about 25 mM acetate, about 100 mM mannitol, about 50 mM NaCl, about 0.2 g/L Polysorbate 20, with a pH of about 5.5.

51. A pharmaceutical formulation comprising:
   an anti-IL-36R antibody or antigen-binding fragment thereof, comprising:
   i. a light chain comprising an amino acid sequence set forth as SEQ ID NO:118 and a heavy chain comprising an amino acid sequence set forth as SEQ ID NO:125; or
   ii. a light chain comprising an amino acid sequence set forth as SEQ ID NO:118 and a heavy chain comprising an amino acid sequence set forth as SEQ ID NO:126; or
   iii. a light chain comprising an amino acid sequence set forth as SEQ ID NO:118 and a heavy chain comprising an amino acid sequence set forth as SEQ ID NO:127;
      wherein the formulation includes about 100 mg/mL of the anti-IL-36R antibody, about 20 mM succinate, about 220 mM sucrose, about 0.1 g/L Polysorbate 80, with a pH of about 6.0.

52. A pharmaceutical formulation comprising:
  an anti-IL-36R antibody or antigen-binding fragment thereof, comprising:
    i. a light chain comprising an amino acid sequence set forth as SEQ ID NO:118 and a heavy chain comprising an amino acid sequence set forth as SEQ ID NO:125; or
    ii. a light chain comprising an amino acid sequence set forth as SEQ ID NO:118 and a heavy chain comprising an amino acid sequence set forth as SEQ ID NO:127;
      wherein the formulation includes: about 60 mg/mL of the anti-IL-36R antibody, about 45 mM acetate, about 150 mM sucrose, about 25 mM L-Arginine, about 0.4 g/L Polysorbate 20, with a pH of about 5.5.

53. A pharmaceutical formulation comprising:
  an anti-IL-36R antibody or antigen-binding fragment thereof, comprising:
  a light chain variable region comprising the amino acid sequence of SEQ ID NO: 77; and a heavy chain variable region comprising the amino acid sequence of SEQ ID NO: 87; or
  a light chain variable region comprising the amino acid sequence of SEQ ID NO: 77; and a heavy chain variable region comprising the amino acid sequence of SEQ ID NO: 88; or
  a light chain variable region comprising the amino acid sequence of SEQ ID NO: 77; and a heavy chain variable region comprising the amino acid sequence of SEQ ID NO: 89; or
  a light chain variable region comprising the amino acid sequence of SEQ ID NO: 80; and a heavy chain variable region comprising the amino acid sequence of SEQ ID NO: 87; or
  a light chain variable region comprising the amino acid sequence of SEQ ID NO: 80; and a heavy chain variable region comprising the amino acid sequence of SEQ ID NO: 88; or
  a light chain variable region comprising the amino acid sequence of SEQ ID NO: 80; and a heavy chain variable region comprising the amino acid sequence of SEQ ID NO: 89;
  wherein the formulation includes: about 20 mg/mL of the anti-IL-36R antibody, about 40 mM histidine, about 120 mM sucrose, about 50 mM L-Arginine, about 5 mM NaCl and about 1.0 g/L Polysorbate 20, with a pH of about 6.0.

54. A pharmaceutical formulation comprising:
  an anti-IL-36R antibody or antigen-binding fragment thereof, comprising:
  a light chain variable region comprising the amino acid sequence of SEQ ID NO: 77; and a heavy chain variable region comprising the amino acid sequence of SEQ ID NO: 87; or
  a light chain variable region comprising the amino acid sequence of SEQ ID NO: 77; and a heavy chain variable region comprising the amino acid sequence of SEQ ID NO: 88; or
  a light chain variable region comprising the amino acid sequence of SEQ ID NO: 77; and a heavy chain variable region comprising the amino acid sequence of SEQ ID NO: 89; or
  a light chain variable region comprising the amino acid sequence of SEQ ID NO: 80; and a heavy chain variable region comprising the amino acid sequence of SEQ ID NO: 87; or
  a light chain variable region comprising the amino acid sequence of SEQ ID NO: 80; and a heavy chain variable region comprising the amino acid sequence of SEQ ID NO: 88; or
  a light chain variable region comprising the amino acid sequence of SEQ ID NO: 80; and a heavy chain variable region comprising the amino acid sequence of SEQ ID NO: 89;
  wherein the formulation includes: about 60 mg/mL of the anti-IL-36R antibody, about 45 mM acetate, about 150 mM sucrose, about 25 mM L-Arginine, about 0.4 g/L Polysorbate 20, with a pH of about 5.5.

55. A pharmaceutical formulation comprising:
  an anti-IL-36R antibody or antigen-binding fragment thereof, comprising:
  a light chain variable region comprising the amino acid sequence of SEQ ID NO: 77; and a heavy chain variable region comprising the amino acid sequence of SEQ ID NO: 87; or
  a light chain variable region comprising the amino acid sequence of SEQ ID NO: 77; and a heavy chain variable region comprising the amino acid sequence of SEQ ID NO: 88; or
  a light chain variable region comprising the amino acid sequence of SEQ ID NO: 77; and a heavy chain variable region comprising the amino acid sequence of SEQ ID NO: 89; or
  a light chain variable region comprising the amino acid sequence of SEQ ID NO: 80; and a heavy chain variable region comprising the amino acid sequence of SEQ ID NO: 87; or
  a light chain variable region comprising the amino acid sequence of SEQ ID NO: 80; and a heavy chain variable region comprising the amino acid sequence of SEQ ID NO: 88; or
  a light chain variable region comprising the amino acid sequence of SEQ ID NO: 80; and a heavy chain variable region comprising the amino acid sequence of SEQ ID NO: 89;
  wherein the formulation includes: about 20 mg/mL of the anti-IL-36R antibody, about 45 mM acetate, about 180 mM sucrose, about 25 mM Glycine, about 0.4 g/L Polysorbate 80, with a pH of about 5.5.

56. A pharmaceutical formulation comprising:
  an anti-IL-36R antibody or antigen-binding fragment thereof, comprising:
  a light chain variable region comprising the amino acid sequence of SEQ ID NO: 77; and a heavy chain variable region comprising the amino acid sequence of SEQ ID NO: 87; or
  a light chain variable region comprising the amino acid sequence of SEQ ID NO: 77; and a heavy chain variable region comprising the amino acid sequence of SEQ ID NO: 88; or
  a light chain variable region comprising the amino acid sequence of SEQ ID NO: 77; and a heavy chain variable region comprising the amino acid sequence of SEQ ID NO: 89; or
  a light chain variable region comprising the amino acid sequence of SEQ ID NO: 80; and a heavy chain variable region comprising the amino acid sequence of SEQ ID NO: 87; or
  a light chain variable region comprising the amino acid sequence of SEQ ID NO: 80; and a heavy chain variable region comprising the amino acid sequence of SEQ ID NO: 88; or a light chain variable region comprising the amino acid sequence of SEQ ID NO: 80; and a heavy chain variable region comprising the amino acid sequence of SEQ ID NO: 89;

wherein the formulation includes: about 150 mg/mL of the anti-IL-36R antibody, about 25 mM citrate, about 150 mM trehalose, about 25 mM methionine, about 0.2 g/L Polysorbate 20, with a pH of about 6.0.

57. A pharmaceutical formulation comprising:
an anti-IL-36R antibody or antigen-binding fragment thereof, comprising:
a light chain variable region comprising the amino acid sequence of SEQ ID NO: 77; and a heavy chain variable region comprising the amino acid sequence of SEQ ID NO: 87; or
a light chain variable region comprising the amino acid sequence of SEQ ID NO: 77; and a heavy chain variable region comprising the amino acid sequence of SEQ ID NO: 88; or
a light chain variable region comprising the amino acid sequence of SEQ ID NO: 77; and a heavy chain variable region comprising the amino acid sequence of SEQ ID NO: 89; or
a light chain variable region comprising the amino acid sequence of SEQ ID NO: 80; and a heavy chain variable region comprising the amino acid sequence of SEQ ID NO: 87; or
a light chain variable region comprising the amino acid sequence of SEQ ID NO: 80; and a heavy chain variable region comprising the amino acid sequence of SEQ ID NO: 88; or
a light chain variable region comprising the amino acid sequence of SEQ ID NO: 80; and a heavy chain variable region comprising the amino acid sequence of SEQ ID NO: 89;
wherein the formulation includes: about 60 mg/mL of the anti-IL-36R antibody, about 25 mM histidine, about 160 mM sucrose, about 20 mM mannitol, about 0.2 g/L Polysorbate 20, with a pH of about 6.0.

58. A pharmaceutical formulation comprising:
an anti-IL-36R antibody or antigen-binding fragment thereof, comprising:
a light chain variable region comprising the amino acid sequence of SEQ ID NO: 77; and a heavy chain variable region comprising the amino acid sequence of SEQ ID NO: 87; or
a light chain variable region comprising the amino acid sequence of SEQ ID NO: 77; and a heavy chain variable region comprising the amino acid sequence of SEQ ID NO: 88; or
a light chain variable region comprising the amino acid sequence of SEQ ID NO: 77; and a heavy chain variable region comprising the amino acid sequence of SEQ ID NO: 89; or
a light chain variable region comprising the amino acid sequence of SEQ ID NO: 80; and a heavy chain variable region comprising the amino acid sequence of SEQ ID NO: 87; or
a light chain variable region comprising the amino acid sequence of SEQ ID NO: 80; and a heavy chain variable region comprising the amino acid sequence of SEQ ID NO: 88; or
a light chain variable region comprising the amino acid sequence of SEQ ID NO: 80; and a heavy chain variable region comprising the amino acid sequence of SEQ ID NO: 89;
wherein the formulation includes: about 20 mg/mL of the anti-IL-36R antibody, about 25 mM citrate, about 200 mM sucrose, about 0.4 g/L Polysorbate 80, with a pH of about 6.5.

59. A pharmaceutical formulation comprising:
an anti-IL-36R antibody or antigen-binding fragment thereof, comprising:
a light chain variable region comprising the amino acid sequence of SEQ ID NO: 77; and a heavy chain variable region comprising the amino acid sequence of SEQ ID NO: 87; or
a light chain variable region comprising the amino acid sequence of SEQ ID NO: 77; and a heavy chain variable region comprising the amino acid sequence of SEQ ID NO: 88; or
a light chain variable region comprising the amino acid sequence of SEQ ID NO: 77; and a heavy chain variable region comprising the amino acid sequence of SEQ ID NO: 89; or
a light chain variable region comprising the amino acid sequence of SEQ ID NO: 80; and a heavy chain variable region comprising the amino acid sequence of SEQ ID NO: 87; or
a light chain variable region comprising the amino acid sequence of SEQ ID NO: 80; and a heavy chain variable region comprising the amino acid sequence of SEQ ID NO: 88; or
a light chain variable region comprising the amino acid sequence of SEQ ID NO: 80; and a heavy chain variable region comprising the amino acid sequence of SEQ ID NO: 89;
wherein the formulation includes: about 150 mg/mL of the anti-IL-36R antibody, about 45 mM acetate, about 150 mM sucrose, about 25 mM L-Arginine, about 0.4 g/L Polysorbate 20, with a pH of about 5.5.

60. A pharmaceutical formulation comprising:
an anti-IL-36R antibody or antigen-binding fragment thereof, comprising:
a light chain variable region comprising the amino acid sequence of SEQ ID NO: 77; and a heavy chain variable region comprising the amino acid sequence of SEQ ID NO: 87; or
a light chain variable region comprising the amino acid sequence of SEQ ID NO: 77; and a heavy chain variable region comprising the amino acid sequence of SEQ ID NO: 88; or
a light chain variable region comprising the amino acid sequence of SEQ ID NO: 77; and a heavy chain variable region comprising the amino acid sequence of SEQ ID NO: 89; or
a light chain variable region comprising the amino acid sequence of SEQ ID NO: 80; and a heavy chain variable region comprising the amino acid sequence of SEQ ID NO: 87; or
a light chain variable region comprising the amino acid sequence of SEQ ID NO: 80; and a heavy chain variable region comprising the amino acid sequence of SEQ ID NO: 88; or
a light chain variable region comprising the amino acid sequence of SEQ ID NO: 80; and a heavy chain variable region comprising the amino acid sequence of SEQ ID NO: 89;
wherein the formulation includes: about 15 mg/mL of the anti-IL-36R antibody, about 35 mM histidine, about 180 mM trehalose, about 25 mM L-Arginine, about 3 mM NaCl, about 0.4 g/L Polysorbate 80, with a pH of about 6.0.

61. A pharmaceutical formulation comprising:
an anti-IL-36R antibody or antigen-binding fragment thereof, comprising:
a light chain variable region comprising the amino acid sequence of SEQ ID NO: 77; and a heavy chain variable region comprising the amino acid sequence of SEQ ID NO: 87; or
a light chain variable region comprising the amino acid sequence of SEQ ID NO: 77; and a heavy chain variable region comprising the amino acid sequence of SEQ ID NO: 88; or
a light chain variable region comprising the amino acid sequence of SEQ ID NO: 77; and a heavy chain variable region comprising the amino acid sequence of SEQ ID NO: 89; or
a light chain variable region comprising the amino acid sequence of SEQ ID NO: 80; and a heavy chain variable region comprising the amino acid sequence of SEQ ID NO: 87; or
a light chain variable region comprising the amino acid sequence of SEQ ID NO: 80; and a heavy chain variable region comprising the amino acid sequence of SEQ ID NO: 88; or
a light chain variable region comprising the amino acid sequence of SEQ ID NO: 80; and a heavy chain variable region comprising the amino acid sequence of SEQ ID NO: 89;
wherein the formulation includes: about 80 mg/mL of the anti-IL-36R antibody, about 25 mM acetate, about 100 mM mannitol, about 50 mM NaCl, about 0.2 g/L Polysorbate 20, with a pH of about 5.5.

62. A pharmaceutical formulation comprising:
an anti-IL-36R antibody or antigen-binding fragment thereof, comprising:
a light chain variable region comprising the amino acid sequence of SEQ ID NO: 77; and a heavy chain variable region comprising the amino acid sequence of SEQ ID NO: 87; or
a light chain variable region comprising the amino acid sequence of SEQ ID NO: 77; and a heavy chain variable region comprising the amino acid sequence of SEQ ID NO: 88; or
a light chain variable region comprising the amino acid sequence of SEQ ID NO: 77; and a heavy chain variable region comprising the amino acid sequence of SEQ ID NO: 89; or
a light chain variable region comprising the amino acid sequence of SEQ ID NO: 80; and a heavy chain variable region comprising the amino acid sequence of SEQ ID NO: 87; or
a light chain variable region comprising the amino acid sequence of SEQ ID NO: 80; and a heavy chain variable region comprising the amino acid sequence of SEQ ID NO: 88; or
a light chain variable region comprising the amino acid sequence of SEQ ID NO: 80; and a heavy chain variable region comprising the amino acid sequence of SEQ ID NO: 89;
wherein the formulation includes: about 100 mg/mL of the anti-IL-36R antibody, about 20 mM succinate, about 220 mM sucrose, about 0.1 g/L Polysorbate 80, with a pH of about 6.0.

63. A pharmaceutical formulation comprising:
an anti-IL-36R antibody or antigen-binding fragment thereof, comprising:
a light chain variable region comprising the amino acid sequence of SEQ ID NO: 77; and a heavy chain variable region comprising the amino acid sequence of SEQ ID NO: 87; or
a light chain variable region comprising the amino acid sequence of SEQ ID NO: 80; and a heavy chain variable region comprising the amino acid sequence of SEQ ID NO: 89;
wherein the formulation includes: about 60 mg/mL of the anti-IL-36R antibody, about 45 mM acetate, about 150 mM sucrose, about 25 mM L-Arginine, about 0.4 g/L Polysorbate 20, with a pH of about 5.5.

64. A pharmaceutical formulation comprising:
an anti-IL-36R antibody or antigen-binding fragment thereof, comprising:
i. a light chain comprising an amino acid sequence set forth as SEQ ID NO:118 and a heavy chain comprising an amino acid sequence set forth as SEQ ID NO:125; or
ii. a light chain comprising an amino acid sequence set forth as SEQ ID NO:118 and a heavy chain comprising an amino acid sequence set forth as SEQ ID NO:126; or
iii. a light chain comprising an amino acid sequence set forth as SEQ ID NO:118 and a heavy chain comprising an amino acid sequence set forth as SEQ ID NO:127;
wherein the formulation is selected from the group consisting of:
I. formulation comprising about 20 mg/mL to about 150 mg/mL of the anti-IL-36R antibody, about 40 mM histidine, about 120 mM sucrose, about 50 mM L-Arginine, about 5 mM NaCl and about 1.0 g/L Polysorbate 20, with a pH of about 6.0;
II. formulation comprising about 20 mg/mL to about 150 mg/mL of the anti-IL-36R antibody, about 45 mM acetate, about 150 mM sucrose, about 25 mM L-Arginine, about 0.4 g/L Polysorbate 20, with a pH of about 5.5;
III. formulation comprising about 20 mg/mL to about 150 mg/mL of the anti-IL-36R antibody, about 45 mM acetate, about 180 mM sucrose, about 25 mM Glycine, about 0.4 g/L Polysorbate 80, with a pH of about 5.5;
IV. formulation comprising about 20 mg/mL to about 150 mg/mL of the anti-IL-36R antibody, about 25 mM citrate, about 150 mM trehalose, about 25 mM methionine, about 0.2 g/L Polysorbate 20, with a pH of about 6.0;
V. formulation comprising about 20 mg/mL to about 150 mg/mL of the anti-IL-36R antibody, about 25 mM histidine, about 160 mM sucrose, about 20 mM mannitol, about 0.2 g/L Polysorbate 20, with a pH of about 6.0;
VI. formulation comprising about 20 mg/mL to about 150 mg/mL of the anti-IL-36R antibody, about 25 mM citrate, about 200 mM sucrose, about 0.4 g/L Polysorbate 80, with a pH of about 6.5;
VII. formulation comprising about 20 mg/mL to about 150 mg/mL of the anti-IL-36R antibody, about 45 mM acetate, about 150 mM sucrose, about 25 mM L-Arginine, about 0.4 g/L Polysorbate 20, with a pH of about 5.5;

VIII. formulation comprising about 20 mg/mL to about 150 mg/mL of the anti-IL-36R antibody, about 35 mM histidine, about 180 mM trehalose, about 25 mM L-Arginine, about 3 mM NaCl, about 0.4 g/L Polysorbate 80, with a pH of about 6.0;

IX. formulation comprising about 20 mg/mL to about 150 mg/mL of the anti-IL-36R antibody, about 25 mM acetate, about 100 mM mannitol, about 50 mM NaCl, about 0.2 g/L Polysorbate 20, with a pH of about 5.5; and X. formulation comprising about 20 mg/mL to about 150 mg/mL of the anti-IL-36R antibody, about 20 mM succinate, about 220 mM sucrose, about 0.1 g/L Polysorbate 80, with a pH of about 6.0.

65. A pharmaceutical formulation comprising:

an anti-IL-36R antibody or antigen-binding fragment thereof, comprising:

a light chain variable region comprising the amino acid sequence of SEQ ID NO: 77; and a heavy chain variable region comprising the amino acid sequence of SEQ ID NO: 87; or a light chain variable region comprising the amino acid sequence of SEQ ID NO: 77; and a heavy chain variable region comprising the amino acid sequence of SEQ ID NO: 88; or a light chain variable region comprising the amino acid sequence of SEQ ID NO: 77; and a heavy chain variable region comprising the amino acid sequence of SEQ ID NO: 89; or a light chain variable region comprising the amino acid sequence of SEQ ID NO: 80; and a heavy chain variable region comprising the amino acid sequence of SEQ ID NO: 87; or a light chain variable region comprising the amino acid sequence of SEQ ID NO: 80; and a heavy chain variable region comprising the amino acid sequence of SEQ ID NO: 88; or a light chain variable region comprising the amino acid sequence of SEQ ID NO: 80; and a heavy chain variable region comprising the amino acid sequence of SEQ ID NO: 89;

wherein the formulation is selected from the group consisting of:

I. formulation comprising about 20 mg/mL to about 150 mg/mL of the anti-IL-36R antibody, about 40 mM histidine, about 120 mM sucrose, about 50 mM L-Arginine, about 5 mM NaCl and about 1.0 g/L Polysorbate 20, with a pH of about 6.0;

II. formulation comprising about 20 mg/mL to about 150 mg/mL of the anti-IL-36R antibody, about 45 mM acetate, about 150 mM sucrose, about 25 mM L-Arginine, about 0.4 g/L Polysorbate 20, with a pH of about 5.5;

III. formulation comprising about 20 mg/mL to about 150 mg/mL of the anti-IL-36R antibody, about 45 mM acetate, about 180 mM sucrose, about 25 mM Glycine, about 0.4 g/L Polysorbate 80, with a pH of about 5.5;

IV. formulation comprising about 20 mg/mL to about 150 mg/mL of the anti-IL-36R antibody, about 25 mM citrate, about 150 mM trehalose, about 25 mM methionine, about 0.2 g/L Polysorbate 20, with a pH of about 6.0;

V. formulation comprising about 20 mg/mL to about 150 mg/mL of the anti-IL-36R antibody, about 25 mM histidine, about 160 mM sucrose, about 20 mM mannitol, about 0.2 g/L Polysorbate 20, with a pH of about 6.0;

VI. formulation comprising about 20 mg/mL to about 150 mg/mL of the anti-IL-36R antibody, about 25 mM citrate, about 200 mM sucrose, about 0.4 g/L Polysorbate 80, with a pH of about 6.5;

VII. formulation comprising about 20 mg/mL to about 150 mg/mL of the anti-IL-36R antibody, about 45 mM acetate, about 150 mM sucrose, about 25 mM L-Arginine, about 0.4 g/L Polysorbate 20, with a pH of about 5.5;

VIII. formulation comprising about 20 mg/mL to about 150 mg/mL of the anti-IL-36R antibody, about 35 mM histidine, about 180 mM trehalose, about 25 mM L-Arginine, about 3 mM NaCl, about 0.4 g/L Polysorbate 80, with a pH of about 6.0;

IX. formulation comprising about 20 mg/mL to about 150 mg/mL of the anti-IL-36R antibody, about 25 mM acetate, about 100 mM mannitol, about 50 mM NaCl, about 0.2 g/L Polysorbate 20, with a pH of about 5.5; and X. formulation comprising about 20 mg/mL to about 150 mg/mL of the anti-IL-36R antibody, about 20 mM succinate, about 220 mM sucrose, about 0.1 g/L Polysorbate 80, with a pH of about 6.0.

In an embodiment relating to any of the first or second aspects, the formulation comprises about 20 mg/mL to about 150 mg/mL of an anti-IL-36R antibody, about 40 mM histidine, about 120 mM sucrose, about 50 mM L-Arginine, about 5 mM NaCl and about 1.0 g/L Polysorbate 20, with a pH of about 6.0; wherein the anti-IL-36R antibody consists of a light chain variable region comprising the amino acid sequence of SEQ ID NO: 80; and a heavy chain variable region comprising the amino acid sequence of SEQ ID NO: 87. In a related embodiment, the formulation comprises 20 mg/mL of the antibody. In a related embodiment, the formulation comprises 150 mg/mL of the antibody. In another embodiment, the formulation comprises about 20 mg/mL to about 150 mg/mL of an anti-IL-36R antibody, about 45 mM acetate, about 150 mM sucrose, about 25 mM L-Arginine, about 0.4 g/L Polysorbate 20, with a pH of about 5.5; wherein the anti-IL-36R antibody consists of a light chain variable region comprising the amino acid sequence of SEQ ID NO: 80; and a heavy chain variable region comprising the amino acid sequence of SEQ ID NO: 87. In a related embodiment, the formulation comprises 20 mg/mL of the antibody. In a related embodiment, the formulation comprises 150 mg/mL of the antibody.

In an embodiment relating to any of the first or second aspects, the formulation comprises about 20 mg/mL to about 150 mg/mL of an anti-IL-36R antibody, about 40 mM histidine, about 120 mM sucrose, about 50 mM L-Arginine, about 5 mM NaCl and about 1.0 g/L Polysorbate 20, with a pH of about 6.0; wherein the anti-IL-36R antibody consists of a light chain variable region comprising the amino acid sequence of SEQ ID NO: 80; and a heavy chain variable region comprising the amino acid sequence of SEQ ID NO: 89. In a related embodiment, the formulation comprises 20 mg/mL of the antibody. In a related embodiment, the formulation comprises 150 mg/mL of the antibody. In another embodiment, the formulation comprises about 20 mg/mL to about 150 mg/mL of an anti-IL-36R antibody, about 45 mM acetate, about 150 mM sucrose, about 25 mM L-Arginine, about 0.4 g/L Polysorbate 20, with a pH of about 5.5; wherein the anti-IL-36R antibody consists of a light chain variable region comprising the amino acid sequence of SEQ ID NO: 80; and a heavy chain variable region comprising the amino acid sequence of SEQ ID NO: 89. In a related embodiment, the formulation comprises 20 mg/mL of the antibody. In a related embodiment, the formulation comprises 150 mg/mL of the antibody.

In an embodiment relating to any of the first or second aspects, the formulation comprises about 20 mg/mL to about 150 mg/mL of an anti-IL-36R antibody, about 40 mM histidine, about 120 mM sucrose, about 50 mM L-Arginine, about 5 mM NaCl and about 1.0 g/L Polysorbate 20, with a pH of about 6.0; wherein the anti-IL-36R antibody consists of a light chain comprising an amino acid sequence set forth as SEQ ID NO:118 and a heavy chain comprising an amino acid sequence set forth as SEQ ID NO:125. In a related embodiment, the formulation comprises 20 mg/mL of the antibody. In a related embodiment, the formulation comprises 150 mg/mL of the antibody. In another embodiment, the formulation comprises about 20 mg/mL to about 150 mg/mL of an anti-IL-36R antibody, about 45 mM acetate, about 150 mM sucrose, about 25 mM L-Arginine, about 0.4 g/L Polysorbate 20, with a pH of about 5.5; wherein the anti-IL-36R antibody consists of a light chain comprising an amino acid sequence set forth as SEQ ID NO:118 and a heavy chain comprising an amino acid sequence set forth as SEQ ID NO:125. In a related embodiment, the formulation comprises 20 mg/mL of the antibody. In a related embodiment, the formulation comprises 150 mg/mL of the antibody.

In an embodiment relating to any of the first or second aspects, the formulation comprises about 20 mg/mL to about 150 mg/mL of an anti-IL-36R antibody, about 40 mM histidine, about 120 mM sucrose, about 50 mM L-Arginine, about 5 mM NaCl and about 1.0 g/L Polysorbate 20, with a pH of about 6.0; wherein the anti-IL-36R antibody consists of a light chain comprising an amino acid sequence set forth as SEQ ID NO:118 and a heavy chain comprising an amino acid sequence set forth as SEQ ID NO:127. In a related embodiment, the formulation comprises 20 mg/mL of the antibody. In a related embodiment, the formulation comprises 150 mg/mL of the antibody. In another embodiment, the formulation comprises about 20 mg/mL to about 150 mg/mL of an anti-IL-36R antibody, about 45 mM acetate, about 150 mM sucrose, about 25 mM L-Arginine, about 0.4 g/L Polysorbate 20, with a pH of about 5.5; wherein the anti-IL-36R antibody consists of a light chain comprising an amino acid sequence set forth as SEQ ID NO:118 and a heavy chain comprising an amino acid sequence set forth as SEQ ID NO:127. In a related embodiment, the formulation comprises 20 mg/mL of the antibody. In a related embodiment, the formulation comprises 150 mg/mL of the antibody.

In an embodiment relating to any of the first or second aspects, the formulation comprises about 20 mg/mL to about 150 mg/mL of an anti-IL-36R antibody, about 25 mM citrate and about 0.4 g/L Polysorbate 20, with a pH of about 6.5; wherein the anti-IL-36R antibody consists of a light chain comprising an amino acid sequence set forth as SEQ ID NO:118 and a heavy chain comprising an amino acid sequence set forth as SEQ ID NO:127. In another embodiment, the formulation comprises about 20 mg/mL to about 150 mg/mL of an anti-IL-36R antibody, about 25 mM citrate and about 0.4 g/L Polysorbate 20, with a pH of about 6.5; wherein the anti-IL-36R antibody consists of a light chain variable region comprising the amino acid sequence of SEQ ID NO: 80; and a heavy chain variable region comprising the amino acid sequence of SEQ ID NO: 89.

In a third aspect, the present invention provides a pharmaceutical product comprising a vial or syringe or device (e.g., autoinjector or needle safety device) comprising the pharmaceutical formulation according to the first or second aspect of the present invention. In an embodiment relating to this aspect, the pharmaceutical product comprises a pre-assembled injection device comprising the syringe (syringe comprising the pharmaceutical formulation) according to the first or second aspect of the present invention. In a related embodiment, the pre-assembled injection device is an autoinjector or needle safety device.

In an embodiment relating to the third aspect, said "pre-assembled injection device" is either a syringe with plunger rod and finger flange, a needle-safety device or an autoinjector. The needle safety device provides a needle protection mechanism which upon activation or injection retracts the needle from the injection site. For example, the needle safety device may be driven by a spring. An autoinjector is a medical device designed to deliver one dose of a drug, particularly an injectable drug. Syringes, needle-safety devices and autoinjectors avoid the need of transferring a drug from a vial into an injection device—a step which is laborious, often difficult and subject to particular risks (e.g., contamination or misdosage). Autoinjectors and needle-safety devices are easy to use and are intended for self-administration by patients, or administration by untrained personnel. Autoinjectors have a retractable needle, or a needle which is protected by a particular shield. Compared to syringes they offer facilitated handling, and they thus reduce risk of injury, or contamination, which contributes to their suitability for home use.

Autoinjectors further help to overcome the hesitation often associated with self-administration of the needle-based drug delivery device, and thus provide enhanced patient compliance, which in turn secures that the drug is regularly taken according to the prescribed dosage regimen, thus increasing the likelihood of therapeutic success. This is particularly important in therapeutic regimens which require repeated treatment, as is the case in many chronic diseases, like autoimmune diseases or in many cancer types which, due to targeted therapy, turn chronic nor near chronic.

Further, in such indications it is particularly beneficial if the patient can treat himself or herself at home, as is the case with autoinjectors and needle-safety devices. Home treatment further reduces therapy costs and increases patient compliance, as the patients do not have to see medical personnel each time the dosage regimen requires that the drug is delivered. In an embodiment of the invention, said autoinjector is from the spring-loaded syringe type. Such type contains a spring-loaded needle connected to a syringe. In another embodiment, said autoinjector is from the gas jet autoinjector type. The latter contains a cylinder of pressurised gas and propels a fine jet of liquid through the skin without the use of a needle. This has the advantage that the autoinjector can be reloaded, and a variety of different doses or different drugs can be used. In another embodiment of the invention, said pre-assembled injection device is selected from the group consisting of a conventional autoinjector, and/or wet/dry auto-injector.

A conventional autoinjector comprises the syringe (syringe filled with the pharmaceutical formulation) as outlined above and can be used for administration directly. A wet/dry auto-injector (also called "Liquid Dry autoinjector" or "Dual Chamber autoinjector") is a two-chambered autoinjector that keeps the pharmaceutical formulation, or its active component, disposed in a dry chamber in a dry, stable form (e.g., lyophilized) until it is used. Prior to administration, the pharmaceutical formulation, or its active component, is reconstituted by transfer into a second chamber ("wet chamber") containing a solvent or the solvent from a second chamber is transferred onto the first chamber. For said purpose, the dry chamber containing the solid medicament powder can for example also contain a volume of air or other gas which is replaced by the solvent when the pharmaceutical formulation, or its active component is reconstituted.

Preferably, the autoinjector is a disposable autoinjector and for single use. Suitable autoinjectors which can be used in the context of the present invention include the autoinjectors manufactured by Ypsomed. These include monodose devices, like the products sold under the trademarks "LyoTwist", "YpsoMate", "YpsoJect" and "VarioJect". In an embodiment, the outer shell(s) of the autoinjector is customized to increase the ease of use and safety for the user.

Other suitable autoinjectors which can be used in the context of the present invention include the autocoinjectors manufactured by SHL. These include the products sold under the trademarks "Molly™", "DAI™", "DAI™-RNS", "DAI™-R", "SDI MIX+NIT™", "VSDI™", "PSDI™", "Naisa™" and "DCP™ (OEM)".

A further preferred type of autoinjector is the Physioject™ Disposable AutoInjector manufactured by Becton Dickinson. This auto-injector of the conventional type holds 1-2 mL prefilled syringes with a subcutaneous needle, is easy to assemble (2 assembly components), robust, has a large window for visual check and is tamper evident.

Another preferred type of autoinjector is the BD™ Liquid Dry Injector™ manufactured by Becton Dickinson™. This autoinjector of the wet/dry type allows the patient to reconstitute and inject a lyophilized pharmaceutical formulation according to the present invention, eliminating the need to handle vials and syringes.

Yet other suitable autoinjectors are the ASITMauto™ injector and the OTS™™ disposable auto injector provided by BespakInjectables™, the SafeClick™Autoinjector™ provided by Aqueo Future Injection Technologies™, and the SafeClick™-Lyo and the SafeClick™-Visco provided by Future Injection Technology™. This list is however non-restricting.

Preferably, the needle-safety device is a disposable needle-safety device and for single use. Suitable needle-safety device which can be used in the context of the present invention include the needle-safety device manufactured by Nemera. These include mono-dose devices as the passive safety device Safe'n'Sound®.

In an embodiment of the present invention relating to the Nemeras Safe'n'Sound®, a customization of the plunger rod and finger flange increase the ease of handling for the user.

Other suitable passive needle safety devices which might be used in the context of the present invention include the BD Preventis™ or the BD Ultrasafe™ manufactured by BD.

Further passive needle safety devices are for e.g. the Biocorp Newguard™ or the Owen Mumford Unisafe™.

Preferably the needle-safety device is a disposable needle-safety device and for single-use. Suitable needle-safety device which can be used in the context of the present invention include the needle-safety device manufactured by Nemera. These include monodose-devices as the passive safety device Safe'n'Sound®. In an embodiment, the Nemeras Safe'n'Sound® needle safety device has a modified plunger rod and/or finger flange to increase the ease of using and handling for the user.

Other suitable passive needle safety devices which might be used in the context of the present invention include the BD Preventis™ or the BD Ultrasafe™ manufactured by BD.

Further passive needle safety devices are for e.g. the Biocorp Newguard™ or the Owen Mumford Unisafe™.

In another embodiment of the invention relating to the third aspect, the injection device is a pre-filled syringe or as syrette. A syrette is a device for injecting liquid through a needle. It is similar to a syringe except that it has a closed flexible tube instead of a rigid tube and piston. The term "pre-filled syringe" is self-explaining. Pre-filled syringes share many advantages with autoinjectors. Like autoinjectors, pre-filled syringes are available as conventional syringes and wet/dry syringes (also called dual-chamber syringes). Syringes are, for example, provided by Becton Dickinson™, Nuova Ompi™, Schott AG and others. Plunger stoppers are, for example, provided by Becton Dickinson™, West Pharmaceuticals™, and others. Manufacturing of the prefilled syringes can be provided, for example, by Boehringer Ingelheim™, Vetter Pharma International, and others.

In an embodiment relating to the third aspect, the present invention relates a formulation of an anti-IL-36R antibody as disclosed herein provided in a variety of dosage forms and strengths comprising:

(i) An auto Injector (AI)—e.g., a custom-made model by YpsoMate®-comprising:
  a. about 300 mg of the antibody in about 2 mL formulation volume in a single-dose AI;
  b. about 225 mg of the antibody in about 1.5 mL formulation volume in a single-dose AI;
  c. about 150 mg of the antibody in about 1 mL formulation volume in a single-dose AI;
  d. about 75 mg of the antibody in about 0.5 mL formulation volume in a single-dose AI; or
  e. about 60 mg of the antibody in about 0.4 mL formulation volume in a single-dose AI;

(ii) A prefilled syringe equipped with a needle-safety device and, e.g., customized EFF and PR, comprising:
  a. about 300 mg of the antibody in about 2 mL formulation volume in a single-dose prefilled glass syringe;
  b. about 225 mg of the antibody in about 1.5 mL formulation volume in a single-dose prefilled glass syringe;
  c. about 150 mg of the antibody in about 1 mL formulation volume in a single-dose prefilled glass syringe;
  d. about 75 mg of the antibody in about 0.5 mL formulation volume in a single-dose prefilled glass syringe; or
  e. about 60 mg of the antibody in about 0.4 mL formulation volume in a single-dose prefilled glass syringe; or (iii) A prefilled syringe without a needle-safety, comprising:
  a. about 300 mg of the antibody in about 2 mL formulation volume in a single-dose prefilled glass syringe;
  b. about 225 mg of the antibody in about 1.5 mL formulation volume in a single-dose prefilled glass syringe;
  c. about 150 mg of the antibody in about 1 mL formulation volume in a single-dose prefilled glass syringe;
  d. about 75 mg of the antibody in about 0.5 mL formulation volume in a single-dose prefilled glass syringe; or
  e. about 60 mg of the antibody in about 0.4 mL formulation volume in a single-dose prefilled glass syringe; or (iv) A vial comprising:
  a. about 1200 mg of the antibody in about 20 mL formulation volume in a single-dose glass vial;
  b. about 900 mg of the antibody in about 15 mL formulation volume in a single-dose glass vial;
  c. about 600 mg of the antibody in about 10 mL formulation volume in a single-dose glass vial;
  d. about 450 mg of the antibody in about 7.5 mL formulation volume in a single-dose glass vial;
  e. about 300 mg of the antibody in about 5 mL formulation volume in a single-dose glass vial;
  f. about 150 mg of the antibody in about 2.5 mL formulation volume in a single-dose glass vial; or
  g. about 75 mg of the antibody in about 1.25 mL formulation volume in a single-dose glass vial; or
  h. about 60 mg of the antibody in about 1 mL formulation volume in a single-dose glass vial; or
  i. about 30 mg of the antibody in about 0.5 mL formulation volume in a single-dose glass vial; or
(v) An infusion bag, comprising:
  a. 30 mg to 1200 mg of the antibody in about 100 mL to 500 mL 0.9% NaCl solution.

Various other examples or embodiments relating to the third aspect of the present invention are described as numbered clauses (66-77) below for convenience. These are provided as examples and do not limit the subject technology. It is noted that any of the dependent clauses may be combined in any combination, and placed into a respective independent clause, e.g., clause 64. The other clauses can be presented in a similar manner.

66. A pharmaceutical product comprising a vial or syringe comprising the pharmaceutical formulation according to any of clauses of the first or second aspects.
67. The pharmaceutical product according to clause 66 further comprising a pre-assembled injection device.
68. The pharmaceutical product of clause 67 wherein the pre-assembled injection device is an autoinjector or a syringe with or without a needle safety device.
69. A pre-assembled injection device comprising a pharmaceutical formulation according to any one of clauses of the first or second aspects.
70. The pre-assembled injection device according to clause 69, wherein said device is an autoinjector or a syringe with or without a needle safety device.
71. The pre-assembled injection device according to clause 69, wherein said formulation is suitable for intravenous, subcutaneous or intramuscular administration.
72. The pre-assembled injection device according to clause 70, wherein the autoinjector or the syringe with or without needle safety device includes a pharmaceutical formulation comprising:
  an anti-IL-36R antibody or antigen-binding fragment thereof, comprising:
    i. a light chain comprising an amino acid sequence set forth as SEQ ID NO:118 and a heavy chain comprising an amino acid sequence set forth as SEQ ID NO:125; or
    ii. a light chain comprising an amino acid sequence set forth as SEQ ID NO:118 and a heavy chain comprising an amino acid sequence set forth as SEQ ID NO:126; or
      a light chain comprising an amino acid sequence set forth as SEQ ID NO:118 and a heavy chain comprising an amino acid sequence set forth as SEQ ID NO:127; wherein the formulation is selected from the group consisting of:
        I. formulation comprising about 20 mg/ml of the anti-IL-36R antibody, about 40 mM histidine, about 120 mM sucrose, about 50 mM L-Arginine, about 5 mM NaCl and about 1.0 g/L Polysorbate 20, with a pH of about 6.0;
        II. formulation comprising about 60 mg/mL of the anti-IL-36R antibody, about 45 mM acetate, about 150 mM sucrose, about 25 mM L-Arginine, about 0.4 g/L Polysorbate 20, with a pH of about 5.5;
        III. formulation comprising about 20 mg/mL of the anti-IL-36R antibody, about 45 mM acetate, about 180 mM sucrose, about 25 mM Glycine, about 0.4 g/L Polysorbate 80, with a pH of about 5.5;
        IV. formulation comprising about 150 mg/mL of the anti-IL-36R antibody, about 25 mM citrate, about 150 mM trehalose, about 25 mM methionine, about 0.2 g/L Polysorbate 20, with a pH of about 6.0;
        V. formulation comprising about 60 mg/mL of the anti-IL-36R antibody, about 25 mM histidine, about 160 mM sucrose, about 20 mM mannitol, about 0.2 g/L Polysorbate 20, with a pH of about 6.0;
        VI. formulation comprising about 20 mg/mL of the anti-IL-36R antibody, about 25 mM citrate, about 200 mM sucrose, about 0.4 g/L Polysorbate 80, with a pH of about 6.5;
        VII. formulation comprising about 150 mg/mL of the anti-IL-36R antibody, about 45 mM acetate, about 150 mM sucrose, about 25 mM L-Arginine, about 0.4 g/L Polysorbate 20, with a pH of about 5.5;
        VIII. formulation comprising about 15 mg/mL of the anti-IL-36R antibody, about 35 mM histidine, about 180 mM trehalose, about 25 mM L-Arginine, about 3 mM NaCl, about 0.4 g/L Polysorbate 80, with a pH of about 6.0;
        IX. formulation comprising about 80 mg/mL of the anti-IL-36R antibody, about 25 mM acetate, about 100 mM mannitol, about 50 mM NaCl, about 0.2 g/L Polysorbate 20, with a pH of about 5.5; and
        X. formulation comprising about 100 mg/mL of the anti-IL-36R antibody, about 20 mM succinate, about 220 mM sucrose, about 0.1 g/L Polysorbate 80, with a pH of about 6.0.
73. The pre-assembled injection device according to clause 70, wherein the autoinjector or the syringe with a needle safety device includes:
  a. about 300 mg of the antibody in about 2 mL formulation volume; or
  b. about 225 mg of the antibody in about 1.5 mL formulation volume; or
  c. about 150 mg of the antibody in about 1 mL formulation volume; or
  d. about 75 mg of the antibody in about 0.5 mL formulation volume; or
  e. about 60 mg of the antibody in about 0.4 mL formulation volume.
74. The vial according to clause 66, wherein the vial includes:
  a. about 1200 mg of the antibody in about 20 mL formulation volume; or
  b. about 900 mg of the antibody in about 15 mL formulation volume; or c. about 600 mg of the antibody in about 10 mL formulation volume; or
d. about 300 mg of the antibody in about 150 mL formulation volume; or
e. about 1500 mg of the antibody in about 2.5 mL formulation volume.
75. A pharmaceutical product, comprising: a vial comprising about 100 mg to 1500 mg of an anti-IL-36R antibody in powder form; instructions for reconstitution of the anti-IL-36R antibody; and instructions for preparing the reconstituted antibody for infusion, wherein the anti-IL-36R antibody comprises a light chain comprising an amino acid sequence set forth as SEQ ID NO:118 and a heavy chain comprising an amino acid sequence set forth as any one of SEQ ID Nos:125, 126 or 127; and the reconstitution instructions require reconstitution with water for injection to an extractable volume from 1 to 50 mL.
76. The pharmaceutical product according to any of clauses 66-68 or the pre-assembled injection device according to any of clauses 69-73, wherein the pharmaceutical formulation comprises:
a. An anti-IL-36R antibody or an antigen binding fragment thereof present at a concentration within the range from about 0.5 mg/mL to about 220 mg/mL;
b. A buffer present at a concentration within the range from about 20 mM to about 80 mM;
c. A tonicifying agent present at a concentration within the range from about 100 mM to about 400 mM;
wherein the formulation is characterized by a pH within the range from about 5 to about 8 when in aqueous form.
77. The pharmaceutical formulation according to any of clauses 1-10, wherein the pharmaceutical formulation comprises:
d. An anti-IL-36R antibody or an antigen binding fragment thereof present at a concentration within the range from about 0.5 mg/mL to about 220 mg/mL;
e. A buffer present at a concentration within the range from about 20 mM to about 80 mM;
f. A tonicifying agent present at a concentration within the range from about 100 mM to about 400 mM;
wherein the formulation is characterized by a pH within the range from about 5 to about 8 when in aqueous form.

In an embodiment related to the third aspect and/or clauses 66-77, the anti-IL-36R antibody or antigen binding fragment thereof comprises a light chain variable region comprising the amino acid sequence of SEQ ID NO: 80; and a heavy chain variable region comprising the amino acid sequence of SEQ ID NO: 87; or a light chain variable region comprising the amino acid sequence of SEQ ID NO: 80; and a heavy chain variable region comprising the amino acid sequence of SEQ ID NO: 88; or a light chain variable region comprising the amino acid sequence of SEQ ID NO: 80; and a heavy chain variable region comprising the amino acid sequence of SEQ ID NO: 89. In one embodiment the anti-IL-36R antibody comprises a light chain comprising an amino acid sequence set forth as SEQ ID NO:118 and a heavy chain comprising an amino acid sequence set forth as SEQ ID NO:125; or a light chain comprising an amino acid sequence set forth as SEQ ID NO:118 and a heavy chain comprising an amino acid sequence set forth as SEQ ID NO:126; or a light chain comprising an amino acid sequence set forth as SEQ ID NO:118 and a heavy chain comprising an amino acid sequence set forth as SEQ ID NO:127. In a particular embodiment, the anti-IL-36R antibody comprises a light chain variable region comprising the amino acid sequence of SEQ ID NO: 80; and a heavy chain variable region comprising the amino acid sequence of SEQ ID NO: 89. In another particular embodiment, the anti-IL-36R antibody consists of a light chain comprising an amino acid sequence set forth as SEQ ID NO:118 and a heavy chain comprising an amino acid sequence set forth as SEQ ID NO:127.

In a forth aspect, the present invention relates to a method of making a pharmaceutical formulation of the present invention, said method comprising: a) culturing mammalian cells having stably incorporated into their genome one or more nucleic acids encoding the light and heavy chains of an anti-IL-36R antibody disclosed herein so that the cells secrete the antibody into the cell culture media, and purifying the antibody from the cell culture media; and b) preparing the formulation according to the first or second aspect. In a related embodiment, the nucleic acid encoding the light chain of the anti-IL-36R antibody comprises a nucleotide sequence encoding SEQ ID NO:118, and wherein the nucleic acid encoding the heavy chain of the anti-IL-36R antibody comprises a nucleotide sequence encoding SEQ ID NO:125. In another related embodiment, the nucleic acid encoding the light chain of the anti-IL-36R antibody comprises a nucleotide sequence encoding SEQ ID NO:118, and wherein the nucleic acid encoding the heavy chain of the anti-IL-36R antibody comprises a nucleotide sequence encoding SEQ ID NO:126. In another related embodiment, the nucleic acid encoding the light chain of the anti-IL-36R antibody comprises a nucleotide sequence encoding SEQ ID NO:118, and wherein the nucleic acid encoding the heavy chain of the anti-IL-36R antibody comprises a nucleotide sequence encoding SEQ ID NO:127.

In another embodiment relating to the forth aspect, the formulation comprises an anti-IL-36R antibody or antigen-binding fragment thereof, comprising:
i. a light chain comprising an amino acid sequence set forth as SEQ ID NO:118 and a heavy chain comprising an amino acid sequence set forth as SEQ ID NO:125; or
ii. a light chain comprising an amino acid sequence set forth as SEQ ID NO:118 and a heavy chain comprising an amino acid sequence set forth as SEQ ID NO:126; or
iii. a light chain comprising an amino acid sequence set forth as SEQ ID NO:118 and a heavy chain comprising an amino acid sequence set forth as SEQ ID NO:127;
wherein the formulation is selected from the group consisting of:
I. formulation comprising about 20 mg/mL of the anti-IL-36R antibody, about 40 mM histidine, about 120 mM sucrose, about 50 mM L-Arginine, about 5 mM NaCl and about 1.0 g/L Polysorbate 20, with a pH of about 6.0;
II. formulation comprising about 60 mg/mL of the anti-IL-36R antibody, about 45 mM acetate, about 150 mM sucrose, about 25 mM L-Arginine, about 0.4 g/L Polysorbate 20, with a pH of about 5.5;
III. formulation comprising about 20 mg/mL of the anti-IL-36R antibody, about 45 mM acetate, about 180 mM sucrose, about 25 mM Glycine, about 0.4 g/L Polysorbate 80, with a pH of about 5.5;
IV. formulation comprising about 150 mg/mL of the anti-IL-36R antibody, about 25 mM citrate, about 150 mM trehalose, about 25 mM methionine, about 0.2 g/L Polysorbate 20, with a pH of about 6.0;
V. formulation comprising about 60 mg/mL of the anti-IL-36R antibody, about 25 mM histidine, about 160 mM sucrose, about 20 mM mannitol, about 0.2 g/L Polysorbate 20, with a pH of about 6.0;

VI. formulation comprising about 20 mg/mL of the anti-IL-36R antibody, about 25 mM citrate, about 200 mM sucrose, about 0.4 g/L Polysorbate 80, with a pH of about 6.5;

VII. formulation comprising about 150 mg/mL of the anti-IL-36R antibody, about 45 mM acetate, about 150 mM sucrose, about 25 mM L-Arginine, about 0.4 g/L Polysorbate 20, with a pH of about 5.5;

VIII. formulation comprising about 15 mg/mL of the anti-IL-36R antibody, about 35 mM histidine, about 180 mM trehalose, about 25 mM L-Arginine, about 3 mM NaCl, about 0.4 g/L Polysorbate 80, with a pH of about 6.0;

IX. formulation comprising about 80 mg/mL of the anti-IL-36R antibody, about 25 mM acetate, about 100 mM mannitol, about 50 mM NaCl, about 0.2 g/L Polysorbate 20, with a pH of about 5.5; and X. formulation comprising about 100 mg/mL of the anti-IL-36R antibody, about 20 mM succinate, about 220 mM sucrose, about 0.1 g/L Polysorbate 80, with a pH of about 6.0.

In an embodiment related to the forth aspect, the anti-IL-36R antibody or antigen binding fragment thereof comprises a light chain variable region comprising the amino acid sequence of SEQ ID NO: 80; and a heavy chain variable region comprising the amino acid sequence of SEQ ID NO: 87; or a light chain variable region comprising the amino acid sequence of SEQ ID NO: 80; and a heavy chain variable region comprising the amino acid sequence of SEQ ID NO: 88; or a light chain variable region comprising the amino acid sequence of SEQ ID NO: 80; and a heavy chain variable region comprising the amino acid sequence of SEQ ID NO: 89. In one embodiment the anti-IL-36R antibody comprises a light chain comprising an amino acid sequence set forth as SEQ ID NO:118 and a heavy chain comprising an amino acid sequence set forth as SEQ ID NO:125; or a light chain comprising an amino acid sequence set forth as SEQ ID NO:118 and a heavy chain comprising an amino acid sequence set forth as SEQ ID NO:126; or a light chain comprising an amino acid sequence set forth as SEQ ID NO:118 and a heavy chain comprising an amino acid sequence set forth as SEQ ID NO:127. In a particular embodiment, the anti-IL-36R antibody comprises a light chain variable region comprising the amino acid sequence of SEQ ID NO: 80; and a heavy chain variable region comprising the amino acid sequence of SEQ ID NO: 89. In another particular embodiment, the anti-IL-36R antibody consists of a light chain comprising an amino acid sequence set forth as SEQ ID NO:118 and a heavy chain comprising an amino acid sequence set forth as SEQ ID NO:127.

In a fifth aspect, the present invention relates to a method of reducing aggregation and/or fragmentation of an anti-IL-36R antibody disclosed herein, comprising formulating the antibody in a buffer system and surfactant and evaluating data (e.g., any antibody aggregation) before and after the antibody is formulated. In an embodiment relating to the fifth aspect, the antibody is formulated according to any of the embodiments of the first or second aspects.

In an embodiment relating to the fifth aspect, the formulation includes the an anti-IL-36R antibody or antigen-binding fragment thereof, comprising:

i. a light chain comprising an amino acid sequence set forth as SEQ ID NO:118 and a heavy chain comprising an amino acid sequence set forth as SEQ ID NO:125; or ii. a light chain comprising an amino acid sequence set forth as SEQ ID NO:118 and a heavy chain comprising an amino acid sequence set forth as SEQ ID NO:126; or iii. a light chain comprising an amino acid sequence set forth as SEQ ID NO:118 and a heavy chain comprising an amino acid sequence set forth as SEQ ID NO:127;

wherein the formulation is selected from the group consisting of:

I. formulation comprising about 20 mg/ml of the anti-IL-36R antibody, about 40 mM histidine, about 120 mM sucrose, about 50 mM L-Arginine, about 5 mM NaCl and about 1.0 g/L Polysorbate 20, with a pH of about 6.0;

II. formulation comprising about 60 mg/mL of the anti-IL-36R antibody, about 45 mM acetate, about 150 mM sucrose, about 25 mM L-Arginine, about 0.4 g/L Polysorbate 20, with a pH of about 5.5;

III. formulation comprising about 20 mg/mL of the anti-IL-36R antibody, about 45 mM acetate, about 180 mM sucrose, about 25 mM Glycine, about 0.4 g/L Polysorbate 80, with a pH of about 5.5;

IV. formulation comprising about 150 mg/mL of the anti-IL-36R antibody, about 25 mM citrate, about 150 mM trehalose, about 25 mM methionine, about 0.2 g/L Polysorbate 20, with a pH of about 6.0;

V. formulation comprising about 60 mg/mL of the anti-IL-36R antibody, about 25 mM histidine, about 160 mM sucrose, about 20 mM mannitol, about 0.2 g/L Polysorbate 20, with a pH of about 6.0;

VI. formulation comprising about 20 mg/mL of the anti-IL-36R antibody, about 25 mM citrate, about 200 mM sucrose, about 0.4 g/L Polysorbate 80, with a pH of about 6.5;

VII. formulation comprising about 150 mg/mL of the anti-IL-36R antibody, about 45 mM acetate, about 150 mM sucrose, about 25 mM L-Arginine, about 0.4 g/L Polysorbate 20, with a pH of about 5.5;

VIII. formulation comprising about 15 mg/mL of the anti-IL-36R antibody, about 35 mM histidine, about 180 mM trehalose, about 25 mM L-Arginine, about 3 mM NaCl, about 0.4 g/L Polysorbate 80, with a pH of about 6.0;

IX. formulation comprising about 80 mg/mL of the anti-IL-36R antibody, about 25 mM acetate, about 100 mM mannitol, about 50 mM NaCl, about 0.2 g/L Polysorbate 20, with a pH of about 5.5; and X. formulation comprising about 100 mg/mL of the anti-IL-36R antibody, about 20 mM succinate, about 220 mM sucrose, about 0.1 g/L Polysorbate 80, with a pH of about 6.0.

In an embodiment related to the fifth aspect, the anti-IL-36R antibody or antigen binding fragment thereof comprises a light chain variable region comprising the amino acid sequence of SEQ ID NO: 80; and a heavy chain variable region comprising the amino acid sequence of SEQ ID NO: 87; or a light chain variable region comprising the amino acid sequence of SEQ ID NO: 80; and a heavy chain variable region comprising the amino acid sequence of SEQ ID NO: 88; or a light chain variable region comprising the amino acid sequence of SEQ ID NO: 80; and a heavy chain variable region comprising the amino acid sequence of SEQ ID NO: 89. In one embodiment the anti-IL-36R antibody comprises a light chain comprising an amino acid sequence set forth as SEQ ID NO:118 and a heavy chain comprising an amino acid sequence set forth as SEQ ID NO:125; or a light chain comprising an amino acid sequence set forth as SEQ ID NO:118 and a heavy chain comprising an amino acid sequence set forth as SEQ ID NO:126; or a light chain comprising an amino acid sequence set forth as SEQ ID NO:118 and a heavy chain comprising an amino acid sequence set forth as SEQ ID NO:127. In a particular embodiment, the anti-IL-36R antibody comprises a light chain variable region comprising the amino acid sequence of SEQ ID NO: 80; and a heavy chain variable region comprising the amino acid sequence of SEQ ID NO: 89. In another particular embodiment, the anti-IL-36R antibody consists of a light chain comprising an amino acid sequence set forth as SEQ ID NO:118 and a heavy chain comprising an amino acid sequence set forth as SEQ ID NO:127.

In a sixth aspect, the present invention relates to a kit of parts, comprising at least a container comprising a pharmaceutical formulation according to any of aspects first or second, and an injection device according to aspect third. In an embodiment, the kit of parts, comprising at least a container comprising a pharmaceutical formulation according to the first or second aspect. In a related embodiment, the kit of parts comprises one or more vials containing the formulation according to the first or second aspect and instructions for subcutaneous or intramuscular administration of the formulation to a subject. The kit of parts or the injection device according to the invention is, for example, adapted for subcutaneous administration. In such case, the injection needle has, preferably, a length of ≥10 mm to ≤100 mm and a gauge of between 0.2 mm and 1 mm (gauge 33 to 19).

In an embodiment relating to the sixth aspect, the formulation includes the an anti-IL-36R antibody or antigen-binding fragment thereof, comprising:
  i. a light chain comprising an amino acid sequence set forth as SEQ ID NO:118 and a heavy chain comprising an amino acid sequence set forth as SEQ ID NO:125; or
  ii. a light chain comprising an amino acid sequence set forth as SEQ ID NO:118 and a heavy chain comprising an amino acid sequence set forth as SEQ ID NO:126; or
  iii. a light chain comprising an amino acid sequence set forth as SEQ ID NO:118 and a heavy chain comprising an amino acid sequence set forth as SEQ ID NO:127;
    wherein the formulation is selected from the group consisting of:
    I. formulation comprising about 20 mg/ml of the anti-IL-36R antibody, about 40 mM histidine, about 120 mM sucrose, about 50 mM L-Arginine, about 5 mM NaCl and about 1.0 g/L Polysorbate 20, with a pH of about 6.0;
    II. formulation comprising about 60 mg/mL of the anti-IL-36R antibody, about 45 mM acetate, about 150 mM sucrose, about 25 mM L-Arginine, about 0.4 g/L Polysorbate 20, with a pH of about 5.5;
    III. formulation comprising about 20 mg/mL of the anti-IL-36R antibody, about 45 mM acetate, about 180 mM sucrose, about 25 mM Glycine, about 0.4 g/L Polysorbate 80, with a pH of about 5.5;
    IV. formulation comprising about 150 mg/mL of the anti-IL-36R antibody, about 25 mM citrate, about 150 mM trehalose, about 25 mM methionine, about 0.2 g/L Polysorbate 20, with a pH of about 6.0;
    V. formulation comprising about 60 mg/mL of the anti-IL-36R antibody, about 25 mM histidine, about 160 mM sucrose, about 20 mM mannitol, about 0.2 g/L Polysorbate 20, with a pH of about 6.0;
    VI. formulation comprising about 20 mg/mL of the anti-IL-36R antibody, about 25 mM citrate, about 200 mM sucrose, about 0.4 g/L Polysorbate 80, with a pH of about 6.5;
    VII. formulation comprising about 150 mg/mL of the anti-IL-36R antibody, about 45 mM acetate, about 150 mM sucrose, about 25 mM L-Arginine, about 0.4 g/L Polysorbate 20, with a pH of about 5.5;
    VIII. formulation comprising about 15 mg/mL of the anti-IL-36R antibody, about 35 mM histidine, about 180 mM trehalose, about 25 mM L-Arginine, about 3 mM NaCl, about 0.4 g/L Polysorbate 80, with a pH of about 6.0;
    IX. formulation comprising about 80 mg/mL of the anti-IL-36R antibody, about 25 mM acetate, about 100 mM mannitol, about 50 mM NaCl, about 0.2 g/L Polysorbate 20, with a pH of about 5.5; and
    X. formulation comprising about 100 mg/mL of the anti-IL-36R antibody, about 20 mM succinate, about 220 mM sucrose, about 0.1 g/L Polysorbate 80, with a pH of about 6.0.

In an embodiment relating to the sixth aspect, the injection device is a pre-assembled injection device comprising an autoinjector or a needle safety device. In a related embodiment, the autoinjector or needle safety device each includes: (a) about 300 mg of the antibody in a total volume of about 2 mL; (b) about 225 mg of the antibody in a total volume of about 1.5 mL; (c) about 150 mg of the antibody in a total volume of about 1 mL; (d) about 75 mg of the antibody in a total volume of about 0.5 mL; or (e) about 60 mg of the antibody in a total volume of about 0.4 mL.

According to yet another aspect of the present invention, the use of a formulation according to the invention, of a pre-assembled injection device according to the invention or of a kit of parts according to the invention, for intravenous and/or subcutaneous administration is provided.

In an embodiment related to the sixth aspect, the anti-IL-36R antibody or antigen binding fragment thereof comprises a light chain variable region comprising the amino acid sequence of SEQ ID NO: 80; and a heavy chain variable region comprising the amino acid sequence of SEQ ID NO: 87; or a light chain variable region comprising the amino acid sequence of SEQ ID NO: 80; and a heavy chain variable region comprising the amino acid sequence of SEQ ID NO: 88; or a light chain variable region comprising the amino acid sequence of SEQ ID NO: 80; and a heavy chain variable region comprising the amino acid sequence of SEQ ID NO: 89. In one embodiment the anti-IL-36R antibody comprises a light chain comprising an amino acid sequence set forth as SEQ ID NO:118 and a heavy chain comprising an amino acid sequence set forth as SEQ ID NO:125; or a light chain comprising an amino acid sequence set forth as SEQ ID NO:118 and a heavy chain comprising an amino acid sequence set forth as SEQ ID NO:126; or a light chain comprising an amino acid sequence set forth as SEQ ID NO:118 and a heavy chain comprising an amino acid sequence set forth as SEQ ID NO:127. In a particular embodiment, the anti-IL-36R antibody comprises a light chain variable region comprising the amino acid sequence of SEQ ID NO: 80; and a heavy chain variable region comprising the amino acid sequence of SEQ ID NO: 89. In another particular embodiment, the anti-IL-36R antibody consists of a light chain comprising an amino acid sequence set forth as SEQ ID NO:118 and a heavy chain comprising an amino acid sequence set forth as SEQ ID NO:127.

According to yet another aspect of the present invention, the use of a formulation according to the invention, of a pre-assembled injection device according to the invention or of a kit of parts according to the invention, for treatment of at least one disease selected from the group consisting of autoimmune disorders and/or malignant diseases is provided. Non-restricting examples for autoimmune disorders covered by said definition include psoriasis, rheumatoid arthritis, inflammatory bowel disease or psoriatic arthritis, chronic obstructive pulmonary disorder (COPD), asthma, scleroderma, palmoplantar pustulosis, generalized pustular psoriasis, atopic dermatitis, diabetic nephropathy, lupus nephritis, scleroderma, ankylosing spondylitis, deficiency in the IL-36 receptor antagonist autoimmune disease (DITRA), deficiency in the IL-1 receptor antagonist autoimmune disease (DIRA) or cryopyrin associated periodic syndromes (CAPS), rheumatoid arthritis (RA), systemic lupus erythematosus (SLE), scleroderma, Sjogren's syndrome, multiple sclerosis, psoriasis, psoriatic arthritis, inflammatory bowel disease (e.g., ulcerative colitis and Crohn's disease), pulmonary inflammation, asthma, idiopathic thrombocytopenic purara (ITP) epithelial inflammatory disorders, fibrosis and ankylosing spondylitis. In a further preferred embodiment the kit comprises instructions for subcutaneous or intramuscular administration of the formulation to a subject.

Antibodies

The anti-IL-36R antibodies of the present invention are disclosed in U.S. Pat. No. 9,023,995 or WO 2013/074569, the entire content of each of which is incorporated herein by reference.

Messenger RNAs for IL-36α, IL-36β, and IL-36γ are highly expressed in several tissues, particularly in internal epithelial tissues, which are exposed to pathogens and in skin. Interestingly, expression of IL-36Ra and IL-36α is significantly up-regulated in IL-1β/TNF-α-stimulated human keratinocytes, and IL-36Ra and IL-36γ mRNA are highly increased in lesional psoriasis skin. Moreover, IL-36γ protein production is enhanced in human keratinocytes after TNF-α and IFN-γ stimulation. Elevated IL-36α mRNA and protein expression was reported also in chronic kidney disease. Taken together, these data indicate that IL-36R ligands, including IL-36α, IL-36β, and IL-36γ, exert proinflammatory effects in vitro and in vivo and that IL-36Ra acts as a natural antagonist, thus mimicking the IL-1/IL-1Ra system. Evidence suggests that IL-36R ligands are involved in a number of disease conditions including inflammatory diseases. The anti-IL-36R antibodies described herein reduce or block IL36 ligand-mediated signaling and are useful in treating such conditions or diseases. Variable regions and CDRs of representative antibodies of the present invention are disclosed below:

Anti-IL-36R Mouse Antibody Sequences

Variable regions and CDRs of representative mouse lead antibodies of the present invention (mouse leads) are shown below:

```
Light Chain Variable Region (VK) Amino Acid Sequences

>33D10B12vK Protein (antibody 33D10)
QIVLTQSPAIMSASLGERVTMTCTASSSVSSSYLHWYQKKPGSSPKLWVYSTSNLAS
GVPVRFSGSGSGTSYSLTISSMEAEDAATYYCHQHHRSPVTFGSGTKLEMK (SEQ ID
NO: 1)

>172C8B12 vK protein (antibody 172C8)
DIQMTQSPASQSASLGESVTFTCLASQTIGTWLAWYQQRPGKSPQLLIYAATSLADG
VPSRFSGSGSGTQFSFNIRSLQAEDFASYYCQQVYTTPLTFGGGTKLEIK (SEQ ID NO:
2)

>67E7E8 vK protein (antibody 67E7)
DIQMTQSPASQSASLGESVTFTCLASQTIGTWLGWYQQKPGKSPQLLIYRSTTLADG
VPSRFSGSGSGTKFSFKISSLQAADFASYYCQQLYSAPYTFGGGTKLEIR (SEQ ID NO:
3)

>78C8D1 vK Protein (antibody 78C8)
DVLLTQTPLSLPVSLGDQASISCRSSQNIVHSNGNTYLQWYLQKPGQSPKLLIYKVSN
RFSGVPDRFSGSGSGTDFTLKISRVEAEDLGVYYCFQGSHVPFTFGAGTKLELK (SEQ
ID NO: 4)

>81A1D1 vK Protein (antibody 81A1)
DIQMTQTTSSLSASLGDRVTISCRASQDIYKYLNWYQQKPDGTLKLLIYYTSGLHSG
VPSRFSGSGSGTDFSLTISNLEPEDIATYFCQQDSKFPWTFGGDTKLEIK (SEQ ID NO:
5)

>81B4E11 vK Protein (antibody 81B4)
QIVLTQSPAIMSASLGERVTMTCTASS SVSSSYFHWYQQKPGSSPKLWIYRTSNLASG
VPGRFSGSGSGTSYSLTISSMEAEDAATYYCHQFHRSPLTFGAGTKLELK (SEQ ID
NO: 6)

>73C5C10 vK protein (antibody 73C5)
DIVMTQSQKFLSTSVGVRVSVTCKASQDVGTNVLWYQQKIGQSPKPLIYSASYRHSG
VPDRFTGSGSGTDFTLIISNVQSEDLAEYFCQQYSRYPLTFGPGTKLELK (SEQ ID NO:
7)

>73F6F8 vK protein (antibody 73F6)
DIVMTQSQKFLSTSVGVRVSVTCKASQDVGTNVLWYQQKIGQSPKALIYSASYRHS
GVPDRFTGSGSGTDFTLIITNVQSEDLAEYFCQQYSRYPLTFGPGTKLELK (SEQ ID
NO: 8)
```

>76E10E8 vK protein (antibody 76E10)
DIVMTQSQKFMSATVGGRVNITCKASQNVGRAVAWYQQKPGQSPKLLTHSASNRY
TGVPDRFTGSGSGTDFTLTITNMQSEDLADYFCQQYSSYPLTFGAGTKLDLK (SEQ
ID NO: 9)

>89A12B8 vK protein (antibody 89A12)
DIQMTQSPASQSASLGESVTFSCLASQTIGTWLGWYQQKPGKSPQLLIYRATSLADG
VPSRFSGSGSGTNFSFKISSLQAEDLASYYCQQLYSGPYTFGGGTKLEIR (SEQ ID NO:
10)

Heavy Chain Variable Region (VH) Amino Acid Sequences

>33D10B12vH Protein (antibody 33D10)
QVQLQQSGTELLKPGASVKLSCKASGNTVTSYWMHWVKQRPGQGLEWIGEILPSTG
RTNYNENFKGKAMLTVDKSSSTAYMQLSSLASEDSAVYYCTIVYFGNPWFAYWGQ
GTLVTVSA (SEQ ID NO: 11)

>172C8B12 vH protein (antibody 172C8)
EVQLQQSGPELVKPGASVKLSCKASGYTFTDNYMNWVRQSHGKSLEWIGRVNPSN
GDTKYNQNFKGKATLTVDKSLSTAYMQLNGLTSEDSAVYYCGRTKNFYSSYSYDD
AMDYWGQGTSVTVSS (SEQ ID NO: 12)

>67E7E8 vH protein (antibody 67E7)
EVQLQQSGAEFVRPGASVKFSCTASGFNIKDDYIHWVRQRPEQGLEWVGRIDPANG
NTKYAPKFQDKATITADTSSNTAYLQLSSLTSEDTAVYYCAKSFPNNYYSYDDAFAY
WGQGTLVTVSA (SEQ ID NO: 13)

>78C8D1 vH Protein (antibody 78C8)
QVQLKESGPVLVAPSQSLSITCTVSGFSLTKFGVHWIRQTPGKGLEWLGVIWAGGPT
NYNSALMSRLTISKDISQSQVFLRIDSLQTDDTAMYYCAKQIYYSTLVDYWGQGTSV
TVSS (SEQ ID NO: 14)

>81A1D1 vH Protein (antibody 81A1)
QVQLKESGPGLVAPSQSLFITCTVSGFSLSSYEINWVRQVPGKGLEWLGVIWTGITTN
YNSALISRLSISKDNSKSLVFLKMNSLQTDDTAIYYCARGTGTGFYYAMDYWGQGT
SVTVSS (SEQ ID NO: 15)

>81B4E11 vH Protein (antibody 81B4)
QVQLQQPGADFVRPGASMRLSCKASGYSFTSSWIHWVKQRPGQGLEWIGEINPGNV
RTNYNENFRNKATLTVDKSSTTAYMQLRSLTSADSAVYYCTVVFYGEPYFPYWGQ
GTLVTVSA (SEQ ID NO: 16)

>73C5C10 vH Protein (antibody 73C5)
QVQLKESGPGLVAPSQSLSITCTVSGFSLTNYAVHWVRQFPGKGLEWLGVIWSDGST
DFNAPFKSRLSINKDNSKSQVFFKMNSLQIDDTAIYYCARKGGYSGSWFAYWGQGT
LVTVSA (SEQ ID NO: 17)

>73F6F8 vH protein (antibody 73F6)
QVQLKESGPGLVAPSQSLSITCTVSGFSLTNYAVHWVRQFPGKGLEWLGVIWSDGST
DYNAPFKSRLSINKDNSKSQVFFKMNSLQTDDTAIYYCARKGGYSGSWFAYWGQGT
LVTVSA (SEQ ID NO: 18)

>76E10E8 vH protein (antibody 76E10)
QVQLKESGPVLVAPSQSLSITCTVSGFSLTNYGVHWVRQPPGKGLEWLGVIWPVGST
NYNSALMSRLSIHKDNSKSQVFLRMNSLQTDDTAIYYCAKMDWDDFFDYWGQGTT
LTVSS(SEQ ID NO: 19)

>89A12B8 vH Protein (antibody 89A12)
EVQLQQSGAELVRPGASVRLSCTASGFNIKDDYIHWVRQRPKQGLEWLGRIDPANG
NTKYDPRFQDKATITADTSSNTAYLHLSSLTSEDTAVYYCAKSFPDNYYSYDDAFAY
WGQGTLVTVSA (SEQ ID NO: 20)

Light chain CDR-1 (L-CDR1) Amino Acid Sequences

>33D10G1 L-CDR1
TASSSVSSSYLH (SEQ ID NO: 21)

>172C8B12 L-CDR1
LASQTIGTWLA (SEQ ID NO: 22)

>67E7E8 L-CDR1
LASQTIGTWLG (SEQ ID NO: 23)

>78C8D1 L-CDR1
RSSQNIVHSNGNTYLQ (SEQ ID NO: 24)

>81A1D1 L-CDR1
RASQDIYKYLN (SEQ ID NO: 25)

```
>81B4E11 L-CDR1
TASSSVSSSYFH (SEQ ID NO: 26)

>73C5C10 L-CDR1
KASQDVGTNVL (SEQ ID NO: 27)

>73F6F8 L-CDR1
KASQDVGTNVL (SEQ ID NO: 27)

>76E10E8 L-CDR1
KASQNVGRAVA (SEQ ID NO: 28)

>89A12B8 L-CDR1
LASQTIGTWLG (SEQ ID NO: 29)
```

Light chain CDR-2 (L-CDR2) Amino Acid Sequences

```
>33D10B12 L-CDR2
STSNLAS (SEQ ID NO: 30)

>172C8B12 L-CDR2
AATSLAD ( SEQ ID NO: 31)

>67E7E8 L-CDR2
RSTTLAD (SEQ ID NO: 32)

>78C8D1 L-CDR2
KVSNRFS (SEQ ID NO: 33)

>81A1D1 L-CDR2
YTSGLHS (SEQ ID NO: 34)

>81B4E11 L-CDR2
RTSNLAS (SEQ ID NO: 35)

>73C5C10 L-CDR2
SASYRHS (SEQ ID NO: 36)

>73F6F8 L-CDR2
SASYRHS (SEQ ID NO: 36)

>76E10E8 L-CDR2
SASNRYT (SEQ ID NO: 37)

>89A12B8 L-CDR2
RATSLAD (SEQ ID NO: 38)
```

Light chain CDR-3 (L-CDR3) Amino Acid Sequences

```
>33D10B12 L-CDR3
HQHHRSPVT (SEQ ID NO: 39)

>172C8B12 L-CDR3
QQVYTTPLT (SEQ ID NO: 40)

>67E7E8 L-CDR3
QQLYSAPYT (SEQ ID NO: 41)

>78C8D1 L-CDR3
FQGSHVPFT (SEQ ID NO: 42)

>81A1D1 L-CDR3
QQDSKFPWT (SEQ ID NO: 43)

>81B4E11 L-CDR3
HQFHRSPLT (SEQ ID NO: 44)

>73C5C10 L-CDR3
QQYSRYPLT (SEQ ID NO: 45)

>73F6F8 L-CDR3
QQYSRYPLT (SEQ ID NO: 45)

>76E10E8 L-CDR3
QQYSSYPLT (SEQ ID NO: 46)

>89A12B8 L-CDR3
QQLYSGPYT (SEQ ID NO: 47)
```

Heavy chain CDR-1 (H-CDR1) Amino Acid Sequences

>33D10B12 H-CDR1
GNTVTSYWMH (SEQ ID NO: 48)

>172C8B12 H-CDR1
GYTFTDNYMN (SEQ ID NO: 49)

>67E7E8 H-CDR1
GFNIKDDYIH (SEQ ID NO: 50)

>78C8D1 H-CDR1
GFSLTKFGVH (SEQ ID NO: 51)

>81A1D1 H-CDR1
GFSLSSYEIN (SEQ ID NO: 52)

>81B4E11 H-CDR1
GYSFTSSWIH (SEQ ID NO: 53)

>73C5C10 H-CDR1
GFSLTNYAVH (SEQ ID NO: 54)

>73F6F8 H-CDR1
GFSLTNYAVH (SEQ ID NO: 54)

>76E10E8 H-CDR1
GFSLTNYGVH (SEQ ID NO: 55)

>89A12B8 H-CDR1
GFNIKDDYIH (SEQ ID NO: 56)

Heavy chain CDR-2 (H-CDR2) Amino Acid Sequences

>33D10B12 H-CDR2
EILPSTGRTNYNENFKG (SEQ ID NO: 57)

>172C8B12 H-CDR2
RVNPSNGDTKYNQNFKG (SEQ ID NO: 58)

>67E7E8 H-CDR2
RIDPANGNTKYAPKFQD (SEQ ID NO: 59)

>78C8D1 H-CDR2
VIWAGGPTNYNSALMS (SEQ ID NO: 60)

>81A1D1 H-CDR2
VIWTGITTNYNSALIS (SEQ ID NO: 61)

>81B4E11 H-CDR2
EINPGNVRTNYNENF (SEQ ID NO: 62)

>73C5C10 H-CDR2
VIWSDGSTDFNAPFKS (SEQ ID NO: 63)

>73F6F8 H-CDR2
VIWSDGSTDYNAPFKS (SEQ ID NO: 64)

>76E10E8 H-CDR2
VIWPVGSTNYNSALMS (SEQ ID NO: 65)

>89A12B8 H-CDR2
RIDPANGNTKYDPRFQD (SEQ ID NO: 66)

Heavy chain CDR-3 (H-CDR3) Amino Acid Sequences

>33D10B12 H-CDR3
VYFGNPWFAY (SEQ ID NO: 67)

>172C8B12 H-CDR3
TKNFYSSYSYDDAMDY (SEQ ID NO: 68)

>67E7E8 H-CDR3
SFPNNYYSYDDAFAY (SEQ ID NO: 69)

>78C8D1 H-CDR3
QIYYSTLVDY (SEQ ID NO: 70)

-continued

```
>81A1D1 H-CDR3
GTGTGFYYAMDY (SEQ ID NO: 71)

>81B4E11 H-CDR3
VFYGEPYFPY (SEQ ID NO: 72)

>73C5C10 H-CDR3
KGGYSGSWFAY (SEQ ID NO: 73)

>73F6F8 H-CDR3
KGGYSGSWFAY (SEQ ID NO: 73)

>76E10E8 H-CDR3
MDWDDFFDY (SEQ ID NO: 74)

>89A12B8 H-CDR3
SFPDNYYSYDDAFAY (SEQ ID NO: 75)
```

Anti-IL-36R Mouse CDR Sequences

A summary of the CDR sequences of the lead mouse 20 antibodies is shown below:

| Antibody | H-CDR Sequences | L-CDR Sequences |
|---|---|---|
| 33D10 | GNTVTSYWMH (H-CDR1) SEQ ID No: 48<br>EILPSTGRTNYNENFKG (H-CDR2) SEQ ID No: 57<br>VYFGNPWFAY (H-CDR3) SEQ ID No: 67 | TASSSVSSSYLH (L-CDR1) SEQ ID No: 21<br>STSNLAS (L-CDR2) SEQ ID No: 30<br>HQHHRSPVT (L-CDR3) SEQ ID No: 39 |
| 172C8 | GYTFTDNYMN (H-CDR1) SEQ ID No: 49<br>RVNPSNGDTKYNQNFKG (H-CDR2) SEQ ID No: 58<br>TKNFYSSYSYDDAMDY (H-CDR3) SEQ ID No: 68 | LASQTIGTWLA (L-CDR1) SEQ ID No: 22<br>AATSLAD (L-CDR2) SEQ ID No: 31<br>QQVYTTPLT (L-CDR3) SEQ ID No: 40 |
| 67E7 | GFNIKDDYIH (H-CDR1) SEQ ID No: 50<br>RIDPANGNTKYAPKFQD (H-CDR2) SEQ ID No: 59<br>SFPNNYYSYDDAFAY (H-CDR3) SEQ ID No: 69 | LASQTIGTWLG (L-CDR1) SEQ ID No: 23<br>RSTTLAD (L-CDR2) SEQ ID No: 32<br>QQLYSAPYT (L-CDR3) SEQ ID No: 41 |
| 78C8 | GFSLTKFGVH (H-CDR1) SEQ ID No: 51<br>VIWAGGPTNYNSALMS (H-CDR2) SEQ ID No: 60<br>QIYYSTLVDY (H-CDR3) SEQ ID No: 70 | RSSQNIVHSNGNTYLQ (L-CDR1) SEQ ID No: 24<br>KVSNRFS (L-CDR2) SEQ ID No: 33<br>FQGSHVPFT (L-CDR3) SEQ ID No: 42 |
| 81A1 | GFSLSSYEIN (H-CDR1) SEQ ID No: 52<br>VIWTGITTNYNSALIS (H-CDR2) SEQ ID No: 61<br>GTGTGFYYAMDY (H-CDR3) SEQ ID No: 71 | RASQDIYKYLN (L-CDR1) SEQ ID No: 25<br>YTSGLHS (L-CDR2) SEQ ID No: 34<br>QQDSKFPWT (L-CDR3) SEQ ID No: 43 |
| 81B4 | GYSFTSSWIH (H-CDR1) SEQ ID No: 53<br>EINPGNVRTNYNENF (H-CDR2) SEQ ID No: 62<br>VFYGEPYFPY (H-CDR3) SEQ ID No: 72 | TASSSVSSSYFH (L-CDR1) SEQ ID No: 26<br>RTSNLAS (L-CDR2) SEQ ID No: 35<br>HQFHRSPLT (L-CDR3) SEQ ID No: 44 |
| 73C5 | GFSLTNYAVH (H-CDR1) SEQ ID No: 54<br>VIWSDGSTDFNAPFKS (H-CDR2) SEQ ID No: 63<br>KGGYSGSWFAY (H-CDR3) SEQ ID No: 73 | KASQDVGTNVL (L-CDR1) SEQ ID No: 27<br>SASYRHS (L-CDR2) SEQ ID No: 36<br>QQYSRYPLT (L-CDR3) SEQ ID No: 45 |

| Antibody | H-CDR Sequences | L-CDR Sequences |
| --- | --- | --- |
| 73F6 | GFSLTNYAVH (H-CDR1) SEQ ID No: 54<br>VIWSDGSTDYNAPFKS (H-CDR2) SEQ ID No: 64<br>KGGYSGSWFAY (H-CDR3) SEQ ID No: 73 | KASQDVGTNVL (L-CDR1) SEQ ID No: 27<br>SASYRHS (L-CDR2) SEQ ID No: 36<br>QQYSRYPLT (L-CDR3) SEQ ID No: 45 |
| 76E10 | GFSLTNYGVH (H-CDR1) SEQ ID No: 55<br>VIWPVGSTNYNSALMS (H-CDR2) SEQ ID No: 65<br>MDWDDFFDY (H-CDR3) SEQ ID No: 74 | KASQNVGRAVA (L-CDR1) SEQ ID No: 28<br>SASNRYT (L-CDR2) SEQ ID No: 37<br>QQYSSYPLT (L-CDR3) SEQ ID No: 46 |
| 89A12 | GFNIKDDYIH (H-CDR1) SEQ ID No: 56<br>RIDPANGNTKYDPRFQD (H-CDR2) SEQ ID No: 66<br>SFPDNYYSYDDAFAY (H-CDR3) SEQ ID No: 75 | LASQTIGTWLG (L-CDR1) SEQ ID No: 29<br>RATSLAD (L-CDR2) SEQ ID No: 38<br>QQLYSGPYT (L-CDR3) SEQ ID No: 47 |

Anti-IL-36R Humanized Antibody Sequences

Human framework sequences were selected for the mouse leads based on the framework homology, CDR structure, conserved canonical residues, conserved interface packing residues and other parameters to produce humanized variable regions.

Representative humanized variable regions derived from antibodies 81B4 and 73C5 are shown below.

```
Light Chain Variable Region (VK) Amino Acid Sequences

>81B4vK32_3 vK protein
EIVLTQSPGTLSLSPGERATMSCTASSSVSSSYFHWYQQKPGQAPRLLIYRTSTLASGI
PDRFSGSGSGTDFTLTISRLEPEDAATYYCHQFHRSPLTFGQGTKLEIK (SEQ ID NO:
76)

>81B4vK32_105 vK protein
EIVLTQSPGTLSLSPGERATMSCTASSSVSSSYFHWYQQKPGQAPRLLIYRTSILASGV
PDRFSGSGSGTDFTLTISRLEPEDFATYYCHQFHRSPLTFGQGTKLEIK (SEQ ID NO:
77)

>81B4vK32_116 vK protein
EIVLTQSPGTLSLSPGERATMSCTASSSVSSSYFHWYQQKPGQAPRLWIYRTSRLASG
VPDRFSGSGSGTDFTLTISRLEPEDAATYYCHQFHRSPLTFGQGTKLEIK (SEQ ID NO:
78)

>81B4vK32_127 vK protein
EIVLTQSPGTLSLSPGERATMTCTASSSVSSSYFHWYQQKPGQAPRLLIYRTSRLASG
VPDRFSGSGSGTDFTLTISRLEPEDFAVYYCHQFHRSPLTFGQGTKLEIK (SEQ ID NO:
79)

>81B4vK32_138 vK protein
QIVLTQSPGTLSLSPGERATMTCTASSSVSSSYFHWYQQKPGQAPRLWIYRTSRLASG
VPDRFSGSGSGTDFTLTISRLEPEDAATYYCHQFHRSPLTFGAGTKLEIK (SEQ ID NO:
80)

>81B4vK32_140 vK protein
QIVLTQSPGTLSLSPGERVTMSCTASSSVSSSYFHWYQQKPGQAPRLLIYRTSQLASGI
PDRFSGSGSGTDFTLTISRLEPEDAATYYCHQFHRSPLTFGQGTKLEIK (SEQ ID NO:
81)

>81B4vK32_141 vK protein
QIVLTQSPGTLSLSPGERATMTCTASSSVSSSYFHWYQQKPGQAPRLLIYRTSKLASG
VPDRFSGSGSGTDFTLTISRLEPEDFATYYCHQFHRSPLTFGQGTKLEIK (SEQ ID NO:
82)

>81B4vK32_147 vK protein
EIVLTQSPGTLSLSPGERATMSCTASSSVSSSYFHWYQQKPGQAPRLLIYRTSHLASGI
PGRFSGSGSGTDFTLTISRLEPEDAAVYYCHQFHRSPLTFGQGTKLEIK (SEQ ID NO:
83)

>73C5vK39_2 vK protein
EIVMTQSPATLSVSPGVRATLSCKASQDVGTNVLWYQQKPGQAPRPLIYSASYRHSG
IPDRFSGSGSGTEFTLTISSLQSEDFAEYFCQQYSRYPLTFGQGTKLEIK (SEQ ID NO:
84)
```

-continued

>73C5vK39_7 vK protein
EIVMTQSPATLSVSPGVRATLSCKASQDVGTNVLWYQQKPGQAPRPLIYSASYRHSG
IPDRFSGSGSGTEFTLTISSLQSEDFAVYYCQQYSRYPLTFGQGTKLEIK (SEQ ID NO:
85)

>73C5vK39_15 vK protein
EIVMTQSPATLSVSPGVRATLSCKASQDVGTNVLWYQQKPGQAPRPLIYSASYRHSG
IPARFSGSGSGTEFTLTISSLQSEDFAEYYCQQYSRYPLTFGQGTKLEIK (SEQ ID NO:
86)

Heavy Chain Variable Region (VH) Amino Acid Sequences

>81B4vH33_49 vH Protein
QVQLVQSGAEVKKPGASVKVSCKASGYSFTSSWIHWVRQAPGQGLEWIGEINPGNV
RTNYNENFRNKATMTVDTSISTAYMELSRLRSDDTAVYYCAVVFYGEPYFPYWGQ
GTLVTVSS (SEQ ID NO: 87)

>81B4vH33_85T vH Protein
QVQLVQSGAEVKKPGASVKVSCKASGYSFTSSWIHWVRQRPGQGLEWIGEINPGNV
RTNYNENFRNRVTMTVDTSISTAYMELSRLRSDDTAVYYCTVVFYGEPYFPYWGQG
TLVTVSS (SEQ ID NO: 88)

>81B4vH33_90 vH Protein
QVQLVQSGAEVKKPGASVKVSCKASGYSFTSSWIHWVKQAPGQGLEWMGEINPGN
VRTNYNENFRNKVTMTVDTSISTAYMELSRLRSDDTAVYYCTVVFYGEPYFPYWGQ
GTLVTVSS (SEQ ID NO: 89)

>81B4vH33_93 vH Protein
QVQLVQSGAEVKKPGASVKVSCKASGYSFTSSWIHWVRQRPGQGLEWMGEINPGN
VRTNYNENFRNRATLTRDTSISTAYMELSRLRSDDTAVYYCAVVFYGEPYFPYWGQ
GTLVTVSS (SEQ ID NO: 90)

>81B4vH50_22 vH Protein
QVQLVQSGAEVKKPGASVKVSCKASGYSFTSSWIHWVRQRPGQGLEWMGEILPGV
VRTNYNENFRNKVTMTVDTSISTAYMELSRLRSDDTAVYYCTVVFYGEPYFPYWGQ
GTLVTVSS (SEQ ID NO: 91)

>81B4vH50_30 vH Protein
QVQLVQSGAEVKKPGASVKVSCKASGYSFTSSWIHWVRQRPGQGLEWIGEINPGAV
RTNYNENFRNRVTMTVDTSISTAYMELSRLRSDDTAVYYCTVVFYGEPYFPYWGQG
TLVTVSS (SEQ ID NO: 92)

>81B4vH51_13 vH Protein
QVQLVQSGAEVKKPGASVKVSCKASGYSFTSSWIHWVRQAPGQGLEWIGEINPGLV
RTNYNENFRNKVTMTVDTSISTAYMELSRLRSDDTAVYYCAVVFYGEPYFPYWGQ
GTLVTVSS (SEQ ID NO: 93)

>81B4vH51_15 vH Protein
QVQLVQSGAEVKKPGASVKVSCKASGYSFTSSWIHWVRQAPGQGLEWIGEINPGAV
RTNYNENFRNKVTMTVDTSISTAYMELSRLRSDDTAVYYCAVVFYGEPYFPYWGQ
GTLVTVSS (SEQ ID NO: 94)

>81B4vH52_83 vH Protein
QVQLVQSGAEVKKPGASVKVSCKASGYSFTSSWIHWVRQAPGQGLEWIGEINPGSV
RTNYNENFRNKATMTVDTSISTAYMELSRLRSDDTAVYYCAVVFYGEPYFPYWGQ
GTLVTVSS (SEQ ID NO: 95)

>73C5vH46_4 vH Protein
QVQLQESGPGLVKPSETLSITCTVSGFSLTDYAVHWIRQPPGKGLEWIGVIWSDGSTD
YNAPFKSRVTINKDTSKSQVSFKMSSVQAADTAVYYCARKGGYSGSWFAYWGQGT
LVTVSS (SEQ ID NO: 96)

>73C5vH46_19 vH Protein
QVQLQESGPGLVKPSETLSITCTVSGFSLTDYAVHWIRQPPGKGLEWIGVIWSDGSTD
YNAPFKSRVTISKDTSKNQVSLKMNSLTTDDTAVYYCARKGGYSGSWFAYWGQGT
LVTVSS (SEQ ID NO: 97)

>73C5vH46_40 vH Protein
QVQLQESGPGLVKPSETLSITCTVSGFSLTDYAVHWIRQPPGKGLEWIGVIWSDGSTD
YNAPFKSRVTISKDNSKSQVSLKMNSVTVADTAVYYCARKGGYSGSWFAYWGQGT
LVTVSS (SEQ ID NO: 98)

>73C5vH47_65 vH Protein
QVQLQESGPGLVKPSETLSITCTVSGFSLTDYAVHWVRQPPGKGLEWIGVIWSDGST
DYNAPFKSRVTISKDTSKNQVSFKLSSVTVDDTAVYYCARKGGYSGSWFAYWGQG
TLVTVSS (SEQ ID NO: 99)

```
>73C5vH47_77 vH Protein
QVQLQESGPGLVAPSETLSLTCTVSGFSLTDYAVHWIRQFPGKGLEWIGVIWSDGST
DFNAPFKSRVTISKDTSKNQVSFKLSSVTTDDTAVYYCARKGGYSGSWFAYWGQGT
LVTVSS (SEQ ID NO: 100)

>73C5vH58_91 vH Protein
QVQLQESGPGLVKPSETLSITCTVSGFSLTDYAVHWIRQPPGKGLEWIGVIWSDGSTD
YNAPFKSRVTISKDNSKSQVSFKMSSVTADDTAVYYCARKGGYSGSWFAYWGQGT
LVTVSS (SEQ ID NO: 101)
```

The CDR sequences from the humanized variable regions derived from antibodies 81B4 and 73C5 shown above are depicted below.

L-CDR1 Amino Acid Sequences

```
>81B4vK32_3 L-CDR1
TASSSVSSSYFH (SEQ ID NO: 26)

>81B4vK32_105 L-CDR1
TASSSVSSSYFH (SEQ ID NO: 26)

>81B4vK32_116 L-CDR1
TASSSVSSSYFH (SEQ ID NO: 26)

>81B4vK32_127 L-CDR1
TASSSVSSSYFH (SEQ ID NO: 26)

>81B4vK32_138 L-CDR1
TASSSVSSSYFH (SEQ ID NO: 26)

>81B4vK32_140 L-CDR1
TASSSVSSSYFH (SEQ ID NO: 26)

>81B4vK32_141 L-CDR1
TASSSVSSSYFH (SEQ ID NO: 26)

>81B4vK32_147 L-CDR1
TASSSVSSSYFH (SEQ ID NO: 26)

>73C5vK39_2 L-CDR1
KASQDVGTNVL (SEQ ID NO: 27)

>73C5vK39_7 L-CDR1
KASQDVGTNVL (SEQ ID NO: 27)

>73C5vK39_15 L-CDR1
KASQDVGTNVL (SEQ ID NO: 27)
```

L-CDR2 Amino Acid Sequences

```
>81B4vK32_3 L-CDR2 (SEQ ID 102)
RTSTLAS

>81B4vK32_105 L-CDR2 (SEQ ID 103)
RTSILAS

>81B4vK32_116 L-CDR2 (SEQ ID 104)
RTSRLAS

>81B4vK32_127 L-CDR2 (SEQ ID 104)
RTSRLAS

>81B4vK32_138 L-CDR2 (SEQ ID 104)
RTSRLAS

>81B4vK32_140 L-CDR2 (SEQ ID 105)
RTSQLAS

>81B4vK32_141 L-CDR2 (SEQ ID 106)
RTSKLAS

>81B4vK32_147 L-CDR2 (SEQ ID 140)
RTSHLAS

>73C5vK39_2 L-CDR2
SASYRHS (SEQ ID NO: 36)

>73C5vK39_7 L-CDR2
SASYRHS (SEQ ID NO: 36)

>73C5vK39_15 L-CDR2
SASYRHS (SEQ ID NO: 36)
```

L-CDR3 Amino Acid Sequences

```
>81B4vK32_3 L-CDR3
HQFHRSPLT (SEQ ID NO: 44)

>81B4vK32_105 L-CDR3
HQFHRSPLT (SEQ ID NO: 44)

>81B4vK32_116 L-CDR3
HQFHRSPLT (SEQ ID NO: 44)

>81B4vK32_127 L-CDR3
HQFHRSPLT (SEQ ID NO: 44)

>81B4vK32_138 L-CDR3
HQFHRSPLT (SEQ ID NO: 44)

>81B4vK32_140 L-CDR3
HQFHRSPLT (SEQ ID NO: 44)

>81B4vK32_141 L-CDR3
HQFHRSPLT (SEQ ID NO: 44)

>81B4vK32_147 L-CDR3
HQFHRSPLT (SEQ ID NO: 44)

>73C5vK39_2 L-CDR3
QQYSRYPLT (SEQ ID NO: 45)

>73C5vK39_7 L-CDR3
QQYSRYPLT (SEQ ID NO: 45)

>73C5vK39_15 L-CDR3
QQYSRYPLT (SEQ ID NO: 45)
```

H-CDR1 Amino Acid Sequences

```
>81B4vH33_49 H-CDR1
GYSFTSSWIH (SEQ ID NO: 53)

>81B4vH33_85T H-CDR1
GYSFTSSWIH (SEQ ID NO: 53)

>81B4vH33_90 H-CDR1
GYSFTSSWIH (SEQ ID NO: 53)

>81B4vH33_93 H-CDR1
GYSFTSSWIH (SEQ ID NO: 53)

>81B4vH50_22 H-CDR1
GYSFTSSWIH (SEQ ID NO: 53)

>81B4vH50_30 H-CDR1
GYSFTSSWIH (SEQ ID NO: 53)
```

```
>81B4vH51_13 H-CDR1
GYSFTSSWIH (SEQ ID NO: 53)

>81B4vH51_15 H-CDR1
GYSFTSSWIH (SEQ ID NO: 53)

>81B4vH52_83 H-CDR1
GYSFTSSWIH (SEQ ID NO: 53)

>73C5vH46_4 H-CDR1
GFSLTDYAVH (SEQ ID NO: 107)

>73C5vH46_19 H-CDR1
GFSLTDYAVH (SEQ ID NO: 107)

>73C5vH46_40 H-CDR1
GFSLTDYAVH (SEQ ID NO: 107)

>73C5vH47_65 H-CDR1
GFSLTDYAVH (SEQ ID NO: 107)

>73C5vH47_77 H-CDR1
GFSLTDYAVH (SEQ ID NO: 107)

>73C5vH58_91 H-CDR1
GFSLTDYAVH (SEQ ID NO: 107)
```

H-CDR2 Amino Acid Sequences

```
>81B4vH33_49 H-CDR2
EINPGNVRTNYNENF (SEQ ID NO: 62)

>81B4vH33_85T H-CDR2
EINPGNVRTNYNENF (SEQ ID NO: 62)

>81B4vH33_90 H-CDR2
EINPGNVRTNYNENF (SEQ ID NO: 62)

>81B4vH33_93 H-CDR2
EINPGNVRTNYNENF (SEQ ID NO: 62)

>81B4vH50_22 H-CDR2
EILPGVVRTNYNENF (SEQ ID NO: 108)

>81B4vH50_30 H-CDR2
EINPGAVRTNYNENF (SEQ ID NO: 109)

>81B4vH51_13 H-CDR2
EINPGLVRTNYNENF (SEQ ID NO: 110)

>81B4vH51_15 H-CDR2
EINPGAVRTNYNENF (SEQ ID NO: 109)

>81B4vH52_83 H-CDR2
EINPGSVRTNYNENF (SEQ ID NO: 111)

>73C5vH46_4 H-CDR2
VIWSDGSTDYNAPFKS (SEQ ID NO: 64)

>73C5vH46_19 H-CDR2
VIWSDGSTDYNAPFKS (SEQ ID NO: 64)

>73C5vH46_40 H-CDR2
VIWSDGSTDYNAPFKS (SEQ ID NO: 64)

>73C5vH47_65 H-CDR2
VIWSDGSTDYNAPFKS (SEQ ID NO: 64)

>73C5vH47_77 H-CDR2
VIWSDGSTDFNAPFKS (SEQ ID NO: 63)

>73C5vH58_91 H-CDR2
VIWSDGSTDYNAPFKS (SEQ ID NO: 64)
```

H-CDR3 Amino Acid Sequences

```
>81B4vH33_49 H-CDR3
VFYGEPYFPY (SEQ ID NO: 72)

>81B4vH33_85T H-CDR3
VFYGEPYFPY (SEQ ID NO: 72)

>81B4vH33_90 H-CDR3
VFYGEPYFPY (SEQ ID NO: 72)

>81B4vH33_93 H-CDR3
VFYGEPYFPY (SEQ ID NO: 72)

>81B4vH50_22 H-CDR3
VFYGEPYFPY (SEQ ID NO: 72)

>81B4vH50_30 H-CDR3
VFYGEPYFPY (SEQ ID NO: 72)

>81B4vH51_13 H-CDR3
VFYGEPYFPY (SEQ ID NO: 72)

>81B4vH51_15 H-CDR3
VFYGEPYFPY (SEQ ID NO: 72)

>81B4vH52_83 H-CDR3
VFYGEPYFPY (SEQ ID NO: 72)

>73C5vH46_4 H-CDR3
KGGYSGSWFAY (SEQ ID NO: 73)

>73C5vH46_19 H-CDR3
KGGYSGSWFAY (SEQ ID NO: 73)

>73C5vH46_40 H-CDR3
KGGYSGSWFAY (SEQ ID NO: 73)

>73C5vH47_65 H-CDR3
KGGYSGSWFAY (SEQ ID NO: 73)

>73C5vH47_77 H-CDR3
KGGYSGSWFAY (SEQ ID NO: 73)

>73C5vH58_91 H-CDR3
KGGYSGSWFAY (SEQ ID NO: 73)
```

In one aspect, a variable region of the present invention is linked to a constant region. For example, a variable region of the present invention is linked to a constant region shown below to form a heavy chain or a light chain of an antibody.

Heavy Chain Constant region linked downstream of a humanized variable heavy region:

```
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRV
EPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLT
VDKSRWQQGNVFSCSVMHEALHNHYTQKSLSLSPGK (SEQ ID
NO: 112)
```

Light Chain Constant region linked downstream of a humanized variable light region:

```
RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPV
TKSFNRGEC (SEQ ID NO: 113)
```

Representative light chain and heavy chain sequences of the present invention are shown below (humanized variable regions derived from antibodies 81B4 and 73C5 linked to constant regions).

Light Chain Amino Acid Sequences

>81B4vK32_3 Light Chain
EIVLTQSPGTLSLSPGERATMSCTASSSVSSSYFHWYQQKPGQAPRLLIYRTSTLASGI
PDRFSGSGSGTDFTLTISRLEPEDAATYYCHQFHRSPLTFGQGTKLEIKRTVAAPSVFI
FPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 114)

>81B4vK32_105 Light Chain
EIVLTQSPGTLSLSPGERATMSCTASSSVSSSYFHWYQQKPGQAPRLLIYRTSILASGV
PDRFSGSGSGTDFTLTISRLEPEDFATYYCHQFHRSPLTFGQGTKLEIKRTVAAPSVFIF
PPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC (SEQ ID NO: 115)

>81B4vK32_116 Light Chain
EIVLTQSPGTLSLSPGERATMSCTASSSVSSSYFHWYQQKPGQAPRLWIYRTSRLASG
VPDRFSGSGSGTDFTLTISRLEPEDAATYYCHQFHRSPLTFGQGTKLEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 116)

>81B4vK32_127 Light Chain
EIVLTQSPGTLSLSPGERATMTCTASSSVSSSYFHWYQQKPGQAPRLLIYRTSRLASG
VPDRFSGSGSGTDFTLTISRLEPEDFAVYYCHQFHRSPLTFGQGTKLEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 117)

>81B4vK32_138 Light Chain
QIVLTQSPGTLSLSPGERATMTCTASSSVSSSYFHWYQQKPGQAPRLWIYRTSRLASG
VPDRFSGSGSGTDFTLTISRLEPEDAATYYCHQFHRSPLTFGAGTKLEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 118)

>81B4vK32_140 Light Chain
QIVLTQSPGTLSLSPGERVTMSCTASSSVSSSYFHWYQQKPGQAPRLLIYRTSQLASGI
PDRFSGSGSGTDFTLTISRLEPEDAATYYCHQFHRSPLTFGQGTKLEIKRTVAAPSVFI
FPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 119)

>81B4vK32_141 Light Chain
QIVLTQSPGTLSLSPGERATMTCTASSSVSSSYFHWYQQKPGQAPRLLIYRTSKLASG
VPDRFSGSGSGTDFTLTISRLEPEDFATYYCHQFHRSPLTFGQGTKLEIKRTVAAPSVF
IFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 120)

>81B4vK32_147 Light Chain
EIVLTQSPGTLSLSPGERATMSCTASSSVSSSYFHWYQQKPGQAPRLLIYRTSHLASGI
PGRFSGSGSGTDFTLTISRLEPEDAAVYYCHQFHRSPLTFGQGTKLEIKRTVAAPSVFI
FPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 121)

>73C5vK39_2 Light Chain
EIVMTQSPATLSVSPGVRATLSCKASQDVGTNVLWYQQKPGQAPRPLIYSASYRHSG
IPDRFSGSGSGTEFTLTISSLQSEDFAEYFCQQYSRYPLTFGQGTKLEIKRTVAAPSVFI
FPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 122)

>73C5vK39_7 Light Chain
EIVMTQSPATLSVSPGVRATLSCKASQDVGTNVLWYQQKPGQAPRPLIYSASYRHSG
IPDRFSGSGSGTEFTLTISSLQSEDFAVYYCQQYSRYPLTFGQGTKLEIKRTVAAPSVFI
FPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 123)

>73C5vK39_15 Light Chain
EIVMTQSPATLSVSPGVRATLSCKASQDVGTNVLWYQQKPGQAPRPLIYSASYRHSG
IPARFSGSGSGTEFTLTISSLQSEDFAEYYCQQYSRYPLTFGQGTKLEIKRTVAAPSVFI
FPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 124)

Heavy Chain Amino Acid Sequences

>81B4vH33_49 Heavy Chain
QVQLVQSGAEVKKPGASVKVSCKASGYSFTSSWIHWVRQAPGQGLEWIGEINPGNV
RTNYNENFRNKATMTVDTSISTAYMELSRLRSDDTAVYYCAVVFYGEPYFPYWGQ
GTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRVEPKSCDKT
HTCPPCPAPEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK
(SEQ ID NO: 125)

```
>81B4vH33_85T Heavy Chain
QVQLVQSGAEVKKPGASVKVSCKASGYSFTSSWIHWVRQRPGQGLEWIGEINPGNV
RTNYNENFRNRVTMTVDTSISTAYMELSRLRSDDTAVYYCTVVFYGEPYFPYWGQG
TLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHT
CPPCPAPEAAGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK (SEQ
ID NO: 126)

>81B4vH33_90 Heavy Chain
QVQLVQSGAEVKKPGASVKVSCKASGYSFTSSWIHWVKQAPGQGLEWMGEINPGN
VRTNYNENFRNKVTMTVDTSISTAYMELSRLRSDDTAVYYCTVVFYGEPYFPYWGQ
GTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRVEPKSCDKT
HTCPPCPAPEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK
(SEQ ID NO: 127)

>81B4vH33_93 Heavy Chain
QVQLVQSGAEVKKPGASVKVSCKASGYSFTSSWIHWVRQRPGQGLEWMGEINPGN
VRTNYNENFRNRATLTRDTSISTAYMELSRLRSDDTAVYYCAVVFYGEPYFPYWGQ
GTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRVEPKSCDKT
HTCPPCPAPEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK
(SEQ ID NO: 128)

>81B4vH50_22 Heavy Chain
QVQLVQSGAEVKKPGASVKVSCKASGYSFTSSWIHWVRQRPGQGLEWMGEILPGV
VRTNYNENFRNKVTMTVDTSISTAYMELSRLRSDDTAVYYCTVVFYGEPYFPYWGQ
GTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRVEPKSCDKT
HTCPPCPAPEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK
(SEQ ID NO: 129)

>81B4vH50_30 Heavy Chain
QVQLVQSGAEVKKPGASVKVSCKASGYSFTSSWIHWVRQRPGQGLEWIGEINPGAV
RTNYNENFRNRVTMTVDTSISTAYMELSRLRSDDTAVYYCTVVFYGEPYFPYWGQG
TLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHT
CPPCPAPEAAGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK (SEQ
ID NO: 130)

>81B4vH51_13 Heavy Chain
QVQLVQSGAEVKKPGASVKVSCKASGYSFTSSWIHWVRQAPGQGLEWIGEINPGLV
RTNYNENFRNKVTMTVDTSISTAYMELSRLRSDDTAVYYCAVVFYGEPYFPYWGQ
GTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRVEPKSCDKT
HTCPPCPAPEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK
(SEQ ID NO: 131)

>81B4vH51_15 Heavy Chain
QVQLVQSGAEVKKPGASVKVSCKASGYSFTSSWIHWVRQAPGQGLEWIGEINPGAV
RTNYNENFRNKVTMTVDTSISTAYMELSRLRSDDTAVYYCAVVFYGEPYFPYWGQ
GTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRVEPKSCDKT
HTCPPCPAPEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK
(SEQ ID NO: 132)
```

-continued

>81B4vH52_83 Heavy Chain
QVQLVQSGAEVKKPGASVKVSCKASGYSFTSSWIHWVRQAPGQGLEWIGEINPGSV
RTNYNENFRNKATMTVDTSISTAYMELSRLRSDDTAVYYCAVVFYGEPYFPYWGQ
GTLVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKRVEPKSCDKT
HTCPPCPAPEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTI
SKAKGQPREPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSLSPGK
(SEQ ID NO: 133)

>73C5vH46_4 Heavy Chain
QVQLQESGPGLVKPSETLSITCTVSGFSLTDYAVHWIRQPPGKGLEWIGVIWSDGSTD
YNAPFKSRVTINKDTSKSQVSFKMSSVQAADTAVYYCARKGGYSGSWFAYWGQGT
LVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKSCDKTHTC
PPCPAPEAAGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK (SEQ
ID NO: 134)

>73C5vH46_19 Heavy Chain
QVQLQESGPGLVKPSETLSITCTVSGFSLTDYAVHWIRQPPGKGLEWIGVIWSDGSTD
YNAPFKSRVTISKDTSKNQVSLKMNSLTTDDTAVYYCARKGGYSGSWFAYWGQGT
LVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKSCDKTHTC
PPCPAPEAAGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK (SEQ
ID NO: 135)

>73C5vH46_40 Heavy Chain
QVQLQESGPGLVKPSETLSITCTVSGFSLTDYAVHWIRQPPGKGLEWIGVIWSDGSTD
YNAPFKSRVTISKDNSKSQVSLKMNSVTVADTAVYYCARKGGYSGSWFAYWGQGT
LVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKSCDKTHTC
PPCPAPEAAGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK (SEQ
ID NO: 136)

>73C5vH47_65 Heavy Chain
QVQLQESGPGLVKPSETLSITCTVSGFSLTDYAVHWVRQPPGKGLEWIGVIWSDGST
DYNAPFKSRVTISKDTSKNQVSFKLSSVTVDDTAVYYCARKGGYSGSWFAYWGQG
TLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHT
CPPCPAPEAAGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK (SEQ
ID NO: 137)

>73C5vH47_77 Heavy Chain
QVQLQESGPGLVAPSETLSLTCTVSGFSLTDYAVHWIRQFPGKGLEWIGVIWSDGST
DFNAPFKSRVTISKDTSKNQVSFKLSSVTTDDTAVYYCARKGGYSGSWFAYWGQGT
LVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKSCDKTHTC
PPCPAPEAAGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK (SEQ
ID NO: 138)

>73C5vH58_91 Heavy Chain
QVQLQESGPGLVKPSETLSITCTVSGFSLTDYAVHWIRQPPGKGLEWIGVIWSDGSTD
YNAPFKSRVTISKDNSKSQVSFKMSSVTADDTAVYYCARKGGYSGSWFAYWGQGT
LVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKSCDKTHTC
PPCPAPEAAGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK (SEQ
ID NO: 139)

The CDRs listed above are defined using the Chothia numbering system (Al-Lazikani et al., (1997) JMB 273, 927-948).

In one aspect, an antibody of the present invention comprises 3 light chain CDRs and 3 heavy chain CDRs, for example as set forth above.

In one aspect, an antibody of the present invention comprises a light chain and a heavy chain variable region as set forth above. In one aspect, a light chain variable region of the invention is fused to a light chain constant region, for example a kappa or lambda constant region. In one aspect, a heavy chain variable region of the invention is fused to a heavy chain constant region, for example IgA, IgD, IgE, IgG or IgM, in particular, $IgG_1$, $IgG_2$, $IgG_3$ or $IgG_4$.

The present invention provides an anti-IL-36R antibody comprising a light chain comprising the amino acid sequence of SEQ ID NO: 115; and a heavy chain comprising the amino acid sequence of SEQ ID NO: 125 (Antibody B1).

The present invention provides an anti-IL-36R antibody comprising a light chain comprising the amino acid sequence of SEQ ID NO: 115; and a heavy chain comprising the amino acid sequence of SEQ ID NO: 126 (Antibody B2).

The present invention provides an anti-IL-36R antibody comprising a light chain comprising the amino acid sequence of SEQ ID NO: 115; and a heavy chain comprising the amino acid sequence of SEQ ID NO: 127 (Antibody B3).

The present invention provides an anti-IL-36R antibody comprising a light chain comprising the amino acid sequence of SEQ ID NO: 118; and a heavy chain comprising the amino acid sequence of SEQ ID NO: 125 (Antibody B4).

The present invention provides an anti-IL-36R antibody comprising a light chain comprising the amino acid sequence of SEQ ID NO: 118; and a heavy chain comprising the amino acid sequence of SEQ ID NO: 126 (Antibody B5).

The present invention provides an anti-IL-36R antibody comprising a light chain comprising the amino acid sequence of SEQ ID NO: 118; and a heavy chain comprising the amino acid sequence of SEQ ID NO: 127 Antibody B6).

The present invention provides an anti-IL-36R antibody comprising a light chain comprising the amino acid sequence of SEQ ID NO: 123; and a heavy chain comprising the amino acid sequence of SEQ ID NO: 138 (Antibody C3).

The present invention provides an anti-IL-36R antibody comprising a light chain comprising the amino acid sequence of SEQ ID NO: 123; and a heavy chain comprising the amino acid sequence of SEQ ID NO: 139 (Antibody C2).

The present invention provides an anti-IL-36R antibody comprising a light chain comprising the amino acid sequence of SEQ ID NO: 124; and a heavy chain comprising the amino acid sequence of SEQ ID NO: 138 (Antibody C1)

Representative antibodies of the present invention are shown below.

TABLE A

| Antibody | Light Chain Sequences | Heavy Chain Sequences |
|---|---|---|
| B1 | EIVLTQSPGTLSLSPGERATMSCTASSSVSSSYFHWYQQKPGQAPRLLIYRTSILASGVPDRFSGSGSGTDFTLTISRLEPEDFATYYCHQFHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 115) | QVQLVQSGAEVKKPGASVKVSCKASGYSFTSSWIHWVRQAPGQGLEWIGEINPGNVRTNYNENFRNKATMTVDTSISTAYMELSRLRSDDTAVYYCAVVFYGEPYFPYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 125) |
| B2 | EIVLTQSPGTLSLSPGERATMSCTASSSVSSSYFHWYQQKPGQAPRLLIYRTSILASGVPDRFSGSGSGTDFTLTISRLEPEDFATYYCHQFHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 115) | QVQLVQSGAEVKKPGASVKVSCKASGYSFTSSWIHWVRQRPGQGLEWIGEINPGNVRTNYNENFRNRVTMTVDTSISTAYMELSRLRSDDTAVYYCTVVFYGEPYFPYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 126) |
| B3 | EIVLTQSPGTLSLSPGERATMSCTASSSVSSSYFHWYQQKPGQAPRLLIYRTSILASGVPDRFSGSGSGTDFTLTISRLEPEDFATYYCHQFHRSPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKV | QVQLVQSGAEVKKPGASVKVSCKASGYSFTSSWIHWVKQAPGQGLEWMGEINPGNVRTNYNENFRNKVTMTVDTSISTAYMELSRLRSDDTAVYYCTVVFYGEPYFPYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTC |

TABLE A-continued

| Antibody | Light Chain Sequences | Heavy Chain Sequences |
|---|---|---|
| | YACEVTHQGLSSPVTKSFNRGEC (SEQ ID NO: 115) | PPCPAPEAAGGPSVFLFPPKPKDTLMISRT PEVTCVVVDVSHEDPEVKFNWYVDGVE VHNAKTKPREEQYNSTYRVVSVLTVLHQ DWLNGKEYKCKVSNKALPAPIEKTISKA KGQPREPQVYTLPPSREEMTKNQVSLTCL VKGFYPSDIAVEWESNGQPENNYKTTPP VLDSDGSFFLYSKLTVDKSRWQQGNVFS CSVMHEALHNHYTQKSLSLSPGK (SEQ ID NO: 127) |
| B4 | QIVLTQSPGTLSLSPGERATMTCTA SSSVSSSYFHWYQQKPGQAPRLWI YRTSRLASGVPDRFSGSGSGTDFT LTISRLEPEDAATYYCHQFHRSPLT FGAGTKLEIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 118) | QVQLVQSGAEVKKPGASVKVSCKASGYS FTSSWIHWVRQAPGQGLEWIGEINPGNV RTNYNENFRNKATMTVDTSISTAYMELS RLRSDDTAVYYCAVVFYGEPYFPYWGQ GTLVTVSSASTKGPSVFPLAPSSKSTSGGT AALGCLVKDYFPEPVTVSWNSGALTSGV HTFPAVLQSSGLYSLSSVVTVPSSSLGTQT YICNVNHKPSNTKVDKRVEPKSCDKTHT CPPCPAPEAAGGPSVFLFPPKPKDTLMISR TPEVTCVVVDVSHEDPEVKFNWYVDGV EVHNAKTKPREEQYNSTYRVVSVLTVLH QDWLNGKEYKCKVSNKALPAPIEKTISK AKGQPREPQVYTLPPSREEMTKNQVSLT CLVKGFYPSDIAVEWESNGQPENNYKTT PPVLDSDGSFFLYSKLTVDKSRWQQGNV FSCSVMHEALHNHYTQKSLSLSPGK (SEQ ID NO: 125) |
| B5 | QIVLTQSPGTLSLSPGERATMTCTA SSSVSSSYFHWYQQKPGQAPRLWI YRTSRLASGVPDRFSGSGSGTDFT LTISRLEPEDAATYYCHQFHRSPLT FGAGTKLEIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 118) | QVQLVQSGAEVKKPGASVKVSCKASGYS FTSSWIHWVRQRPGQGLEWIGEINPGNVR TNYNENFRNRVTMTVDTSISTAYMELSR LRSDDTAVYYCTVVFYGEPYFPYWGQGT LVTVSSASTKGPSVFPLAPSSKSTSGGTAA LGCLVKDYFPEPVTVSWNSGALTSGVHT FPAVLQSSGLYSLSSVVTVPSSSLGTQTYI CNVNHKPSNTKVDKRVEPKSCDKTHTCP PCPAPEAAGGPSVFLFPPKPKDTLMISRTP EVTCVVVDVSHEDPEVKFNWYVDGVEV HNAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFFLYSKLTVDKSRWQQGNVFSCS VMHEALHNHYTQKSLSLSPGK (SEQ ID NO: 126) |
| B6 | QIVLTQSPGTLSLSPGERATMTCTA SSSVSSSYFHWYQQKPGQAPRLWI YRTSRLASGVPDRFSGSGSGTDFT LTISRLEPEDAATYYCHQFHRSPLT FGAGTKLEIKRTVAAPSVFIFPPSD EQLKSGTASVVCLLNNFYPREAK VQWKVDNALQSGNSQESVTEQD SKDSTYSLSSTLTLSKADYEKHKV YACEVTHQGLSSPVTKSFNRGEC (SEQ ID NO: 118) | QVQLVQSGAEVKKPGASVKVSCKASGYS FTSSWIHWVKQAPGQGLEWMGEINPGNV RTNYNENFRNKVTMTVDTSISTAYMELS RLRSDDTAVYYCTVVFYGEPYFPYWGQG TLVTVSSASTKGPSVFPLAPSSKSTSGGTA ALGCLVKDYFPEPVTVSWNSGALTSGVH TFPAVLQSSGLYSLSSVVTVPSSSLGTQTY ICNVNHKPSNTKVDKRVEPKSCDKTHTC PPCPAPEAAGGPSVFLFPPKPKDTLMISRT PEVTCVVVDVSHEDPEVKFNWYVDGVE VHNAKTKPREEQYNSTYRVVSVLTVLHQ DWLNGKEYKCKVSNKALPAPIEKTISKA KGQPREPQVYTLPPSREEMTKNQVSLTCL VKGFYPSDIAVEWESNGQPENNYKTTPP VLDSDGSFFLYSKLTVDKSRWQQGNVFS CSVMHEALHNHYTQKSLSLSPGK (SEQ ID NO: 127) |

TABLE B

| Antibody | Light Chain Sequences | Heavy Chain Sequences |
|---|---|---|
| C1 | EIVMTQSPATLSVSPGVRATLSCK ASQDVGTNVLWYQQKPGQAPRPL IYSASYRHSGIPARFSGSGSGTEFTL TISSLQSEDFAEYYCQQYSRYPLTF GQGTKLEIKRTVAAPSVFIFPPSDE | QVQLQESGPGLVAPSETLSLTCTVSGFSL TDYAVHWIRQFPGKGLEWIGVIWSDGST DFNAPFKSRVTISKDTSKNQVSFKLSSVTT DDTAVYYCARKGGYSGSWFAYWGQGTL VTVSSASTKGPSVFPLAPSSKSTSGGTAAL |

TABLE B-continued

| Antibody | Light Chain Sequences | Heavy Chain Sequences |
|---|---|---|
|  | QLKSGTASVVCLLNNFYPREAKV QWKVDNALQSGNSQESVTEQDSK DSTYSLSSTLTLSKADYEKHKVYA CEVTHQGLSSPVTKSFNRGEC (SEQ ID NO: 124) | GCLVKDYFPEPVTVSWNSGALTSGVHTF PAVLQSSGLYSLSSVVTVPSSSLGTQTYIC NVNHKPSNTKVDKRVEPKSCDKTHTCPP CPAPEAAGGPSVFLFPPKPKDTLMISRTPE VTCVVVDVSHEDPEVKFNWYVDGVEVH NAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFPLYSKLTVDKSRWQQGNVFSCS VMHEALHNHYTQKSLSLSPGK (SEQ ID NO: 138) |
| C2 | EIVMTQSPATLSVSPGVRATLSCK ASQDVGTNVLWYQQKPGQAPRPL IYSASYRHSGIPDRFSGSGSGTEFTL TISSLQSEDFAVYYCQQYSRYPLTF GQGTKLEIKRTVAAPSVFIFPPSDE QLKSGTASVVCLLNNFYPREAKV QWKVDNALQSGNSQESVTEQDSK DSTYSLSSTLTLSKADYEKHKVYA CEVTHQGLSSPVTKSFNRGEC (SEQ ID NO: 123) | QVQLQESGPGLVKPSETLSITCTVSGFSLT DYAVHWIRQPPGKGLEWIGVIWSDGSTD YNAPFKSRVTISKDNSKSQVSFKMSSVTA DDTAVYYCARKGGYSGSWFAYWGQGTL VTVSSASTKGPSVFPLAPSSKSTSGGTAAL GCLVKDYFPEPVTVSWNSGALTSGVHTF PAVLQSSGLYSLSSVVTVPSSSLGTQTYIC NVNHKPSNTKVDKRVEPKSCDKTHTCPP CPAPEAAGGPSVFLFPPKPKDTLMISRTPE VTCVVVDVSHEDPEVKFNWYVDGVEVH NAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSFPLYSKLTVDKSRWQQGNVFSCS VMHEALHNHYTQKSLSLSPGK (SEQ ID NO: 139) |
| C3 | EIVMTQSPATLSVSPGVRATLSCK ASQDVGTNVLWYQQKPGQAPRPL IYSASYRHSGIPDRFSGSGSGTEFTL TISSLQSEDFAVYYCQQYSRYPLTF GQGTKLEIKRTVAAPSVFIFPPSDE QLKSGTASVVCLLNNFYPREAKV QWKVDNALQSGNSQESVTEQDSK DSTYSLSSTLTLSKADYEKHKVYA CEVTHQGLSSPVTKSFNRGEC (SEQ ID NO: 123) | QVQLQESGPGLVAPSETLSLTCTVSGFSL TDYAVHWIRQFPGKGLEWIGVIWSDGST DFNAPFKSRVTISKDTSKNQVSFKLSSVTT DDTAVYYCARKGGYSGSWFAYWGQGTL VTVSSASTKGPSVFPLAPSSKSTSGGTAAL GCLVKDYFPEPVTVSWNSGALTSGVHTF PAVLQSSGLYSLSSVVTVPSSSLGTQTYIC NVNHKPSNTKVDKRVEPKSCDKTHTCPP CPAPEAAGGPSVFLFPPKPKDTLMISRTPE VTCVVVDVSHEDPEVKFNWYVDGVEVH NAKTKPREEQYNSTYRVVSVLTVLHQD WLNGKEYKCKVSNKALPAPIEKTISKAK GQPREPQVYTLPPSREEMTKNQVSLTCLV KGFYPSDIAVEWESNGQPENNYKTTPPVL DSDGSPPLYSKLTVDKSRWQQGNVFSCS VMHEALHNHYTQKSLSLSPGK (SEQ ID NO: 138) |

The antibodies of the present invention are useful in methods for the treatment of various diseases or disorders, for example immunological, inflammatory, autoimmune diseases and respiratory diseases in humans. For example, the antibodies of the present invention are useful in methods for the treatment of psoriasis, rheumatoid arthritis, inflammatory bowel disease or psoriatic arthritis. For example, the antibodies of the present invention are useful in methods for the treatment of chronic obstructive pulmonary disorder (COPD) or asthma. For example, the antibodies of the present invention are useful in methods for the treatment of scleroderma, palmoplantar pustulosis, generalized pustular psoriasis, diabetic nephropathy, lupus nephritis, scleroderma, ankylosing spondylitis, deficiency in the IL-36 receptor antagonist autoimmune disease (DITRA), deficiency in the IL-1 receptor antagonist autoimmune disease (DIRA) or cryopyrin associated periodic syndromes (CAPS).

In some aspects, the humanized antibody displays blocking activity, whereby it decreases the binding of IL-36 ligand to IL-36 receptor by at least 45%, by at least 50%, by at least 55%, by at least 60%, by at least 65%, by at least 70%, by at least 75%, by at least 80%, by at least 85%, by at least 90%, or by at least 95%. The ability of an antibody to block binding of IL-36 ligand to the IL-36 receptor can be measured using competitive binding assays known in the art. Alternatively, the blocking activity of an antibody can be measured by assessing the biological effects of IL-36, such as the production of IL-8, IL-6, and GM-CSF to determine if signaling mediated by the IL-36 receptor is inhibited.

In a further aspect, the present invention provides a humanized anti-IL-36R antibody having favorable biophysical properties. In one aspect, a humanized anti-IL-36R antibody of the present invention is present in at least 90% monomer form, or in at least 92% monomer form, or in at least 95% monomer form in a buffer. In a further aspect, a humanized anti-IL-36R antibody of the present invention remains in at least 90% monomer form, or in at least 92% monomer form, or in at least 95% monomer form in a buffer for one month or for four months.

In one aspect, a humanized antibody of the present invention is Antibody B1, Antibody B2, Antibody B3, Antibody B4, Antibody B5, Antibody B6, Antibody C1, Antibody C2, or Antibody C3. Accordingly, in one embodiment, a humanized antibody of the present invention comprises the light chain sequence of SEQ ID NO:115 and the heavy chain sequence of SEQ ID NO:125 (Antibody B1). In another embodiment, a humanized antibody of the present invention comprises the light chain sequence of SEQ ID NO:115 and the heavy chain sequence of SEQ ID NO:126 (Antibody B2). In another embodiment, a humanized antibody of the present invention comprises the light chain sequence of SEQ ID NO:115 and the heavy chain sequence of SEQ ID NO:127 (Antibody B3). In another embodiment, a humanized antibody of the present invention comprises the light chain sequence of SEQ ID NO:118 and the heavy chain sequence of SEQ ID NO:125 (Antibody B4). In another embodiment, a humanized antibody of the present invention comprises the light chain sequence of SEQ ID NO:118 and the heavy chain sequence of SEQ ID NO:126 (Antibody B5). In another embodiment, a humanized antibody of the present invention comprises the light chain sequence of SEQ ID NO:118 and the heavy chain sequence of SEQ ID NO:127 (Antibody B6). In another embodiment, a humanized antibody of the present invention comprises the light chain sequence of SEQ ID NO:124 and the heavy chain sequence of SEQ ID NO:138 (Antibody C1). In another embodiment, a humanized antibody of the present invention comprises the light chain sequence of SEQ ID NO:123 and the heavy chain sequence of SEQ ID NO:139 (Antibody C2). In another embodiment, a humanized antibody of the present invention comprises the light chain sequence of SEQ ID NO:123 and the heavy chain sequence of SEQ ID NO:138 (Antibody C3).

In a further embodiment, a humanized antibody of the present invention consists of the light chain sequence of SEQ ID NO:115 and the heavy chain sequence of SEQ ID NO:125 (Antibody B1). In another embodiment, a humanized antibody of the present invention consists of the light chain sequence of SEQ ID NO:115 and the heavy chain sequence of SEQ ID NO:126 (Antibody B2). In another embodiment, a humanized antibody of the present invention consists of the light chain sequence of SEQ ID NO:115 and the heavy chain sequence of SEQ ID NO:127 (Antibody B3). In another embodiment, a humanized antibody of the present invention consists of the light chain sequence of SEQ ID NO:118 and the heavy chain sequence of SEQ ID NO:125 (Antibody B4). In another embodiment, a humanized antibody of the present invention consists of the light chain sequence of SEQ ID NO:118 and the heavy chain sequence of SEQ ID NO:126 (Antibody B5). In another embodiment, a humanized antibody of the present invention consists of the light chain sequence of SEQ ID NO:118 and the heavy chain sequence of SEQ ID NO:127 (Antibody B6). In another embodiment, a humanized antibody of the present invention consists of the light chain sequence of SEQ ID NO:124 and the heavy chain sequence of SEQ ID NO:138 (Antibody C1). In another embodiment, a humanized antibody of the present invention consists of the light chain sequence of SEQ ID NO:123 and the heavy chain sequence of SEQ ID NO:139 (Antibody C2). In another embodiment, a humanized antibody of the present invention consists of the light chain sequence of SEQ ID NO:123 and the heavy chain sequence of SEQ ID NO:138 (Antibody C3).

In some embodiments, the humanized anti-IL-36R antibodies, including antigen-binding fragments thereof, such as heavy and light chain variable regions, comprise an amino acid sequence of the residues derived from Antibody B1, Antibody B2, Antibody B3, Antibody B4, Antibody B5, Antibody B6, Antibody C1, Antibody C2, or Antibody C3.

In a further embodiment, the present invention provides an anti-IL-36R antibody or antigen-binding fragment thereof that competitively binds to human IL-36R with an antibody of the present invention, for example Antibody B1, Antibody B2, Antibody B3, Antibody B4, Antibody B5, Antibody B6, Antibody C1, Antibody C2 or Antibody C3 described herein. The ability of an antibody or antigen-binding fragment to competitively bind to IL-36R can be measured using competitive binding assays known in the art.

The humanized anti-IL-36R antibodies optionally include specific amino acid substitutions in the consensus or germline framework regions. The specific substitution of amino acid residues in these framework positions can improve various aspects of antibody performance including binding affinity and/or stability, over that demonstrated in humanized antibodies formed by "direct swap" of CDRs or HVLs into the human germline framework regions.

In some embodiments, the present invention describes other monoclonal antibodies with a light chain variable region having the amino acid sequence set forth in any one of SEQ ID NO:1-10. In some embodiments, the present invention describes other monoclonal antibodies with a heavy chain variable region having the amino acid sequence set forth in any one of SEQ ID NO:11-20. Placing such CDRs into FRs of the human consensus heavy and light chain variable domains will yield useful humanized antibodies of the present invention.

In particular, the present invention provides monoclonal antibodies with the combinations of light chain variable and heavy chain variable regions of SEQ ID NO:1/11, 2/12, 3/13, 4/14, 5/15, 6/16, 7/17, 8/18, 9/19, 10/20. Such variable regions can be combined with human constant regions.

In some embodiments, the present invention describes other humanized antibodies with light chain variable region sequences having the amino acid sequence set forth in any one of SEQ ID NO:76-86. In some embodiments, the present invention describes other humanized antibodies with heavy chain variable region sequences having the amino acid sequence set forth in any one of SEQ ID NO:87-101. In particular, the present invention provides monoclonal antibodies with the combinations of light chain variable and heavy chain variable regions of SEQ ID NO: 77/89, 80/88, 80/89, 77/87, 77/88, 80/87, 86/100, 85/101, 85/100. Such variable regions can be combined with human constant regions.

In a further embodiment, the present invention relates to an anti-IL-36R antibody or antigen-binding fragment thereof comprising a humanized light chain variable domain comprising the CDRs of SEQ ID NO:77 and framework regions having an amino acid sequence at least 90% identical, at least 93% identical or at least 95% identical to the amino acid sequence of the framework regions of the variable domain light chain amino acid sequence of SEQ ID NO:77 and a humanized heavy chain variable domain comprising the CDRs of SEQ ID NO:89 and framework regions having an amino acid sequence at least 90% identical, at least 93% identical or at least 95% identical to the amino acid sequence of the framework regions of the variable domain heavy chain amino acid sequence of SEQ ID NO:89. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:80 and framework regions having an amino acid sequence at least 90% identical, at least 93% identical or at least 95% identical to the amino acid sequence of the framework regions of the variable domain light chain amino acid sequence of SEQ ID NO:80 and a humanized heavy chain variable domain comprising the CDRs of SEQ ID NO:88 and framework regions having an amino acid sequence at least 90% identical, at least 93% identical or at least 95% identical to the amino acid sequence of the framework regions of the variable domain heavy chain amino acid sequence of SEQ ID NO:88. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:80 and framework regions having an amino acid sequence at least 90% identical, at least 93% identical or at least 95% identical to the amino acid sequence of the framework regions of the variable domain light chain amino acid sequence of SEQ ID NO:80 and a humanized heavy chain variable domain comprising the CDRs of SEQ ID NO:89 and framework regions having an amino acid sequence at least 90% identical, at least 93% identical or at least 95% identical to the amino acid sequence of the framework regions of the variable domain heavy chain amino acid sequence of SEQ ID NO:89. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:77 and framework regions having an amino acid sequence at least 90% identical, at least 93% identical or at least 95% identical to the amino acid sequence of the framework regions of the variable domain light chain amino acid sequence of SEQ ID NO:77 and a humanized heavy chain variable domain comprising the CDRs of SEQ ID NO:87 and framework regions having an amino acid sequence at least 90% identical, at least 93% identical or at least 95% identical to the amino acid sequence of the framework regions of the variable domain heavy chain amino acid sequence of SEQ ID NO:87. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:77 and framework regions having an amino acid sequence at least 90% identical, at least 93% identical or at least 95% identical to the amino acid sequence of the framework regions of the variable domain light chain amino acid sequence of SEQ ID NO:77 and a humanized heavy chain variable domain comprising the CDRs of SEQ ID NO:88 and framework regions having an amino acid sequence at least 90% identical, at least 93% identical or at least 95% identical to the amino acid sequence of the framework regions of the variable domain heavy chain amino acid sequence of SEQ ID NO:88. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:80 and framework regions having an amino acid sequence at least 90% identical, at least 93% identical or at least 95% identical to the amino acid sequence of the framework regions of the variable domain light chain amino acid sequence of SEQ ID NO:80 and a humanized heavy chain variable domain comprising the CDRs of SEQ ID NO:87 and framework regions having an amino acid sequence at least 90% identical, at least 93% identical or at least 95% identical to the amino acid sequence of the framework regions of the variable domain heavy chain amino acid sequence of SEQ ID NO:87. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:86 and framework regions having an amino acid sequence at least 90% identical, at least 93% identical or at least 95% identical to the amino acid sequence of the framework regions of the variable domain light chain amino acid sequence of SEQ ID NO:86 and a humanized heavy chain variable domain comprising the CDRs of SEQ ID NO:100 and framework regions having an amino acid sequence at least 90% identical, at least 93% identical or at least 95% identical to the amino acid sequence of the framework regions of the variable domain heavy chain amino acid sequence of SEQ ID NO:100. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:85 and framework regions having an amino acid sequence at least 90% identical, at least 93% identical or at least 95% identical to the amino acid sequence of the framework regions of the variable domain light chain amino acid sequence of SEQ ID NO:85 and a humanized heavy chain variable domain comprising the CDRs of SEQ ID NO:101 and framework regions having an amino acid sequence at least 90% identical, at least 93% identical or at least 95% identical to the amino acid sequence of the framework regions of the variable domain heavy chain amino acid sequence of SEQ ID NO:101. In one embodiment, the anti-IL-36R antibody is a humanized monoclonal antibody.

In a further embodiment, the present invention relates to an anti-IL-36R antibody or antigen-binding fragment thereof comprising a humanized light chain variable domain comprising the CDRs of SEQ ID NO:85 and framework regions having an amino acid sequence at least 90% identical, at least 93% identical or at least 95% identical to the amino acid sequence of the framework regions of the variable domain light chain amino acid sequence of SEQ ID NO:85 and a humanized heavy chain variable domain comprising the CDRs of SEQ ID NO:100 and framework regions having an amino acid sequence at least 90% identical, at least 93% identical or at least 95% identical to the amino acid sequence of the framework regions of the variable domain heavy chain amino acid sequence of SEQ ID NO:100. In one embodiment, the anti-IL-36R antibody is a humanized monoclonal antibody.

In some specific embodiments, the humanized anti-IL-36R antibodies disclosed herein comprise at least a heavy or a light chain variable domain comprising the CDRs or HVLs of the murine monoclonal antibodies or humanized antibodies as disclosed herein and the FRs of the human germline heavy and light chain variable domains.

In one further aspect, the present invention provides an anti-IL-36R antibody or antigen-binding fragment thereof comprising a light chain CDR1 (L-CDR1) sequence of any one of SEQ ID NO:21-29; a light chain CDR2 (L-CDR2) sequence of any one of SEQ ID NO:30-38; a light chain CDR3 (L-CDR3) sequence of any one of SEQ ID NO:39-

47; a heavy chain CDR1 (H-CDR1) sequence of any one of SEQ ID NO:48-56; a heavy chain CDR2 (H-CDR2) sequence of any one of SEQ ID NO:57-66; and a heavy chain CDR3 (H-CDR3) sequence of any one of SEQ ID NO:67-75. In one aspect, the anti-IL-36R antibody or antigen-binding fragment thereof comprises a light chain variable region comprising a L-CDR1 listed above, a L-CDR2 listed above and a L-CDR3 listed above, and a heavy chain variable region comprising a H-CDR1 listed above, a H-CDR2 listed above and a H-CDR3 listed above.

In a further aspect, the present invention provides an anti-IL-36R antibody or antigen-binding fragment thereof comprising:
a) a L-CDR1, a L-CDR2, a L-CDR3, a H-CDR1, a H-CDR2 and a H-CDR3 sequence of SEQ ID NO:21, 30, 39, 48, 57 and 67, respectively; or
b) a L-CDR1, a L-CDR2, a L-CDR3, a H-CDR1, a H-CDR2 and a H-CDR3 sequence of SEQ ID NO:22, 31, 40, 49, 58 and 68, respectively; or
c) a L-CDR1, a L-CDR2, a L-CDR3, a H-CDR1, a H-CDR2 and a H-CDR3 sequence of SEQ ID NO:23, 32, 41, 50, 59 and 69, respectively; or
d) a L-CDR1, a L-CDR2, a L-CDR3, a H-CDR1, a H-CDR2 and a H-CDR3 sequence of SEQ ID NO:24, 33, 42, 51, 60 and 70, respectively; or
e) a L-CDR1, a L-CDR2, a L-CDR3, a H-CDR1, a H-CDR2 and a H-CDR3 sequence of SEQ ID NO:25, 34, 43, 52, 61 and 71, respectively; or
f) a L-CDR1, a L-CDR2, a L-CDR3, a H-CDR1, a H-CDR2 and a H-CDR3 sequence of SEQ ID NO:26, 35, 44, 53, 62 and 72, respectively; or
g) a L-CDR1, a L-CDR2, a L-CDR3, a H-CDR1, a H-CDR2 and a H-CDR3 sequence of SEQ ID NO:27, 36, 45, 54, 63 and 73, respectively; or
h) a L-CDR1, a L-CDR2, a L-CDR3, a H-CDR1, a H-CDR2 and a H-CDR3 sequence of SEQ ID NO:27, 36, 45, 54, 64 and 74, respectively; or
i) a L-CDR1, a L-CDR2, a L-CDR3, a H-CDR1, a H-CDR2 and a H-CDR3 sequence of SEQ ID NO:27, 36, 45, 54, 64 and 73, respectively; or
j) a L-CDR1, a L-CDR2, a L-CDR3, a H-CDR1, a H-CDR2 and a H-CDR3 sequence of SEQ ID NO:28, 37, 46, 55, 65 and 74, respectively; or
k) a L-CDR1, a L-CDR2, a L-CDR3, a H-CDR1, a H-CDR2 and a H-CDR3 sequence of SEQ ID NO:29, 38, 47, 56, 66 and 75, respectively.

In a further aspect, the present invention provides an anti-IL-36R antibody or antigen-binding fragment thereof comprising:
a) a L-CDR1, a L-CDR2, a L-CDR3, a H-CDR1, a H-CDR2 and a H-CDR3 sequence of SEQ ID NO:26, 103, 44, 53, 62 and 72, respectively; or
b) a L-CDR1, a L-CDR2, a L-CDR3, a H-CDR1, a H-CDR2 and a H-CDR3 sequence of SEQ ID NO:26, 104, 44, 53, 62 and 72, respectively; or
c) a L-CDR1, a L-CDR2, a L-CDR3, a H-CDR1, a H-CDR2 and a H-CDR3 sequence of SEQ ID NO:27, 36, 45, 107, 63 and 73, respectively; or
d) a L-CDR1, a L-CDR2, a L-CDR3, a H-CDR1, a H-CDR2 and a H-CDR3 sequence of SEQ ID NO:27, 36, 45, 107, 64 or 73, respectively.

In one aspect, the anti-IL-36R antibody or antigen-binding fragment thereof comprises a light chain variable region comprising a L-CDR1, L-CDR2 and L-CDR3 combination listed above, and a heavy chain variable region comprising a H-CDR1, H-CDR2 and H-CDR3 combination listed above.

In specific embodiments, it is contemplated that chimeric antibodies with switched CDR regions (i.e., for example switching one or two CDRs of one of the mouse antibodies or humanized antibody derived therefrom with the analogous CDR from another mouse antibody or humanized antibody derived therefrom) between these exemplary immunoglobulins may yield useful antibodies.

In certain embodiments, the humanized anti-IL-36R antibody is an antibody fragment. Various antibody fragments have been generally discussed above and there are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from E. coli and chemically coupled to form $F(ab')_2$ fragments (see, e.g., Carter et al., 1992, Bio/Technology 10:163-167). By another approach, $F(ab')_2$ fragments can be isolated directly from recombinant host cell culture. Other techniques for the production of antibody fragments will be apparent to the skilled practitioner. Accordingly, in one aspect, the present invention provides antibody fragments comprising the CDRs described herein, in particular one of the combinations of L-CDR1, L-CDR2, L-CDR3, H-CDR1, H-CDR2 and H-CDR3 described herein. In a further aspect, the present invention provides antibody fragments comprising the variable regions described herein, for example one of the combinations of light chain variable regions and heavy chain variable regions described herein.

Certain embodiments include an $F(ab')_2$ fragment of a humanized anti-IL-36R antibody comprise a light chain sequence of any of SEQ ID NO: 115 or 118 in combination with a heavy chain sequence of SEQ ID NO: 125, 126 or 127. Such embodiments can include an intact antibody comprising such an $F(ab')_2$.

Certain embodiments include an $F(ab')_2$ fragment of a humanized anti-IL-36R antibody comprise a light chain sequence of any of SEQ ID NO: 123 or 124 in combination with a heavy chain sequence of SEQ ID NO: 138 or 139. Such embodiments can include an intact antibody comprising such an $F(ab')_2$.

In some embodiments, the antibody or antibody fragment includes a constant region that mediates effector function. The constant region can provide antibody-dependent cellular cytotoxicity (ADCC), antibody-dependent cellular phagocytosis (ADCP) and/or complement-dependent cytotoxicity (CDC) responses against an IL-36R expressing target cell. The effector domain(s) can be, for example, an Fc region of an Ig molecule.

The effector domain of an antibody can be from any suitable vertebrate animal species and isotypes. The isotypes from different animal species differ in the abilities to mediate effector functions. For example, the ability of human immunoglobulin to mediate CDC and ADCC/ADCP is generally in the order of $IgM \approx IgG_1 \approx IgG_3 > IgG_2 > IgG_4$ and $IgG_1 \approx IgG_3 > IgG_2 / IgM / IgG_4$, respectively. Murine immunoglobulins mediate CDC and ADCC/ADCP generally in the order of murine $IgM \approx IgG_3 >> IgG_{2b} > IgG_{2a} >> IgG_1$ and $IgG_{2b} > IgG_{2a} > IgG_1 >> IgG_3$, respectively. In another example, murine $IgG_{2a}$ mediates ADCC while both murine $IgG_{2a}$ and IgM mediate CDC.

Humanization and Amino Acid Sequence Variants

Amino acid sequence variants of the anti-IL-36R antibody can be prepared by introducing appropriate nucleotide changes into the anti-IL-36R antibody DNA, or by peptide synthesis. Such variants include, for example, deletions from, and/or insertions into and/or substitutions of, residues within the amino acid sequences of the anti-IL-36R antibodies of the examples herein. Any combination of deletions, insertions, and substitutions is made to arrive at the final construct, provided that the final construct possesses the desired characteristics. The amino acid changes also may alter post-translational processes of the humanized or variant anti-IL-36R antibody, such as changing the number or position of glycosylation sites.

A useful method for identification of certain residues or regions of the anti-IL-36R antibody that are preferred locations for mutagenesis is called "alanine scanning mutagenesis," as described by Cunningham and Wells (Science, 244:1081-1085 (1989)). Here, a residue or group of target residues are identified (e.g., charged residues such as arg, asp, his, lys, and glu) and replaced by a neutral or negatively charged amino acid (typically alanine) to affect the interaction of the amino acids with IL-36R antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed anti-IL-36R antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-IL-36R antibody fused to an epitope tag. Other insertional variants of the anti-IL-36R antibody molecule include a fusion to the N- or C-terminus of the anti-IL-36R antibody of an enzyme or a polypeptide which increases the serum half-life of the antibody.

Another type of variant is an amino acid substitution variant. These variants have at least one amino acid residue in the anti-IL-36R antibody molecule removed and a different residue inserted in its place. The sites of greatest interest for substitutional mutagenesis include the hypervariable regions, but FR alterations are also contemplated. Conservative substitutions are shown in Table C under the heading of "preferred substitutions". If such substitutions result in a change in biological activity, then more substantial changes, denominated "exemplary substitutions", or as further described below in reference to amino acid classes, may be introduced and the products screened.

TABLE C

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | arg; asn; gln; lys; | arg |
| Ile (I) | leu; val; met; ala; phe; norleucine | leu |
| Leu (L) | ile; norleucine; val; met; ala; phe | ile |

TABLE C-continued

| Original Residue | Exemplary Substitutions | Preferred Substitutions |
|---|---|---|
| Lys (K) | arg; gln; asn | arg |
| Met (M) | leu; phe; ile | leu |
| Phe (F) | tyr; leu; val; ile; ala; | tyr |
| Pro (P) | ala | ala |
| Ser (S) | thr | thr |
| Thr (T) | ser | ser |
| Trp (W) | tyr; phe | tyr |
| Tyr (Y) | phe; trp; thr; ser | phe |
| Val (V) | leu; ile; met; phe ala; norleucine; | leu |

In protein chemistry, it is generally accepted that the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.
Non-conservative substitutions will entail exchanging a member of one of these classes for another class.

Any cysteine residue not involved in maintaining the proper conformation of the humanized or variant anti-IL-36R antibody also may be substituted, generally with serine, to improve the oxidative stability of the molecule, prevent aberrant crosslinking, or provide for established points of conjugation to a cytotoxic or cytostatic compound. Conversely, cysteine bond(s) may be added to the antibody to improve its stability (particularly where the antibody is an antibody fragment such as an Fv fragment).

A type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants is affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity). In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and human IL-36R. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By "altering" is meant deleting one or more carbohydrate moieties found in the antibody, and/or adding one or more glycosylation sites that are not present in the antibody.

In some embodiments, it may be desirable to modify the antibodies of the invention to add glycosylations sites. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Thus, in order to glycosylate a given protein, e.g., an antibody, the amino acid sequence of the protein is engineered to contain one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IL-36R antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-IL-36R antibody.

Polynucleotides, Vectors, Host Cells, and Recombinant Methods

Other embodiments encompass isolated polynucleotides that comprise a sequence encoding a humanized anti-IL-36R antibody, vectors, and host cells comprising the polynucleotides, and recombinant techniques for production of the humanized antibody. The isolated polynucleotides can encode any desired form of the anti-IL-36R antibody including, for example, full length monoclonal antibodies, Fab, Fab', F(ab')$_2$, and Fv fragments, diabodies, linear antibodies, single-chain antibody molecules, and multispecific antibodies formed from antibody fragments.

Some embodiments include isolated polynucleotides comprising sequences that encode the light chain variable region of an antibody or antibody fragment having the amino acid sequence of any of SEQ ID NO: SEQ ID NO:1-10. Some embodiments include isolated polynucleotides comprising sequences that encode the heavy chain variable region of an antibody or antibody fragment having the amino acid sequence of SEQ ID NO:11-20.

Some embodiments include isolated polynucleotides comprising sequences that encode the light chain variable region of an antibody or antibody fragment having the amino acid sequence of any of SEQ ID NO:76-86. Some embodiments include isolated polynucleotides comprising sequences that encode the heavy chain variable region of an antibody or antibody fragment having the amino acid sequence of SEQ ID NO: 87-101.

Some embodiments include isolated polynucleotides comprising sequences that encode the light chain of an antibody having the amino acid sequence of any of SEQ ID NO:114-124. Some embodiments include isolated polynucleotides comprising sequences that encode the heavy chain of an antibody having the amino acid sequence of SEQ ID NO:125-139.

In one aspect, the isolated polynucleotide sequence(s) encodes an antibody or antibody fragment having a light chain and a heavy chain variable region comprising the amino acid sequences of SEQ ID NO:115 and SEQ ID NO:127, respectively; SEQ ID NO:118 and SEQ ID NO:126, respectively; SEQ ID NO:118 and SEQ ID NO:127, respectively; SEQ ID NO:115 and SEQ ID NO:125, respectively; SEQ ID NO:115 and SEQ ID NO:126, respectively; SEQ ID NO:118 and SEQ ID NO:125, respectively; SEQ ID NO:124 and SEQ ID NO:138, respectively; SEQ ID NO:123 and SEQ ID NO:139, respectively; SEQ ID NO:123 and SEQ ID NO:138, respectively.

The polynucleotide(s) that comprise a sequence encoding a humanized anti-IL-36R antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The humanized anti-IL-36R antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the humanized anti-IL-36R antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* a-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the humanized anti-IL-36R antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-u. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin. Common selectable markers for mammalian cells are those that enable the identification of cells competent to take up a nucleic acid encoding a humanized anti-IL-36R antibody, such as DHFR (dihydrofolate reductase), thymidine kinase, metallothionein-I and -II (such as primate metallothionein genes), adenosine deaminase, ornithine decarboxylase, and the like. Cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-IL-36R antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

Where the recombinant production is performed in a yeast cell as a host cell, the TRP1 gene present in the yeast plasmid YRp7 (Stinchcomb et al., 1979, Nature 282: 39) can be used as a selectable marker. The TRP1 gene provides a selection marker for a mutant strain of yeast lacking the ability to grow in tryptophan, for example, ATCC No. 44076 or PEP4-1 (Jones, 1977, Genetics 85:12). The presence of the trp1 lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* (Van den Berg, 1990, Bio/Technology 8:135). Stable multi-copy expression vectors for secretion of mature recombinant human serum albumin by industrial strains of *Kluyveromyces* have also been disclosed (Fleer et al., 1991, Bio/Technology 9:968-975).

Expression and cloning vectors usually contain a promoter that is recognized by the host organism and is operably linked to the nucleic acid molecule encoding an anti-IL-36R antibody or polypeptide chain thereof. Promoters suitable for use with prokaryotic hosts include phoA promoter, P3-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-IL-36R antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Humanized anti-IL-36R antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human p-interferon cDNA in mouse cells under the control of a thymidine kinase promoter from herpes simplex virus. Alternatively, the Rous sarcoma virus long terminal repeat can be used as the promoter.

Another useful element that can be used in a recombinant expression vector is an enhancer sequence, which is used to increase the transcription of a DNA encoding a humanized anti-IL-36R antibody by higher eukaryotes. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the humanized anti-IL-36R antibody-encoding sequence, but is preferably located at a site 5' from the promoter.

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-IL-36R antibody. One useful transcription termination component is the bovine growth hormone polyadenylation region. See WO94/11026 and the expression vector disclosed therein. In some embodiments, humanized anti-IL-36R antibodies can be expressed using the CHEF system. (See, e.g., U.S. Pat. No. 5,888,809; the disclosure of which is incorporated by reference herein.)

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis (e.g., B. licheniformis 41 P disclosed in DD 266,710 published Apr. 12, 1989), Pseudomonas such as P. aeruginosa, and Streptomyces. One preferred E. coli cloning host is E. coli 294 (ATCC 31,446), although other strains such as E. coli B, E. coli X1776 (ATCC 31,537), and E. coli W3110 (ATCC 27,325) are suitable. These examples are illustrative rather than limiting.

In addition to prokaryotes, eukaryotic microbes such as filamentous fungi or yeast are suitable cloning or expression hosts for humanized anti-IL-36Rantibody-encoding vectors. Saccharomyces cerevisiae, or common baker's yeast, is the most commonly used among lower eukaryotic host microorganisms. However, a number of other genera, species, and strains are commonly available and useful herein, such as Schizosaccharomyces pombe; Kluyveromyces hosts such as, e.g., K. lactis, K. fragilis (ATCC 12,424), K. bulgaricus (ATCC 16,045), K. wickeramii (ATCC 24,178), K. waltii (ATCC 56,500), K. drosophilarum (ATCC 36,906), K. thermotolerans, and K. marxianus; yarrowia (EP 402,226); Pichia pastors (EP 183,070); Candida; Trichoderma reesia (EP 244,234); Neurospora crassa; Schwanniomyces such as Schwanniomyces occidentalis; and filamentous fungi such as, e.g., Neurospora, Penicillium, Tolypocladium, and Aspergillus hosts such as A. nidulans and A. niger.

Suitable host cells for the expression of glycosylated humanized anti-IL-36R antibody are derived from multicellular organisms. Examples of invertebrate cells include plant and insect cells, including, e.g., numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori (silk worm). A variety of viral strains for transfection are publicly available, e.g., the L-1 variant of Autographa californica NPV and the Bm-5 strain of Bombyx mori NPV, and such viruses may be used, particularly for transfection of Spodoptera frugiperda cells.

Plant cell cultures of cotton, corn, potato, soybean, petunia, tomato, and tobacco can also be utilized as hosts.

In another aspect, expression of humanized anti-IL-36R is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/-DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Host cells are transformed with the above-described expression or cloning vectors for humanized anti-IL-36R antibody production and cultured in conventional nutrient media modified as appropriate for inducing promoters, selecting transformants, or amplifying the genes encoding the desired sequences.

The host cells used to produce a humanized anti-IL-36R antibody described herein may be cultured in a variety of media. Commercially available media such as Ham's F10 (Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, Meth. Enz. 58: 44, Barnes et al., 1980, Anal. Biochem. 102: 255, U.S. Pat. Nos. 4,767,704, 4,657,866, 4,927,762, 4,560,655, 5,122, 469, WO 90/103430, and WO 87/00195 may be used as culture media for the host cells.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an antibody or antibody fragment of the present invention. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-IL-36R polypeptide (e.g., a heavy chain or light chain variable region), or its complement. Hybridizing nucleic acids of the type described herein can be used, for example, as a cloning probe, a primer, e.g., a PCR primer, or a diagnostic probe.

Therapeutic Uses

In another embodiment, a humanized anti-IL-36R antibody disclosed herein is useful in the treatment of various disorders associated with the expression of IL-36R as described herein. Methods for treating an IL-36R associated disorder comprise administering a therapeutically effective amount of a humanized anti-IL-36R antibody to a subject in need thereof.

The humanized anti-IL-36R antibody or agent is administered by any suitable means, including parenteral, subcutaneous, intrapulmonary, and intranasal, and, if desired for local immunosuppressive treatment, intralesional administration (including perfusing or otherwise contacting the graft with the antibody before transplantation). The humanized anti-IL-36R antibody or agent can be administered, for example, as an infusion or as a bolus. Parenteral infusions include intramuscular, intravenous, intraarterial, or subcutaneous administration. In addition, the humanized anti-IL-36R antibody is suitably administered by pulse infusion, particularly with declining doses of the antibody. In one aspect, the dosing is given by injections, most preferably intravenous or subcutaneous injections, depending in part on whether the administration is brief or chronic.

For the prevention or treatment of disease, the appropriate dosage of antibody will depend on a variety of factors such as the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 20 mg/kg (e.g., 0.1-15 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is that disclosed in WO 94/04188.

The term "suppression" is used herein in the same context as "amelioration" and "alleviation" to mean a lessening of one or more characteristics of the disease.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat the disorder associated with IL-36R expression.

The antibody need not be, but is optionally, formulated with one or more agents currently used to prevent or treat the disorder in question. The effective amount of such other agents depends on the amount of humanized anti-IL-36R23p19 antibody present in the formulation, the type of disorder or treatment, and other factors discussed above. These are generally used in the same dosages and with administration routes as used hereinbefore or about from 1 to 99% of the heretofore employed dosages.

Treatment with the Antibody Formulation

In one embodiment, the invention provides a method of treating a disease or disorder in a subject comprising administering the formulation described herein to a subject in an amount effective to treat the disease or disorder.

The antibody formulations of the present invention are useful in methods for the treatment of various diseases or disorders, for example immunological, inflammatory, autoimmune diseases and respiratory diseases in humans. For example, the antibody formulations of the present invention are useful in methods for the treatment of psoriasis, rheumatoid arthritis, inflammatory bowel disease or psoriatic arthritis. For example, the antibody formulations of the present invention are useful in methods for the treatment of chronic obstructive pulmonary disorder (COPD) or asthma. For example, the antibody formulations of the present invention are useful in methods for the treatment of scleroderma, palmoplantar pustulosis, generalized pustular psoriasis, diabetic nephropathy, lupus nephritis, scleroderma, ankylosing spondylitis, deficiency in the IL-36 receptor antagonist autoimmune disease (DITRA), deficiency in the IL-1 receptor antagonist autoimmune disease (DIRA) or cryopyrin associated periodic syndromes (CAPS).

A formulation comprising an IL-36R binding agent (e.g., an anti-IL-36R antibody) can be administered to a subject having or at risk of having an immunological disorder, respiratory disorder or a cancer. The invention further provides for the use of a IL-36R binding agent (e.g., an anti-IL-36R antibody) in the manufacture of a medicament for prevention or treatment of a cancer, respiratory disorder or immunological disorder. The term "subject" as used herein means any mammalian patient to which an IL-36Rbinding agent can be administered, including, e.g., humans and non-human mammals, such as primates, rodents, and dogs. Subjects specifically intended for treatment using the methods described herein include humans. The antibodies or agents can be administered either alone or in combination with other compositions in the prevention or treatment of the immunological disorder, respiratory disorder or cancer. Such compositions which can be administered in combination with the antibodies or agents include methotrexate (MTX) and immunomodulators, e.g. antibodies or small molecules.

In one aspect, the present invention relates to a method of treating a disease or condition (such as those listed above) in a subject, the method includes administering to the subject a therapeutic amount of a stable pharmaceutical formulation comprising from about 20 mg/mL to about 150 mg/mL of an anti-IL-36R antibody, about 20 mM to about 80 mM of a pharmaceutically acceptable buffer (e.g., acetate buffer), about 100 mM to about 250 mM of a pharmaceutically acceptable tonicifying agent (e.g., sucrose), about 0 mM to about 80 mM of a pharmaceutically acceptable stabilizing agent (e.g., arginine) or a pharmaceutically acceptable salt thereof, about 0 to about 150 mM of a pharmaceutically acceptable salt (e.g., sodium chloride), and a pharmaceutically acceptable surfactant (e.g., polysorbate 20) in an amount about 0.1 g/L to about 1.5 g/L, wherein the disease or condition is treated. In a related embodiment, the stable pharmaceutical formulation is an aqueous pharmaceutical formulation. In a related embodiment, the pH of the aqueous pharmaceutical formulation is about 5 to about 7. In a related embodiment, the pharmaceutical formulation is for an intravenous administration to the subject. In a related embodiment, the pharmaceutical formulation is for a subcutaneous administration to the subject. In a related embodiment, the pharmaceutical formulation for the intravenous administration comprises an anti-IL-36R antibody in an amount of about 60 mg/mL. In a related embodiment, the pharmaceutical formulation for a subcutaneous administration comprises an anti-IL-36R antibody in an amount of about 150 mg/mL. In a related embodiment, the anti-IL-36R antibody comprising: (i) a light chain comprising an amino acid sequence set forth as SEQ ID NO:118 and a heavy chain comprising an amino acid sequence set forth as SEQ ID NO:125; or (ii) a light chain comprising an amino acid sequence set forth as SEQ ID NO:118 and a heavy chain comprising an amino acid sequence set forth as SEQ ID NO:126; or (iii) a light chain comprising an amino acid sequence set forth as SEQ ID NO:118 and a heavy chain comprising an amino acid sequence set forth as SEQ ID NO:127. In a related embodiment, the anti-IL-36R antibody comprising: a light chain variable region comprising the amino acid sequence of SEQ ID NO: 77; and a heavy chain variable region comprising the amino acid sequence of SEQ ID NO: 87; or a light chain variable region comprising the amino acid sequence of SEQ ID NO: 77; and a heavy chain variable region comprising the amino acid sequence of SEQ ID NO: 88; or a light chain variable region comprising the amino acid sequence of SEQ ID NO: 77; and a heavy chain variable region comprising the amino acid sequence of SEQ ID NO: 89; or a light chain variable region comprising the amino acid sequence of SEQ ID NO: 80; and a heavy chain variable region comprising the amino acid sequence of SEQ ID NO: 87; or a light chain variable region comprising the amino acid sequence of SEQ ID NO: 80; and a heavy chain variable region comprising the amino acid sequence of SEQ ID NO: 88; or a light chain variable region comprising the amino acid sequence of SEQ ID NO: 80; and a heavy chain variable region comprising the amino acid sequence of SEQ ID NO: 89.

In one embodiment, the method of treatment according to any of the preceding aspects, comprises administering to the subject a therapeutic amount of a stable pharmaceutical formulation selected from the group consisting of consisting of:

I. formulation comprising about 20 mg/mL to about 150 mg/mL of the anti-IL-36R antibody, about 40 mM histidine, about 120 mM sucrose, about 50 mM L-Arginine, about 5 mM NaCl and about 1.0 g/L Polysorbate 20, with a pH of about 6.0;

II. formulation comprising about 20 mg/mL to about 150 mg/mL of the anti-IL-36R antibody, about 45 mM acetate, about 150 mM sucrose, about 25 mM L-Arginine, about 0.4 g/L Polysorbate 20, with a pH of about 5.5;

III. formulation comprising about 20 mg/mL to about 150 mg/mL of the anti-IL-36R antibody, about 45 mM acetate, about 180 mM sucrose, about 25 mM Glycine, about 0.4 g/L Polysorbate 80, with a pH of about 5.5;

IV. formulation comprising about 20 mg/mL to about 150 mg/mL of the anti-IL-36R antibody, about 25 mM citrate, about 150 mM trehalose, about 25 mM methionine, about 0.2 g/L Polysorbate 20, with a pH of about 6.0;

V. formulation comprising about 20 mg/mL to about 150 mg/mL of the anti-IL-36R antibody, about 25 mM histidine, about 160 mM sucrose, about 20 mM mannitol, about 0.2 g/L Polysorbate 20, with a pH of about 6.0;

VI. formulation comprising about 20 mg/mL to about 150 mg/mL of the anti-IL-36R antibody, about 25 mM citrate, about 200 mM sucrose, about 0.4 g/L Polysorbate 80, with a pH of about 6.5;

VII. formulation comprising about 20 mg/mL to about 150 mg/mL of the anti-IL-36R antibody, about 45 mM acetate, about 150 mM sucrose, about 25 mM L-Arginine, about 0.4 g/L Polysorbate 20, with a pH of about 5.5;

VIII. formulation comprising about 20 mg/mL to about 150 mg/mL of the anti-IL-36R antibody, about 35 mM histidine, about 180 mM trehalose, about 25 mM L-Arginine, about 3 mM NaCl, about 0.4 g/L Polysorbate 80, with a pH of about 6.0;

IX. formulation comprising about 20 mg/mL to about 150 mg/mL of the anti-IL-36R antibody, about 25 mM acetate, about 100 mM mannitol, about 50 mM NaCl, about 0.2 g/L Polysorbate 20, with a pH of about 5.5; and X. formulation comprising about 20 mg/mL to about 150 mg/mL of the anti-IL-36R antibody, about 20 mM succinate, about 220 mM sucrose, about 0.1 g/L Polysorbate 80, with a pH of about 6.0, wherein the disease or condition is treated. In a related embodiment, the stable pharmaceutical formulation is an aqueous pharmaceutical formulation. In a related embodiment, the pharmaceutical formulation is for an intravenous administration to the subject. In a related embodiment, the pharmaceutical formulation is for a subcutaneous administration to the subject. In a related embodiment, the pharmaceutical formulation for an intravenous administration comprises an anti-IL-36R antibody in an amount of about 60 mg/mL. In a related embodiment, the pharmaceutical formulation for a subcutaneous administration comprises an anti-IL-36R antibody in an amount of about 150 mg/mL. In a related embodiment, the anti-IL-36R antibody comprising: (i) a light chain comprising an amino acid sequence set forth as SEQ ID NO:118 and a heavy chain comprising an amino acid sequence set forth as SEQ ID NO:125; or (ii) a light chain comprising an amino acid sequence set forth as SEQ ID NO:118 and a heavy chain comprising an amino acid sequence set forth as SEQ ID NO:126; or (iii) a light chain comprising an amino acid sequence set forth as SEQ ID NO:118 and a heavy chain comprising an amino acid sequence set forth as SEQ ID NO:127. In a related embodiment, the anti-IL-36R antibody comprising: a light chain variable region comprising the amino acid sequence of SEQ ID NO: 77; and a heavy chain variable region comprising the amino acid sequence of SEQ ID NO: 87; or a light chain variable region comprising the amino acid sequence of SEQ ID NO: 77; and a heavy chain variable region comprising the amino acid sequence of SEQ ID NO: 88; or a light chain variable region comprising the amino acid sequence of SEQ ID NO: 77; and a heavy chain variable region comprising the amino acid sequence of SEQ ID NO: 89; or a light chain variable region comprising the amino acid sequence of SEQ ID NO: 80; and a heavy chain variable region comprising the amino acid sequence of SEQ ID NO: 87; or a light chain variable region comprising the amino acid sequence of SEQ ID NO: 80; and a heavy chain variable region comprising the amino acid sequence of SEQ ID NO: 88; or a light chain variable region comprising the amino acid sequence of SEQ ID NO: 80; and a heavy chain variable region comprising the amino acid sequence of SEQ ID NO: 89.

In one embodiment, the method of treatment according to any of the preceding aspects, comprises administering to the subject a therapeutic amount of a stable pharmaceutical formulation selected from the group consisting of consisting of:

I. formulation comprising about 20 mg/mL of the anti-IL-36R antibody, about 40 mM histidine, about 120 mM sucrose, about 50 mM L-Arginine, about 5 mM NaCl and about 1.0 g/L Polysorbate 20, with a pH of about 6.0;

II. formulation comprising about 60 mg/mL of the anti-IL-36R antibody, about 45 mM acetate, about 150 mM sucrose, about 25 mM L-Arginine, about 0.4 g/L Polysorbate 20, with a pH of about 5.5;

III. formulation comprising about 20 mg/mL of the anti-IL-36R antibody, about 45 mM acetate, about 180 mM sucrose, about 25 mM Glycine, about 0.4 g/L Polysorbate 80, with a pH of about 5.5;

IV. formulation comprising about 150 mg/mL of the anti-IL-36R antibody, about 25 mM citrate, about 150 mM trehalose, about 25 mM methionine, about 0.2 g/L Polysorbate 20, with a pH of about 6.0;

V. formulation comprising about 60 mg/mL of the anti-IL-36R antibody, about 25 mM histidine, about 160 mM sucrose, about 20 mM mannitol, about 0.2 g/L Polysorbate 20, with a pH of about 6.0;

VI. formulation comprising about 20 mg/mL of the anti-IL-36R antibody, about 25 mM citrate, about 200 mM sucrose, about 0.4 g/L Polysorbate 80, with a pH of about 6.5;

VII. formulation comprising about 150 mg/mL of the anti-IL-36R antibody, about 45 mM acetate, about 150 mM sucrose, about 25 mM L-Arginine, about 0.4 g/L Polysorbate 20, with a pH of about 5.5;

VIII. formulation comprising about 15 mg/mL of the anti-IL-36R antibody, about 35 mM histidine, about 180 mM trehalose, about 25 mM L-Arginine, about 3 mM NaCl, about 0.4 g/L Polysorbate 80, with a pH of about 6.0;

IX. formulation comprising about 80 mg/mL of the anti-IL-36R antibody, about 25 mM acetate, about 100 mM mannitol, about 50 mM NaCl, about 0.2 g/L Polysorbate 20, with a pH of about 5.5; and X. formulation comprising about 100 mg/mL of the anti-IL-36R antibody, about 20 mM succinate, about 220 mM sucrose, about 0.1 g/L Polysorbate 80, with a pH of about 6.0, wherein the disease or condition is treated. In a related embodiment, the stable pharmaceutical formulation is an aqueous pharmaceutical formulation. In a related embodiment, the pharmaceutical formulation is for an intravenous administration to the subject. In a related embodiment, the pharmaceutical formulation is for a subcutaneous administration to the subject. In a related embodiment, the pharmaceutical formulation for an intravenous administration comprises an anti-IL-36R antibody in an amount of about 60 mg/mL. In a related embodiment, the pharmaceutical formulation for a subcutaneous administration comprises an anti-IL-36R antibody in an amount of about 150 mg/mL. In a related embodiment, the anti-IL-36R antibody comprising: (i) a light chain comprising an amino acid sequence set forth as SEQ ID NO:118 and a heavy chain comprising an amino acid sequence set forth as SEQ ID NO:125; or (ii) a light chain comprising an amino acid sequence set forth as SEQ ID NO:118 and a heavy chain comprising an amino acid sequence set forth as SEQ ID NO:126; or (iii) a light chain comprising an amino acid sequence set forth as SEQ ID NO:118 and a heavy chain comprising an amino acid sequence set forth as SEQ ID NO:127. In a related embodiment, the anti-IL-36R antibody comprising: a light chain variable region comprising the amino acid sequence of SEQ ID NO: 77; and a heavy chain variable region comprising the amino acid sequence of SEQ ID NO: 87; or a light chain variable region comprising the amino acid sequence of SEQ ID NO: 77; and a heavy chain variable region comprising the amino acid sequence of SEQ ID NO: 88; or a light chain variable region comprising the amino acid sequence of SEQ ID NO: 77; and a heavy chain variable region comprising the amino acid sequence of SEQ ID NO: 89; or a light chain variable region comprising the amino acid sequence of SEQ ID NO: 80; and a heavy chain variable region comprising the amino acid sequence of SEQ ID NO: 87; or a light chain variable region comprising the amino acid sequence of SEQ ID NO: 80; and a heavy chain variable region comprising the amino acid sequence of SEQ ID NO: 88; or a light chain variable region comprising the amino acid sequence of SEQ ID NO: 80; and a heavy chain variable region comprising the amino acid sequence of SEQ ID NO: 89.

Examples of antibodies for use in such pharmaceutical formulations are those that comprise a antibody or antibody fragment having the light chain variable region amino acid sequence of any of SEQ ID NO: 1-10. Examples of antibodies for use in such pharmaceutical compositions are also those that comprise a humanized antibody or antibody fragment having the heavy chain variable region amino acid sequence of any of SEQ ID NO: 11-20.

Further examples of antibodies for use in such pharmaceutical formulations are also those that comprise a humanized antibody or antibody fragment having the light chain variable region amino acid sequence of any of SEQ ID NO:76-86. Preferred antibodies for use in such pharmaceutical compositions are also those that comprise a humanized antibody or antibody fragment having the heavy chain variable region amino acid sequence of any of SEQ ID NO:87-101.

Further examples of antibodies for use in such pharmaceutical formulations are also those that comprise a humanized antibody or antibody fragment having the light chain variable region and heavy chain variable region of any of SEQ ID NO: 77 and 89, SEQ ID NO: 80 and 88, SEQ ID NO: 80 and 89, SEQ ID NO: 77 and 87, SEQ ID NO: 77 and 88, SEQ ID NO: 80 and 87, SEQ ID NO: 86 and 100, SEQ ID NO: 85 and 101, or SEQ ID NO: 85 and 10.

Further examples of antibodies for use in such pharmaceutical formulations are also those that comprise a humanized antibody having the light chain region amino acid sequence of any of SEQ ID NO:115, 118, 123 or 124.

Preferred antibodies for use in such pharmaceutical compositions are also those that comprise humanized antibody having the heavy chain variable region amino acid sequence of any of SEQ ID NO:125, 126, 127, 138 or 139.

Further examples of antibodies for use in such pharmaceutical formulations are also those that comprise Antibody B1, Antibody B2, Antibody B3, Antibody B4, Antibody B5, Antibody B6, Antibody C1, Antibody C2 or Antibody C3.

Various delivery systems are known and can be used to administer the IL-36R binding agent. Methods of introduction include but are not limited to intradermal, intramuscular, intravenous, subcutaneous, intranasal, epidural, and oral routes. The IL-36R binding agent can be administered, for example by infusion, bolus or injection, and can be administered together with other biologically active agents such as chemotherapeutic agents. Administration can be systemic or local. In preferred embodiments, the administration is by subcutaneous injection. Formulations for such injections may be prepared in for example prefilled syringes that may be administered once every other week.

In specific embodiments, the IL-36R binding agent formulation is administered by injection, by means of a catheter, by means of a suppository, or by means of an implant, the implant being of a porous, non-porous, or gelatinous material, comprising a membrane, such as a sialastic membrane, or a fiber. Typically, when administering the formulation, materials to which the anti-IL-36R antibody or agent does not absorb are used.

In other embodiments, the anti-IL-36R antibody or agent is delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

An IL-36R binding agent (e.g., an anti-IL-36R antibody) can be administered as pharmaceutical formulations comprising a therapeutically effective amount of the binding agent and one or more pharmaceutically compatible ingredients.

Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical formulation can be provided as a pharmaceutical kit comprising (a) a container containing a IL-36R binding agent (e.g., an anti-IL-36R antibody) in lyophilized form and (b) a second container containing a pharmaceutically acceptable diluent (e.g., sterile water) for injection. The pharmaceutically acceptable diluent can be used for reconstitution or dilution of the lyophilized anti-IL-36R antibody or agent. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the IL-36R binding agent (e.g., anti-IL-36R antibody) that is effective in the treatment or prevention of an immunological disorder or cancer can be determined by standard clinical techniques. In addition, in vitro assays may optionally be employed to help identify optimal dosage ranges. The precise dose to be employed in the formulation will also depend on the route of administration, and the stage of immunological disorder or cancer, and should be decided according to the judgment of the practitioner and each patient's circumstances.

In some embodiments, the pharmaceutical formulations comprising the IL-36R binding agent can further comprise a therapeutic agent, either conjugated or unconjugated to the binding agent. The anti-IL-36R antibody or IL-36R binding agent can be co-administered in combination with one or more therapeutic agents for the treatment or prevention of immunological disorders or cancers.

Such combination therapy administration can have an additive or synergistic effect on disease parameters (e.g., severity of a symptom, the number of symptoms, or frequency of relapse).

With respect to therapeutic regimens for combinatorial administration, in a specific embodiment, an anti-IL-36R antibody or IL-36R binding agent is administered concurrently with a therapeutic agent. In another specific embodiment, the therapeutic agent is administered prior or subsequent to administration of the anti-IL-36R antibody or IL-36R binding agent, by at least an hour and up to several months, for example at least an hour, five hours, 12 hours, a day, a week, a month, or three months, prior or subsequent to administration of the anti-IL-36R antibody or IL-36R binding agent.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a formulation that is effective for treating the condition and may have a sterile access port. For example, the container may be an intravenous solution bag or a vial having a stopper pierceable by a hypodermic injection needle. The active agent in the formulation is the humanized anti-IL-36R antibody. The label on or associated with the container indicates that the formulation is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The invention is further described in the following examples, which are not intended to limit the scope of the invention.

EXAMPLES

Example 1

Conformational and Colloidal Stability (pH and Buffer Screening)

Thermal stability in the pH range of 5.5 to 6.5 was evaluated by monitoring the temperature of unfolding (T(h)) using DSF (Differential Scanning Fluorimetry). The T(h) is the temperature of hydrophobic exposure, which is analogous to and reported here as the $T_m$, thus denoting the temperature of protein unfolding. The samples were diluted with the respective buffers to a target concentration of 0.5 mg/mL for use in thermal stability screening by DSF.

The colloidal stability of the formulations was assessed by DLS (Dynamic Light Scattering). The diffusion coefficient of an antibody of the present invention was measured at several different protein concentrations in different buffers.

The results from the DSF analysis for the pH/buffer screen showed a clear impact of pH on the thermal unfolding temperature $T_m$. Thermal stability data indicated that the conformational stability was slightly increasing with increasing pH. Table 1 shows the buffers that were evaluated and the corresponding $T_m$ in the respective buffers.

TABLE 1 pH/Buffer Screen: Tm Values Determined by DSF Studies

| Buffer | $T_m$ (° C.) |
|---|---|
| Histidine pH 6.5 | 71 |
| Phosphate pH 6.5 | 71 |
| Succinate pH 6.4 | 71 |
| Citrate pH 6.5 | 70 |
| Succinate pH 6.0 | 70 |
| Citrate pH 6.0 | 70 |
| Histidine pH 6.0 | 69 |
| Acetate pH 5.5 | 69 |

The colloidal stability screening study (FIG. 1) showed the surprising results that formulations of an anti-IL-36R antibody (as disclosed herein) in pH 5.5 (25 mM acetate), and pH 6.0 (25 mM histidine) exhibited the most promising properties (minimized protein-protein interaction and highest degree of diffusivity). The colloidal screening assay predicted that acetate (pH 5.5) and histidine (pH 6.0) should have the least amount of protein-protein interactions. The colloidal stability screening study was conducted for the anti-IL-36R antibody at concentrations of 5-20 mg/mL.

Example 2

Chemical Stability Study (2 Weeks at 40° C.)

The chemical stability of an anti-IL-36R antibody of the present invention was evaluated as a function of pH/buffer. Samples were prepared at 80 mg/mL in the pH range of 5.5 to 6.5. Samples were filled with 1 mL in 2 mL glass vials. The samples were incubated at 40° C. for 14 days. Samples were evaluated by i.a. visual assessment, protein concentration (A280), HP-SEC (High Performance Size Exclusion Chromatography) for the determination of monomer content and aggregate formation, and CEX (cation exchange chromatography) for the measurement of charge variants as APGs (acidic peak groups), BPGs (basic peak groups) and the main peak.

The visual assessment of the samples showed that most of the samples became turbid at the end of 14 days. Surprisingly, only samples in 25 mM acetate pH 5.5 remained clear after 14 days at 40° C.

HP-SEC indicated that the most favorable buffer in terms of % main peak remaining after 14 days was 25 mM acetate pH 5.5 (98.5%), followed by 25 mM citrate pH 6.5 (97.5%) and 25 mM citrate pH 6.0 (97.1%). Main peak data after 14 days at 40° C. of further buffers as histidine pH 6.0, phosphate 6.5 and succinate pH 6.4 were between 88.9 to 91.9%.

The CEX data after 14 days at 40° C. indicated the highest % main peak in 25 mM acetate pH 5.5 (54.0%), compared to the other tested buffers (33.3%-44.5%).

The CEX data after 14 days at 40° C. indicated the lowest % acidic peak in 25 mM acetate pH 5.5 (38.1%), compared to the other tested buffers (as high as 58.1%). This buffer had also comparable performance to the other buffers in terms of minimizing the appearance of basic species.

Based on the results obtained by visual assessment, and HP-SEC and CEX, 25 mM acetate pH 5.5 appeared to be the most favorable formulation buffer after the 14 day accelerated stability study.

Although the $T_m$ was lowest for pH 5.5 in the thermal screening study, it was concluded that the conformational stability would be improved by the addition of excluded solute stabilizers (e.g. sucrose). Hence, 25 mM acetate pH 5.5 was selected to be the buffer of choice for an anti-IL-36R antibody of the present invention.

Example 3

Surfactant Study

This working example was conducted to optimize the concentration of polysorbate 20 in four different formulations containing 25 mM acetate at pH 5.5 (Table 2). Samples were filled into 2 mL glass vials (1 mL per vial).

TABLE 2

Formulations Evaluated in Surfactant Optimization Study

| Formulation Matrix | Formulation 1 | Formulation 2 | Formulation 3 | Formulation 4 |
|---|---|---|---|---|
| An anti-IL-36R antibody (as disclosed herein) | 150 mg/mL | 150 mg/mL | 150 mg/mL | 150 mg/mL |
| Acetate | 25 mM | 25 mM | 25 mM | 25 mM |
| Sucrose | 200 mM | 200 mM | 200 mM | 200 mM |
| Polysorbate 20 | 0% (w/v) | 0.02% (w/v) | 0.04% (w/v) | 0.06% (w/v) |

The following experiments were conducted for the surfactant study: freeze-thaw stability, agitation stability. The following assays were used to analyze samples generated from different experiments: i.a. HP-SEC and subvisible particles.

Freeze-Thaw Stability Study

A solution of an anti-IL-36R antibody of the present invention was frozen in glass vials at −40° C. for 24 hours, followed by thawing at room temperature for 2 hours. This procedure was repeated for up to 3 times. The samples were then analyzed by i.a. HP-SEC.

Figure 2:
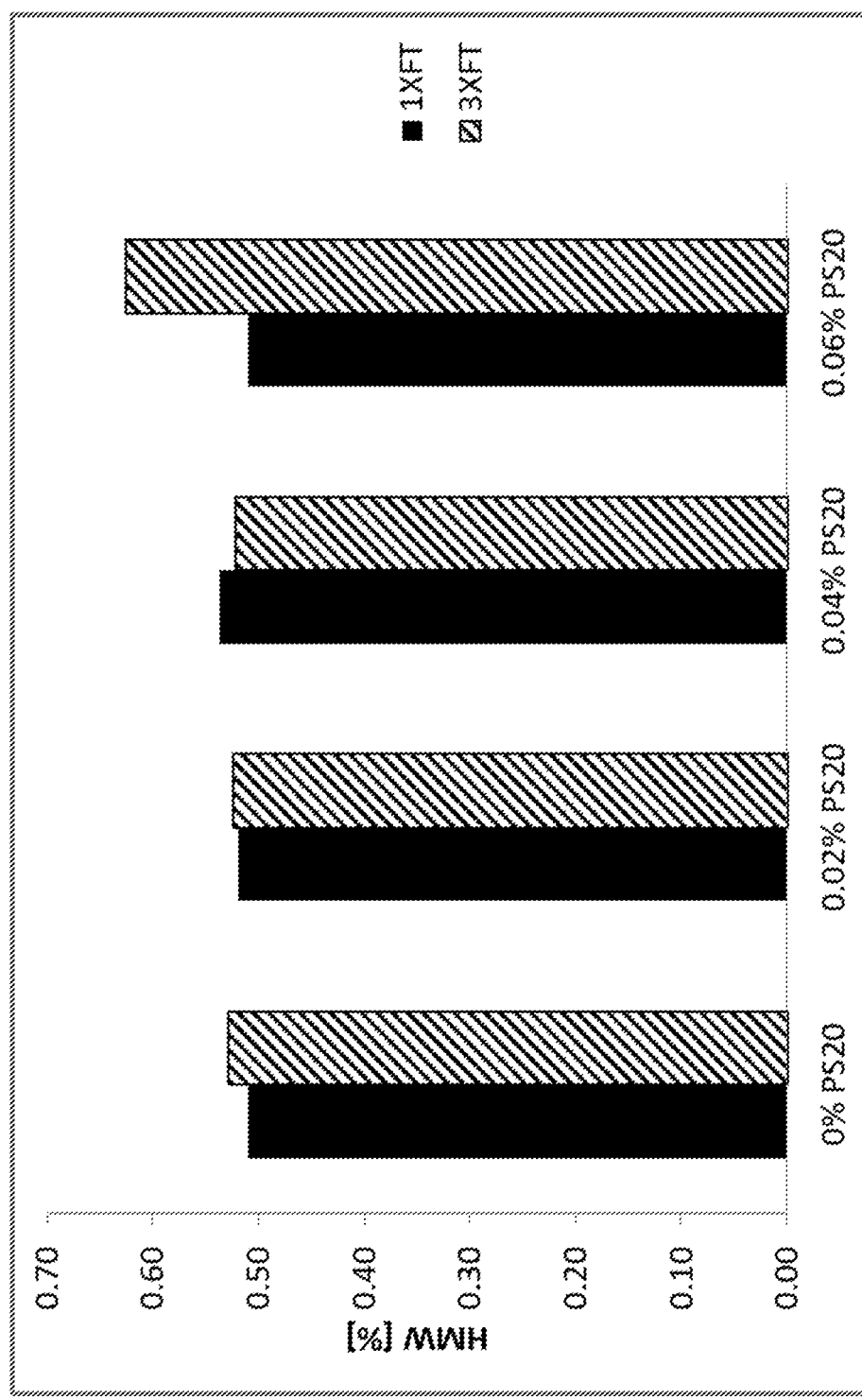
FIG. 2 shows the high molecular weight (HMW) results measured by HP-SEC (Y-axis). Results after one (black columns) and three (shaded columns) freeze—thaw cycle (FT) with polysorbate 20 (PS20) amounts of 0, 0.02, 0.04 and 0.06% (w/v) are provided.

Surprisingly, HP-SEC results showed that formulations with 0.06% polysorbate 20 had elevated levels of high molecular weight species after three freeze-thaw cycles (FIG. 2), relative to other formulations with lower concentrations of polysorbate 20. Those formulations with polysorbate 20 concentrations between 0 and 0.04% performed equally well and slightly better than the formulation with 0.06% polysorbate 20.

Agitation Stability

The agitation study was performed with a shaker at room temperature for 48 hours. Analysis was performed by i.a. HP-SEC and flow imaging microscopy to measure subvisible particle (SVP) content.

Figure 3:
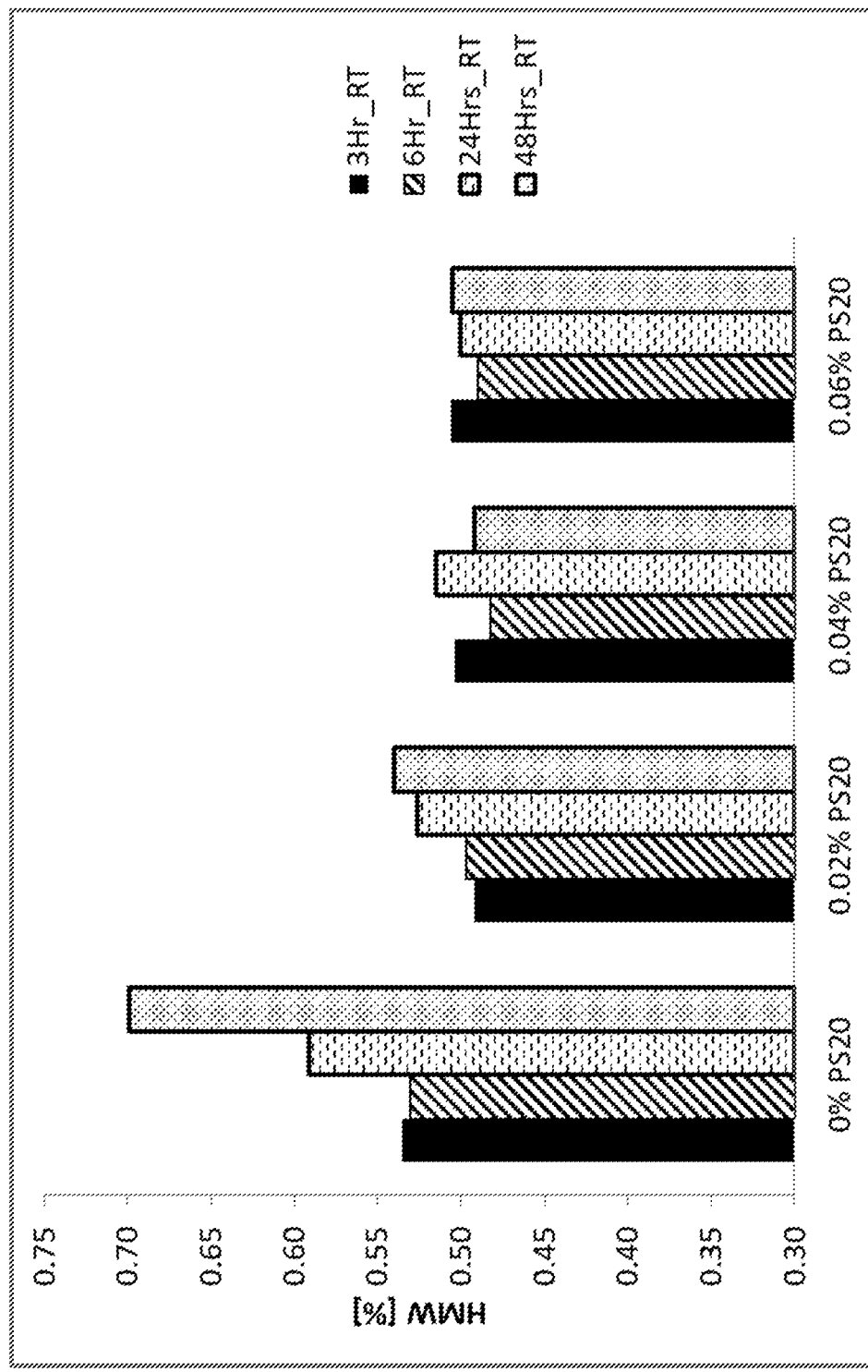
FIG. 3 shows the high molecular weight (HMW) results measured by HP-SEC (Y-axis). Solution with polysorbate 20 (PS20) concentrations of 0, 0.02, 0.04 and 0.06% (w/v) were shaken. Results are shown after 3, 6, 24 and 48 hours of shaking at room temperature (RT).

HP-SEC results indicated a slight increase in aggregation when polysorbate 20 was not present (FIG. 3). All other formulations had similar aggregate levels at each sampling point.

Surprisingly, SVP results showed the formulation with 0.04% PS20 to have the lowest number of subvisible particles after agitation for 48 hours (Table 3).

TABLE 3

SVP results for agitation stability (surfactant optimization)

| Sample Name | Particles/mL Diameter 10-25 μm | Particles/mL Diameter 25 μm and larger |
|---|---|---|
| 0% polysorbate 20 agitation (48 hours) | 3854 | 277 |
| 0.02% polysorbate 20 agitation (48 hours) | 1178 | 149 |
| 0.04% polysorbate 20 agitation (48 hours) | 139 | 15 |
| 0.06% polysorbate 20 agitation (48 hours) | 273 | 36 |

Raising the concentration of polysorbate 20 above 0.04% (w/v) resulted unexpectedly in a slight increase in sample aggregation of freeze-thaw samples. On the other hand, agitation studies showed that removing polysorbate 20 resulted in slightly higher aggregation. Additionally after agitation, SVP were higher at polysorbate 20 concentrations above and below 0.04% (w/v), which was not expected. Based on these results, the final concentration of polysorbate 20 was chosen to be 0.04% (w/v). Additionally studies showed that 0.04% (w/v) polysorbate 20 were also feasible for solution containing 60 mg/mL protein.

Example 4

Final Formulation Screening Study

Based on the initial screening data, six candidate formulations (Table 4) were chosen to be tested in the final formulation screening with an anti-IL-36R antibody of the present invention at 150 mg/mL. Arginine HCl and NaCl were added to evaluate their potential to reduce protein-protein interactions. Reduction of protein-protein interactions can reduce aggregation and decrease viscosity.

TABLE 4

Formulation Compositions for Final Formulation Screening

| Formulation | Sugar | Polysorbate 20 | Buffer | pH | Further excipients |
|---|---|---|---|---|---|
| F1 | 200 mM sucrose | 0.04% | 45 mM acetate | 5.5 | — |
| F2 | 150 mM sucrose | 0.04% | 45 mM acetate | 5.5 | 25 mM arginine HCl |
| F3 | 150 mM sucrose | 0.04% | 45 mM acetate | 5.5 | 25 mM NaCl |
| F4 | 200 mM trehalose | 0.04% | 45 mM acetate | 5.5 | — |

TABLE 4-continued

Formulation Compositions for Final Formulation Screening

| Formulation | Sugar | Polysorbate 20 | Buffer | pH | Further excipients |
|---|---|---|---|---|---|
| F5 | 150 mM trehalose | 0.04% | 45 mM acetate | 5.5 | 25 mM arginine HCl |
| F6 | 150 mM trehalose | 0.04% | 45 mM acetate | 5.5 | 25 mM NaCl |

The following experiments were conducted for the final formulation screening of the six candidate formulations: Eight Weeks Accelerated Stability Study, Freeze-Thaw Stability, Agitation Stability and Photo Stability.

Eight Weeks Accelerated Stability Study

The protein concentration for all the formulations was 150 mg/mL, measured values for concentration fell within 155-166 mg/mL. The samples were filled into 2 mL glass vials (1 mL per vial). The acetate concentration was 45 mM. Samples were stored at three different temperatures (5° C., 25° C., 40° C.). The samples were analyzed by the following assays: i.a. subvisible particles, HP-SEC, IL-36R-Binding (potency), Non-Reduced CGE (capillary gel electrophoresis to detect fragments) and icIEF (imaged capillary isoelectric focusing to measure charge variants.) Subvisible Particles (SVP)

The monitoring of subvisible particles in candidate formulations was performed by flow imaging microscopy. Surprisingly, for samples stored at 5, 25, and 40° C., no clear trends were observed in the counts of particles with diameter 10-25 μm or 25 μm and larger. In both categories, all six formulations showed similar results with low sub-visible particle counts at the end of the eight week study.

icIEF

A generic charge profile for an anti-IL-36R antibody of the present invention display acidic, basic, and main peak groups. The charge variants of an anti-IL-36R antibody of the present invention after 8 weeks at 40° C. appeared to trend very similarly between the formulations.

Non-Reduced CGE

In order to assess the fragmentation and disulfide bond reduction of an anti-IL-36R antibody of the present invention formulations upon storage, results from non-reduced capillary gel electrophoresis were evaluated. A similar degree of fragmentation and disulfide bond reduction (% LMW) was observed for all the formulations at the three storage temperatures.

HP-SEC

Figure 4:
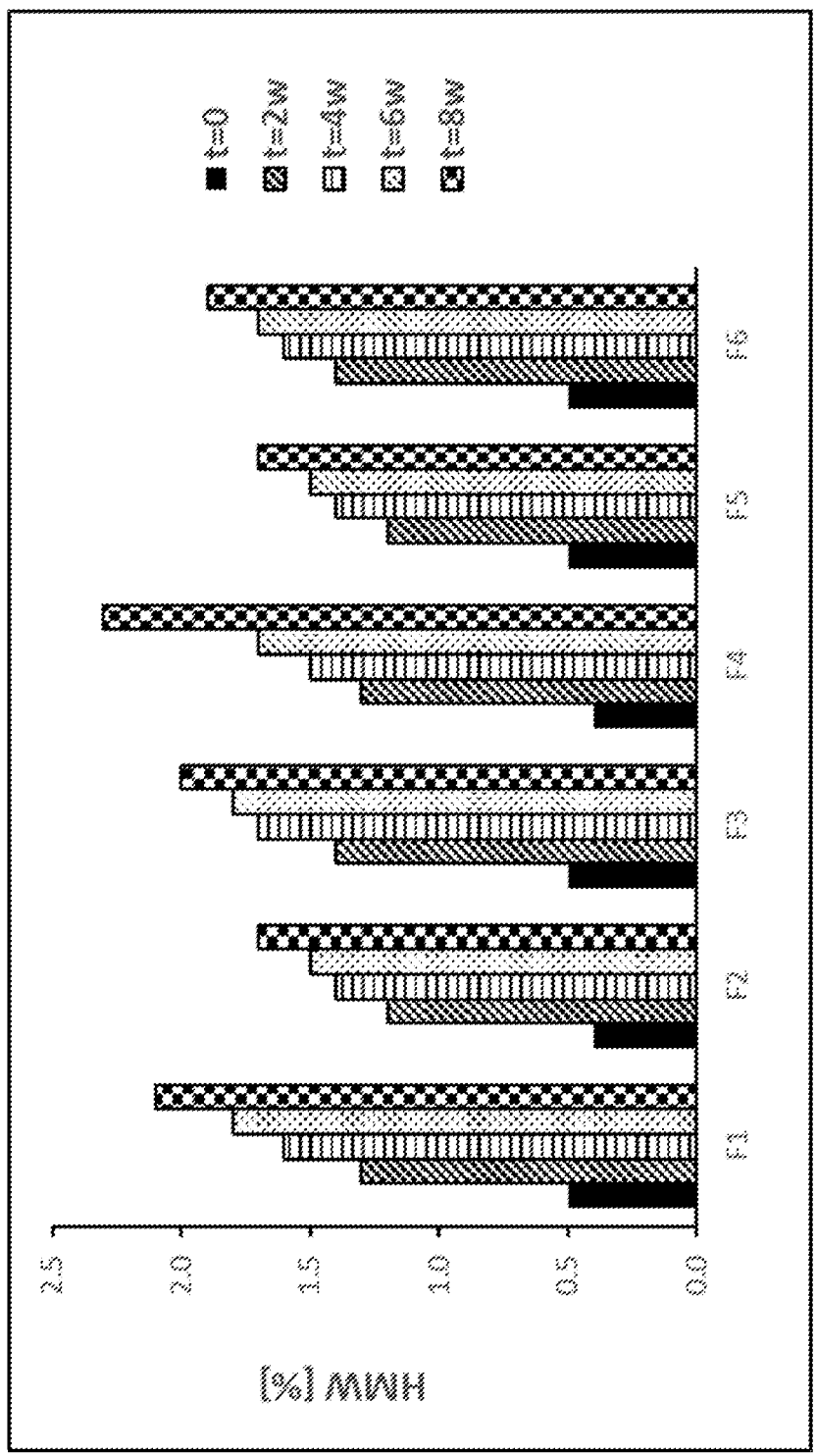
FIG. 4 shows high molecular weight (HMW) results measured by HP-SEC (Y-axis). Six formulations (F1 to F6) with anti-IL-36R antibody at a target protein concentration of 150 mg/mL were stored at 40° C. Data after storage for 0, 2, 4, 6 and 8 weeks (8w) are pictured on the X-axis.

The stability of formulations with respect to aggregation (% HMW) in candidate formulations was assessed by HP-SEC. F2 and F5 exhibited lower % HMW after 8 weeks at 25° C. and 40° C. (FIG. 4).

Potency

The potency of an antibody of the anti-IL-36R present invention formulation candidates was assessed using a binding assay. Remarkably, the potency of all six formulations appears stable even after storage at 40° C. for eight weeks.

Freeze-Thaw Stability of Candidate Formulations

An anti-IL-36R antibody of the present invention solution (1 mL) was filled into 2 mL glass vials (1 mL per vial) and frozen at −40° C., followed by thawing at room temperature. This procedure was repeated for a total of 3 cycles. The following assays were utilized for analysis: visual assessment, pH, protein concentration, HP-SEC, Non-Reduced CGE, and subvisible particles.

Notably, all results of the analytical methods revealed that the six formulations performed equally well.

Agitation Stability of Candidate Formulations

The solution of an anti-IL-36R antibody of the present invention was filled into 2 mL glass vials (1 mL per vial). Samples were shaken for 48 h at room temperature. The samples were analyzed by: i.a. pH, protein concentration, visual assessment, HP-SEC, Non-Reduced CGE, and icIEF.

Surprisingly, agitation did not have any impact on the performance of the six formulations in the assessed analytical results.

Photo Stability of Candidate Formulations

The six formulations were filled into 2 mL glass vials (1 mL per vial), stoppered, and capped. The vials were placed at room temperature at a light intensity of approximately 1100 lux for 5 days. The samples were analyzed using the following assays: visual assessment, protein concentration, pH, HP-SEC, icIEF, and Non-Reduced CGE.

The results of visual assessment, pH, protein concentration, icIEF and Non-Reduced CGE showed that there was no impact of light exposure for any of the formulations tested.

A slight impact on main peak content in HP-SEC was observed, but the decrease was lowest for F5 after 5 days at room temperature and light exposure (Table 5). In principle all formulations were unexpectedly stable against light exposure.

TABLE 5

% Main Peak from Photo stability Study by HP-SEC

| Formulation | F1 | F2 | F3 | F4 | F5 | F6 |
|---|---|---|---|---|---|---|
| 5 days with light | 99.0 | 99.0 | 98.8 | 99.0 | 99.4 | 98.9 |

Summary of Final Formulation Screening Study

Surprisingly, evaluation of the data from the eight-weeks accelerated stability study showed that all the formulations performed equally well when assessed by various assays. The only exception to this was that formulation F2 and F5 appeared slightly more stable than the other formulations regarding high molecular weight species after eight weeks of storage, particularly at 25 and 40° C. This indicates that arginine imparts a positive impact by reducing protein-protein interaction for an anti-IL-36R antibody of the present invention, thereby reducing aggregation propensity. Furthermore, F5 showed slightly less loss of main peak in the photo exposure study.

Example 5

Viscosity of Different Proteins and Formulations

Lower viscosity of protein formulations is beneficial especially for home use and self-administration by patients themselves. Protein solution with lower viscosity can be injected comfortably. Additionally based on low viscosity thin syringe needles could be used and the injection force is still acceptable. Due to the thin needles injection pain is reduced.

However high concentrated protein solutions typically show high viscosity.

Figure 5:
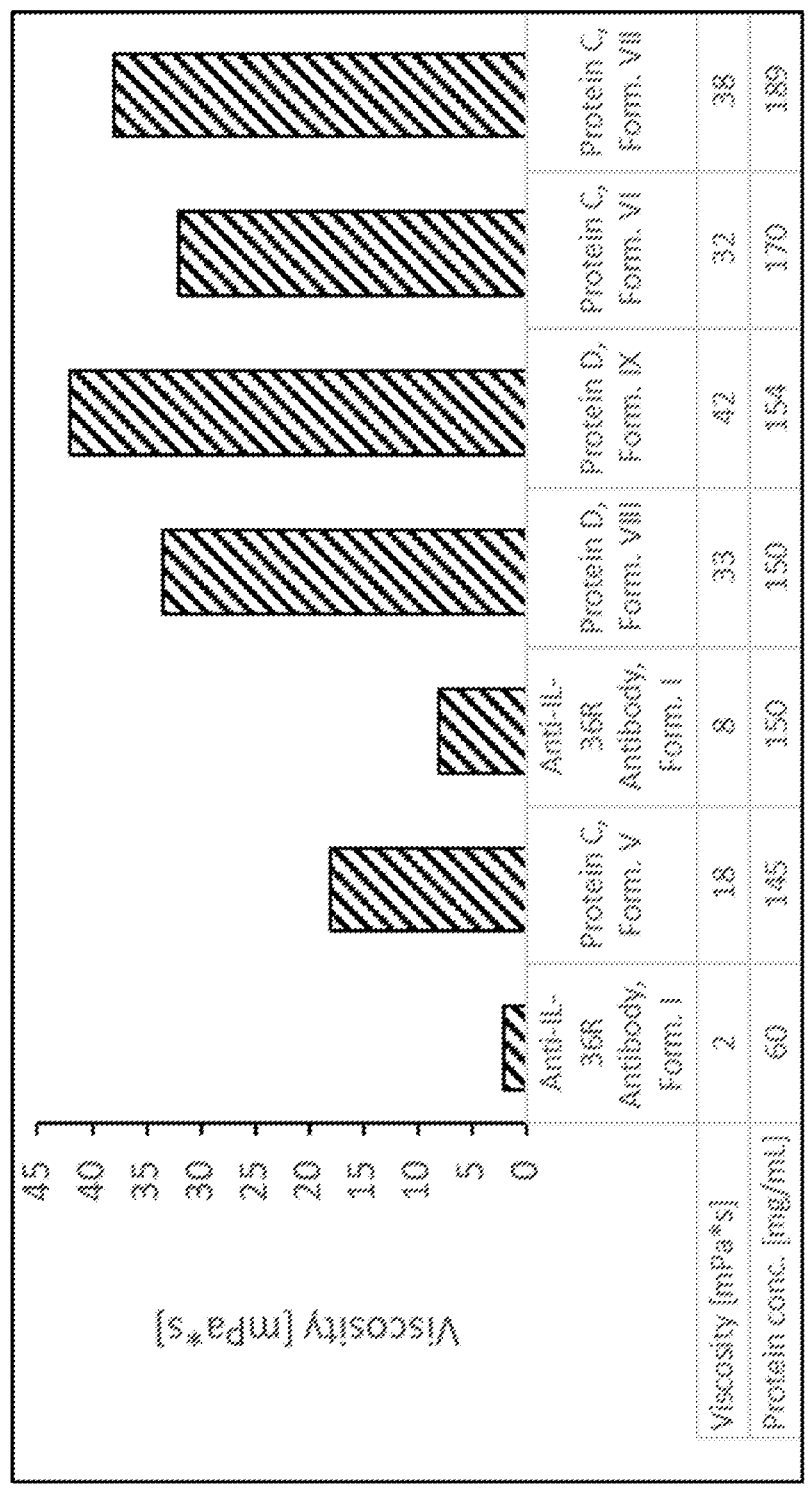
FIG. 5 shows viscosity data of different proteins (Anti-IL-36R Antibody, Protein C, Protein D) and different formulations (Form. I, Form. V, Form. VIII, Form. IX, Form. VI, Form. VII) with protein concentrations of 145 to 189 mg/mL at 20° C. Additionally viscosity data of anti-IL-36R antibody at a protein concentration of 60 mg/mL is given. Viscosity values are shown on Y-axis. Protein formulations with increasing protein concentration are given on X-axis.

Viscosity data of different proteins and formulations at 20° C. are shown in FIG. 5. The data were generated with a Thermo Scientific Haake rheometer (Mars III) and a plate and cone measuring geometry. Examples of different proteins with protein concentration from 145 to 189 mg/mL are added. Data are illustrated on the X-axis with increasing protein concentration. Additionally the viscosity data for anti-IL-36R antibody at 60 mg/mL is exemplarily added in order the show the effect of protein concentration on viscosity (lower protein concentration results in lower viscosity). Compared to typical high concentrated protein solutions, anti-IL-36R antibody solutions have unexpected low viscosity values.

Example 6

Final Formulation Long-Term Stability Study

Two formulations (Table 6) were chosen to be tested in a long-term stability study. Two formulations with an anti-IL-36R antibody of the present invention were held at 5° C. for at least 30 months.

TABLE 6

Formulation Compositions for Long-term Stability Study

| Formu-lation | Anti-IL-36R antibody concentration | Sugar | Surfactant | Buffer | pH | Further ex-cipients |
|---|---|---|---|---|---|---|
| F1 | 20 mg/mL | 200 mM sucrose | Polysorbate 80 at 0.04% | 25 mM citrate | 6.5 | NA |
| F2 | 150 mg/mL | 150 mM sucrose | Polysorbate 20 at 0.04% | 45 mM acetate | 5.5 | 25 mM arginine HCl |

30 Months Stability Study

The stability of each formulation was monitored at 0, 1, 3, 6, 9, 12, 18, 24 and 30 or 36 months. The samples were analyzed by the following assays: i.a. subvisible particles, HP-SEC, IL-36R-Binding (potency), Non-Reduced CGE (capillary gel electrophoresis to detect fragments) and icIEF (imaged capillary isoelectric focusing to measure charge variants.)

Subvisible Particles (SVP)

The monitoring of subvisible particles in candidate formulations was performed by flow light obscuration. Surprisingly, for samples stored for 30 months at 5° C., low numbers of particles were observed with diameter 10-25 μm or 25 μm and larger for both F1 and F2 after at least 30 months of storage at 5° C. (data not shown).

icIEF

A generic charge profile for an anti-IL-36R antibody of the present invention display acidic, basic, and main peak groups. There was very little change in the charge profile after at least 30 months of storage at 5° C. for both F1 and F2 (data not shown).

Non-Reduced CGE

In order to assess the fragmentation and disulfide bond reduction of an anti-IL-36R antibody of the present invention formulations upon storage, results from non-reduced capillary gel electrophoresis were evaluated. Very low levels of fragmentation and disulfide bond reduction (% LMW) were observed after at least 30 months of storage at 5° C. for both F1 and F2 (data not shown).

HP-SEC

Figure 6:
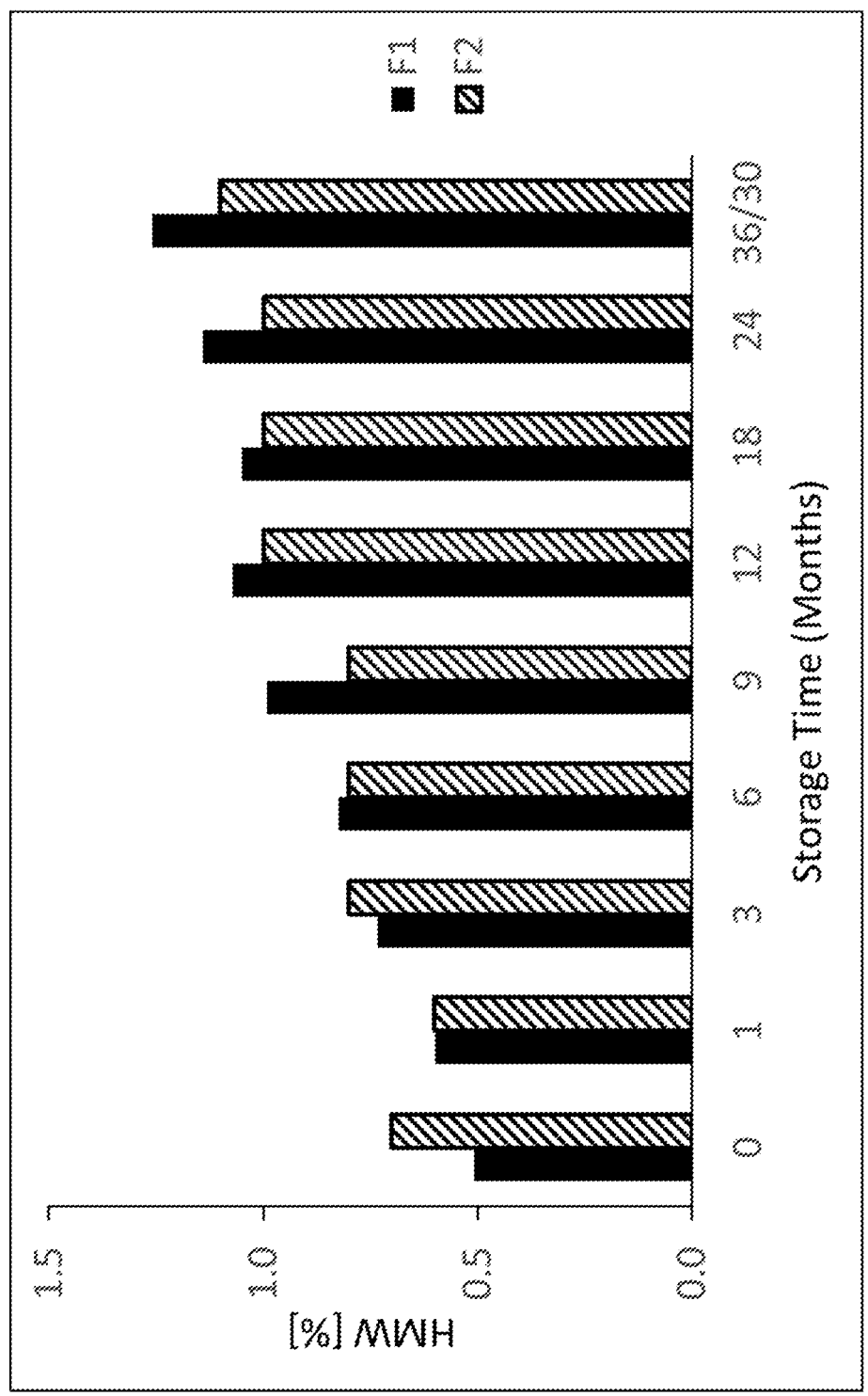
FIG. 6 shows high molecular weight (HMW) results measured by HP-SEC (Y-axis). Two formulations (F1 and F2) were stored at 2-8° C. Data after storage up to 36 months for F1 and 30 months for F2 are depicted.

The stability of formulations with respect to aggregation (% HMW) was assessed by HP-SEC. Surprisingly, F1 and F2 exhibited very low % HMW after at least 30 months of storage at 5° C. (FIG. 6).

Potency

The potency of an antibody of the anti-IL-36R present invention formulation candidates was assessed using a binding assay. Remarkably, the potency of F1 and F2 appears stable even after at least 30 months of storage at 5° C. (data not shown).

Summary of Long-term Stability Studies

Evaluation of the data from the 30-month stability study showed that both F1 and F2 performed equally well when assessed by various assays. Remarkably, formulations showed very low % HMW content after at least 30 months of storage.

Example 7

Accelerated Stability Study

Two formulations (Table 7) were chosen to be tested in a stability study under stress conditions. Two formulations with an anti-IL-36R antibody of the present invention were held at 40° C. for up to three months in 10 mL glass vials (8 mL per vial). Formulation F2 represents a reference formulation that can be used for parenteral administration.

TABLE 7

Formulation Composition for Accelerated Stability Study

| Formulation Matrix | Formulation F1 | Formulation F2 |
|---|---|---|
| Anti-IL-36R antibody concentration | 60 mg/mL | 60 mg/mL |
| Acetate | 45 mM | 0 mM |
| Citrate | 0 mM | 25 mM |
| Sucrose | 150 mM | 0 mM |
| L-Arginine HCl | 25 mM | 0 mM |
| PS20 | 0.04% (w/v) | 0.04% (w/v) |
| pH | 5.5 | 6.5 |

Turbidity

Figure 7:
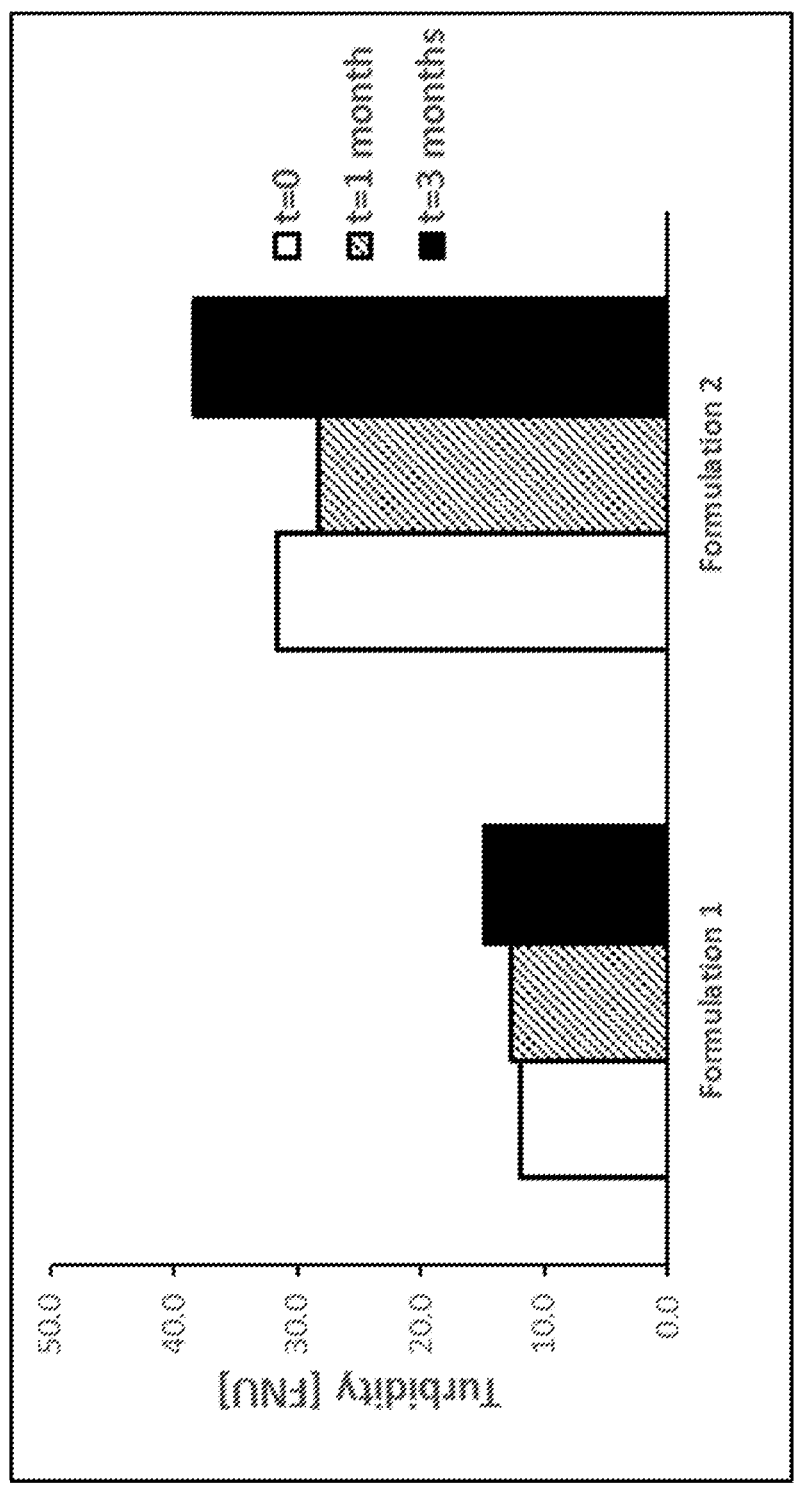
FIG. 7 shows turbidity results analyzed by 90° light scattering at 400-600 nm (Y-axis). Data after storage up to 3 months at stress conditions at 40° C. for F1 and F2 (reference formulation) are shown on the X-axis.

The stability of the two formulations was monitored at 0, 1, and 3 months. The samples were analyzed by measurement of turbidity. Turbidity was analyzed by 90° light scattering with a Hach Lange TL2350 turbidity meter at 400-600 nm. The data is shown in FIG. 7. Formulation F2 showed an at least twice as high turbidity result as Formulation F1. Formulation F1 surprisingly exhibited a very low turbidity from the initial sampling time point over the course of the study up to three months.

HP-SEC

Figure 8:
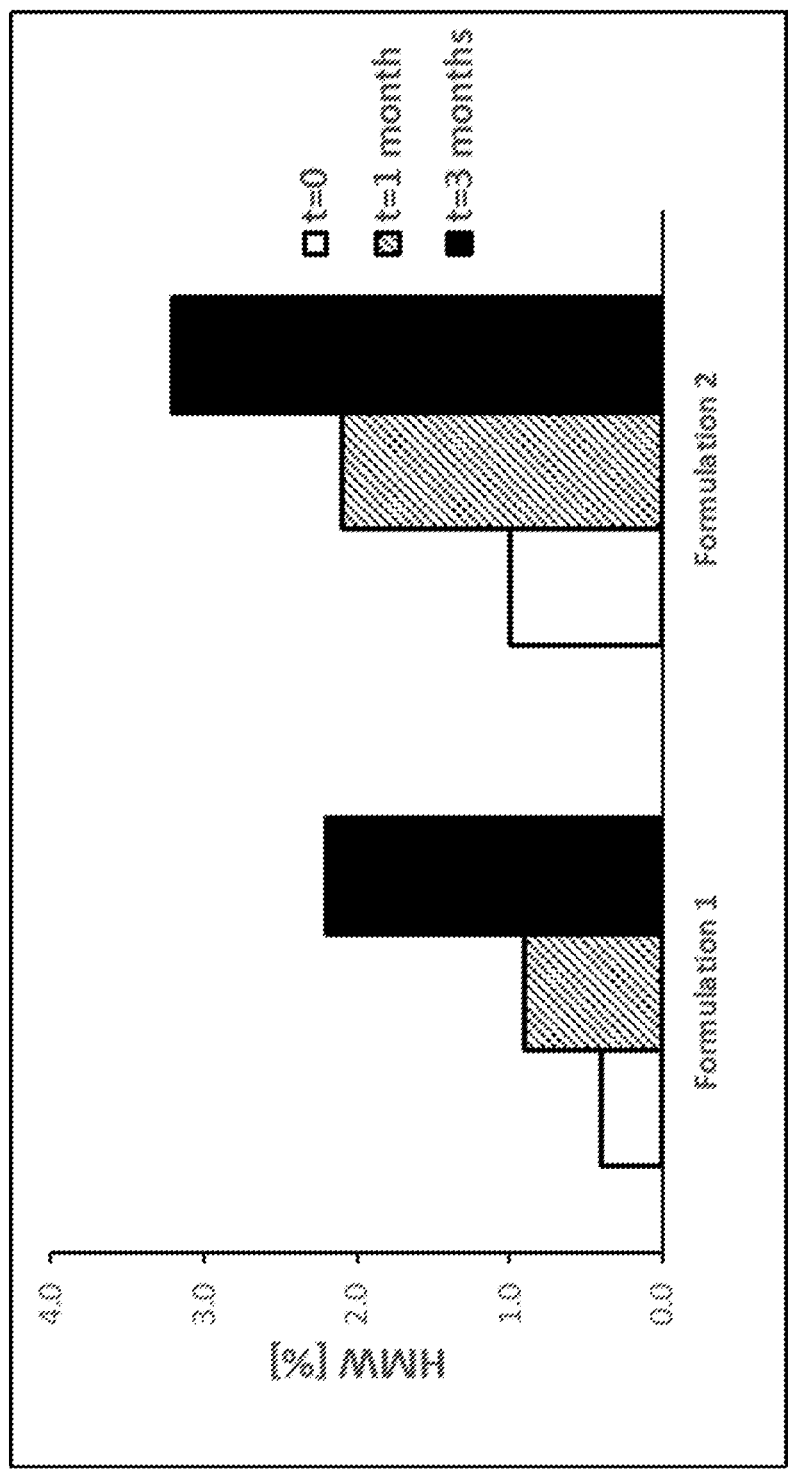
FIG. 8 shows high molecular weight (HMW) results measured by HP-SEC. Data after storage up to 3 months at stress conditions at 40° C. for F1 and F2 (reference formulation) are depicted.

The stability of formulations with respect to aggregation (% HMW) was assessed by HP-SEC. The data is depicted in FIG. 8. Unexpectedly, the Formulation F1 exhibited a very low % HMW from the initial sampling time point on over the course of the study up to three months, compared to the reference Formulation F2. The % HMW is at least 45% higher for the reference Formulation F2 compared to the Formulation F1.

Summary of Accelerated Stability Study

Evaluation of the data from the three months stability study under stress conditions at 40° C. showed at least twice as high turbidity results of reference Formulation F2 in correlation to Formulation F1. Furthermore, the Formulation F1 exhibited a very low % HMW from the initial sampling time point over the course of the study up to three months, compared to the reference Formulation F2.

Example 8

Stability Lyophilized Formulation

The stability of the lyophilized formulation in 6 mL glass vials with 2.5 mL of an anti-IL-36R antibody formulation (Table 8) using a standard lyophilization process was evaluated. The samples were stored at 40° C. for up to 6 months.

TABLE 8

| Formulation Composition | | | | | |
|---|---|---|---|---|---|
| Anti-IL-36R antibody concentration | Sugar | Surfactant | Buffer | pH | Further excipients |
| 60 mg/mL | 160 mM sucrose | Polysorbate 20 at 0.02% (w/v) | 25 mM histidine | 6.0 | 20 mM mannitol |

The stability of the formulation was monitored prior to lyophilization, directly after lyophilization and reconstitution, as well as after 1, 3 and 6 months of storage at 40° C. The samples were analyzed by the following assays: i.a. turbidity, subvisible particles and aggregate levels by HP-SEC.

Turbidity

Figure 9:
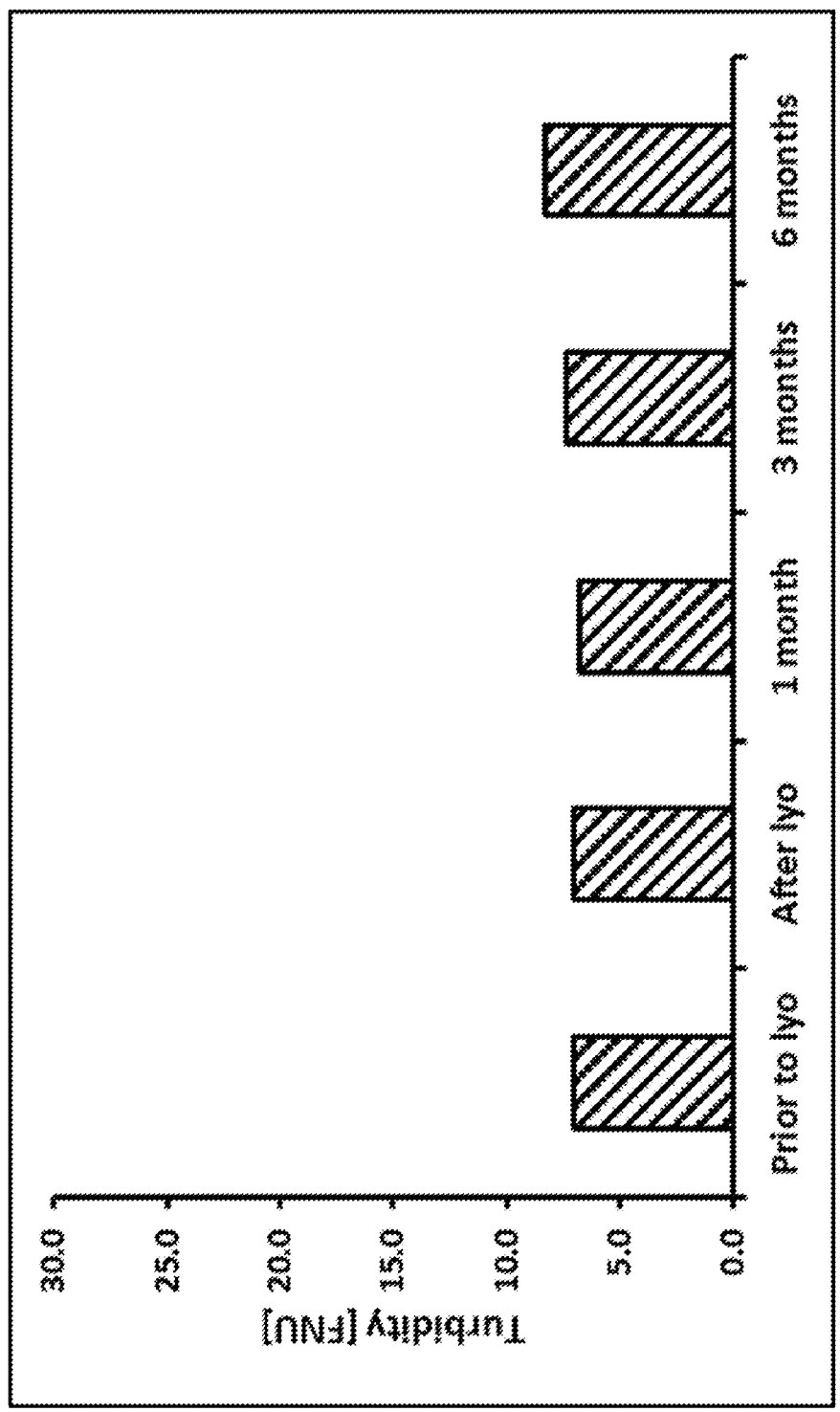
FIG. 9 shows turbidity results analyzed by 90° light scattering at 400-600 nm (Y-axis). Data prior to lyophilization, after lyophilization as well as after storage of the lyophilized powder formulation up to 6 months at stressed conditions at 40° C. are given on the X-axis.

Turbidity was measured by 90° light scattering (A=400-600 nm) with a Hach Lange TL2350 turbidity meter. The tested formulation exhibited a low turbidity that was not impacted by the lyophilization step. Surprisingly, the turbidity value did not increase after 6 months of storage at 40° C. (FIG. 9).

HP-SEC

Figure 10:
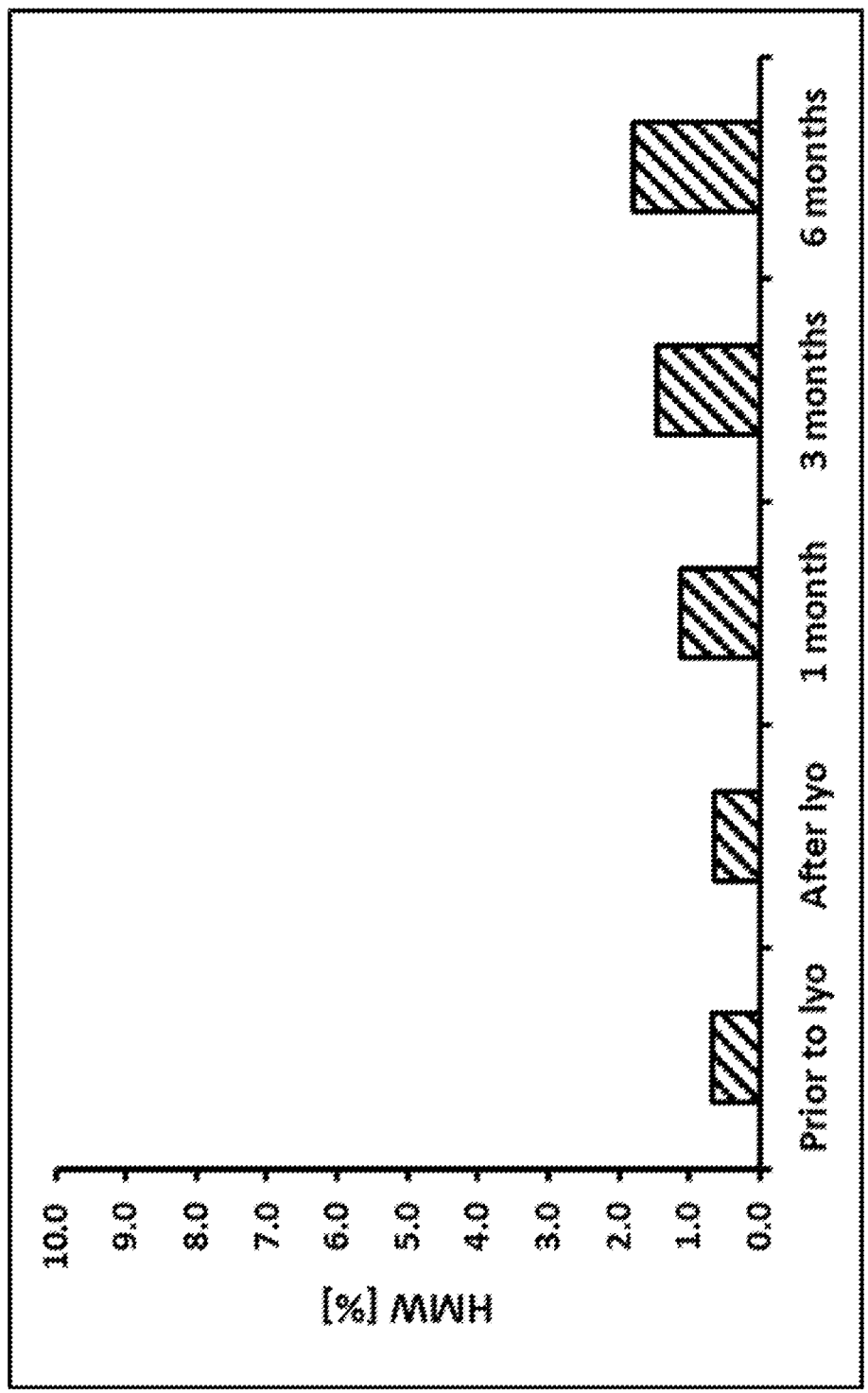
FIG. 10 shows high molecular weight (HMW) results measured by HP-SEC (Y-axis). Data prior to lyophilization, after lyophilization as well as after storage of the lyophilized powder formulation up to 6 months at stressed conditions at 40° C. are depicted.

Besides, the stability of the powder formulation with respect to aggregation (% HMW) was performed by HP-SEC. Freeze-concentration and stresses at the ice-water interface arising during lyophilization did unexpectedly not lead to the formation of protein aggregates. Moreover, the powder formulation showed very low % HMW after at least 6 months of storage at 40° C. (FIG. 10).

Summary Stability Lyophilized Formulation

Evaluation of the data from this study surprisingly showed the feasibility to lyophilize an anti-IL36R antibody formulation without any impact on protein quality. Furthermore, the subsequent stability study under stressed conditions at 40° C. confirmed the extraordinary stability of the anti-IL-36R antibody in the aforementioned powder formulation.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

Throughout this application, various publications (patent or non-patent literature) are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

The invention claimed is:

1. An antibody formulation comprising:
   (a) an anti-Interleukin-36 receptor (anti-IL-36R) antibody or an antigen binding fragment thereof present at a concentration within the range from about 10 mg/mL to about 200 mg/mL;
   (b) an acetate buffer present at a concentration of about 45 mM;
   (c) sucrose present at a concentration of about 150 mM;
   (d) L-arginine or a pharmaceutically acceptable salt thereof present at a concentration of about 25 mM; and
   (e) polysorbate 20 present at a concentration of about 0.4 g/L;
   wherein the formulation in liquid form or when reconstituted with water is characterized by a pH within the range from about 5 to about 6; and
   further wherein the anti-IL-36R antibody or an antigen binding fragment thereof is selected from the following:
   (i) an antibody or an antigen binding fragment thereof comprising a light chain variable region comprising the amino acid sequence of SEQ ID NO: 80; and a heavy chain variable region comprising the amino acid sequence of SEQ ID NO: 87; or
(ii) an antibody or an antigen binding fragment thereof the amino acid sequence of SEQ ID NO: 80; and a heavy chain variable region comprising the amino acid sequence of SEQ ID NO: 88; or
(iii) an antibody or an antigen binding fragment thereof the amino acid sequence of SEQ ID NO: 80; and a heavy chain variable region comprising the amino acid sequence of SEQ ID NO: 89.

2. The antibody formulation of claim 1, wherein the antibody is present at a concentration of about 20 mg/mL, about 60 mg/mL or about 150 mg/mL.

3. The antibody formulation of claim 1, wherein the antibody is present at a concentration of about 60 mg/mL.

4. The antibody formulation of claim 1, wherein the antibody is present at a concentration of about 150 mg/mL.

5. The antibody formulation of claim 1, wherein the L-arginine or a pharmaceutically acceptable salt thereof comprises arginine HCl.

6. The antibody formulation of claim 1, wherein the anti-IL-36R antibody or an antigen binding fragment thereof comprises light chain variable region comprising the amino acid sequence of SEQ ID NO: 80; and a heavy chain variable region comprising the amino acid sequence of SEQ ID NO: 87.

7. The antibody formulation of claim 1, wherein the anti-IL-36R antibody or an antigen binding fragment thereof comprises a light chain variable region comprising the amino acid sequence of SEQ ID NO:80; and a heavy chain variable region comprising the amino acid sequence of SEQ ID NO:88.

8. The antibody formulation of claim 1, wherein the anti-IL-36R antibody or an antigen binding fragment thereof comprises a light chain variable region comprising the amino acid sequence of SEQ ID NO: 80; and a heavy chain variable region comprising the amino acid sequence of SEQ ID NO: 89.

9. The antibody formulation of claim 1, wherein the formulation in liquid form or when reconstituted with water is characterized by a pH of about 5.5.

10. An antibody formulation according to claim 1, wherein said formulation is suitable for intravenous, subcutaneous or intramuscular administration.

11. An antibody formulation according to claim 1, wherein less than about 5% of the antibody is present in an aggregate form in the formulation.

12. An antibody formulation according to claim 1, wherein the formulation is sterile.

13. An antibody formulation according to claim 1, wherein the formulation is stable upon freezing and thawing.

14. An antibody formulation according to claim 1, wherein the formulation comprises water or is reconstituted with water.

15. A pharmaceutical product comprising a vial or syringe comprising an antibody formulation according to claim 1.

16. A pharmaceutical product according to claim 15 further comprising an injection device, which comprises an autoinjector or needle safety device, and which device provides for subcutaneous or intramuscular administration of said antibody formulation.

17. An antibody formulation consisting essentially of:
(a) an anti-Interleukin-36 receptor (anti-IL-36R) antibody or an antigen binding fragment thereof present at a concentration within the range from about 10 mg/mL to about 200 mg/mL;
(b) an acetate buffer present at a concentration of about 45 mM;
(c) sucrose present at a concentration of about 150 mM;
(d) L-arginine or a pharmaceutically acceptable salt thereof present at a concentration of about 25 mM; and
(e) polysorbate 20 present at a concentration of about 0.4 g/L;
wherein the formulation in liquid form or when reconstituted with water is characterized by a pH within the range from about 5 to about 6; and
further wherein the anti-IL-36R antibody or an antigen binding fragment thereof is selected from the following:
(i) an antibody or an antigen binding fragment thereof comprising a light chain variable region comprising the amino acid sequence of SEQ ID NO: 80; and a heavy chain variable region comprising the amino acid sequence of SEQ ID NO: 87; or
(ii) an antibody or an antigen binding fragment thereof comprising a light chain variable region comprising the amino acid sequence of SEQ ID NO: 80, and a heavy chain variable region comprising the amino acid sequence of SEQ ID NO: 88; or
(iii) an antibody or an antigen binding fragment thereof comprising a light chain variable region comprising the amino acid sequence of SEQ ID NO: 80; and a heavy chain variable region comprising the amino acid sequence of SEQ ID NO: 89.

18. The antibody formulation of claim 17, wherein the formulation in liquid form or when reconstituted with water is characterized by a pH of about 5.5.

19. An antibody formulation according to claim 17, wherein said formulation is suitable for intravenous, subcutaneous or intramuscular administration.

20. An antibody formulation according to claim 17, wherein less than about 5% of the antibody is present in an aggregate form in the formulation.

21. An antibody formulation according to claim 17, wherein the formulation is sterile.

22. An antibody formulation according to claim 17, wherein the formulation is stable upon freezing and thawing.

23. An antibody formulation according to claim 17, wherein the formulation comprises water or is reconstituted with water.

24. A pharmaceutical product comprising a vial or syringe comprising an antibody formulation according to claim 17.

25. A pharmaceutical product according to claim 24 further comprising an injection device, which comprises an autoinjector or needle safety device, and which device provides for subcutaneous or intramuscular administration of said antibody formulation.

26. An antibody formulation comprising:
(a) an anti-IL-36R antibody comprising:
(i) a light chain comprising the amino acid sequence of SEQ ID NO: 118 and a heavy chain comprising the amino acid sequence of SEQ ID NO:125; or
(ii) a light chain comprising the amino acid sequence of SEQ ID NO: 118 and a heavy chain comprising the amino acid sequence of SEQ ID NO:126; or
(iii) a light chain comprising the amino acid sequence of SEQ ID NO: 118 and a heavy chain comprising the amino acid sequence of SEQ ID NO: 127;
wherein the antibody is present at a concentration within the range from about 10 mg/mL to about 200 mg/mL;
(b) acetate buffer present at a concentration of about 45 mM;

(c) sucrose present at a concentration of about 150 mM;
(d) L-arginine HCl present at a concentration of about 25 mM;
(e) polysorbate 20 present at a concentration of about 0.4 g/L; and
wherein the formulation in liquid form or when reconstituted with water is characterized by a pH within the range from about 5 to about 6.

27. The antibody formulation of claim 26, wherein the antibody is present at a concentration of about 20 mg/mL, about 60 mg/mL or about 150 mg/mL.

28. The antibody formulation of claim 26, wherein the antibody is present at a concentration of about 60 mg/mL.

29. The antibody formulation of claim 26, wherein the antibody is present at a concentration of about 150 mg/mL.

30. The antibody formulation of claim 26, wherein the antibody comprises a light chain comprising the amino acid sequence of SEQ ID NO:118 and a heavy chain comprising the amino acid sequence of SEQ ID NO:125.

31. The antibody formulation of claim 26, wherein the antibody comprises a light chain comprising the amino acid sequence of SEQ ID NO:118 and a heavy chain comprising, the amino acid sequence of SEQ ID NO:126.

32. The antibody formulation of claim 26, wherein the antibody comprises a light chain comprising the amino acid sequence of SEQ ID NO:118 and a heavy chain comprising the amino acid sequence of SEQ ID NO:127.

33. The antibody formulation of claim 26, wherein the formulation in liquid form or when reconstituted with water is characterized by a pH of about 5.5.

34. An antibody formulation according to claim 26, wherein said formulation is suitable for intravenous, subcutaneous or intramuscular administration.

35. An antibody formulation according to claim 26, wherein less than about 5% of the antibody is present in an aggregate form in the formulation.

36. An antibody formulation according to claim 26, wherein the formulation is sterile.

37. An antibody formulation according to claim 26, wherein the formulation is stable upon freezing and thawing.

38. An antibody formulation according to claim 26, wherein the formulation comprises water or is reconstituted with water.

39. A pharmaceutical product comprising a vial or syringe comprising an antibody formulation according to claim 26.

40. A pharmaceutical product according to claim 39 further comprising an injection device, which comprises an autoinjector or needle safety device, wherein said device provides for subcutaneous or intramuscular administration of said antibody formulation.

\* \* \* \* \*

SEQUENCE LISTING

```
<160> NUMBER OF SEQ ID NOS: 140

<210> SEQ ID NO 1
<211> LENGTH: 108
<212> TYPE: PRT
<213> ORGANISM: Mus sp.

<400> SEQUENCE: 1

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
                20                  25                  30

Tyr Leu His Trp Tyr Gln Lys Lys Pro Gly Ser Ser Pro Lys Leu Trp
            35                  40                  45

Val Tyr Ser Thr Ser Asn Leu Ala Ser Gly Val Pro Val Arg Phe Ser
        50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln His His Arg Ser Pro
                85                  90                  95

Val Thr Phe Gly Ser Gly Thr Lys Leu Glu Met Lys
            100                 105

<210> SEQ ID NO 2
<211> LENGTH: 107
<212> TYPE: PRT
<213> ORGANISM: Mus sp.

<400> SEQUENCE: 2

Asp Ile Gln Met Thr Gln Ser Pro Ala Ser Gln Ser Ala Ser Leu Gly
1               5                   10                  15
```

```
Glu Ser Val Thr Phe Thr Cys Leu Ala Ser Gln Thr Ile Gly Thr Trp
                20                  25                  30

Leu Ala Trp Tyr Gln Gln Arg Pro Gly Lys Ser Pro Gln Leu Leu Ile
        35                  40                  45

Tyr Ala Ala Thr Ser Leu Ala Asp Gly Val Pro Ser Arg Phe Ser Gly
        50                  55                  60

Ser Gly Ser Gly Thr Gln Phe Ser Phe Asn Ile Arg Ser Leu Gln Ala
65                  70                  75                  80

Glu Asp Phe Ala Ser Tyr Tyr Cys Gln Gln Val Tyr Thr Thr Pro Leu
                85                  90                  95

Thr Phe Gly Gly Gly Thr Lys Leu Glu Ile Lys
                100                 105

<210> SEQ ID NO 3
<211> LENGTH: 107
<212> TYPE: PRT
<213> ORGANISM: Mus sp.

<400> SEQUENCE: 3

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
                20                  25                  30

Leu Gly Trp Tyr Gln Gln Lys Pro Gly Lys Ser Pro Gln Leu Leu Ile
        35                  40                  45

Tyr Arg Ser Thr Thr Leu Ala Asp Gly Val Pro Ser Arg Phe Ser Gly
        50                  55                  60

Ser Gly Ser Gly Thr Lys Phe Ser Phe Lys Ile Ser Ser Leu Gln Ala
65                  70                  75                  80

Ala Asp Phe Ala Ser Tyr Tyr Cys Gln Gln Leu Tyr Ser Ala Pro Tyr
                85                  90                  95

Thr Phe Gly Gly Gly Thr Lys Leu Glu Ile Arg
                100                 105

<210> SEQ ID NO 4
<211> LENGTH: 112
<212> TYPE: PRT
<213> ORGANISM: Mus sp.

<400> SEQUENCE: 4

Asp Val Leu Leu Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
                20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ala Gly Thr Lys Leu Glu Leu Lys
                100                 105                 110

<210> SEQ ID NO 5
<211> LENGTH: 107
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Tyr Lys Tyr
            20                  25                  30

Leu Asn Trp Tyr Gln Gln Lys Pro Asp Gly Thr Leu Lys Leu Leu Ile
        35                  40                  45

Tyr Tyr Thr Ser Gly Leu His Ser Gly Val Pro Ser Arg Phe Ser Gly
    50                  55                  60

Ser Gly Ser Gly Thr Asp Phe Ser Leu Thr Ile Ser Asn Leu Glu Pro
65                  70                  75                  80

Glu Asp Ile Ala Thr Tyr Phe Cys Gln Gln Asp Ser Lys Phe Pro Trp
                85                  90                  95

Thr Phe Gly Gly Asp Thr Lys Leu Glu Ile Lys
            100                 105

<210> SEQ ID NO 6
<211> LENGTH: 108
<212> TYPE: PRT
<213> ORGANISM: Mus sp.

<400> SEQUENCE: 6

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Phe His Trp Tyr Gln Gln Lys Pro Gly Ser Ser Pro Lys Leu Trp
        35                  40                  45

Ile Tyr Arg Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Phe His Arg Ser Pro
                85                  90                  95

Leu Thr Phe Gly Ala Gly Thr Lys Leu Glu Leu Lys
            100                 105

<210> SEQ ID NO 7
<211> LENGTH: 107
<212> TYPE: PRT
<213> ORGANISM: Mus sp.

<400> SEQUENCE: 7

Asp Ile Val Met Thr Gln Ser Gln Lys Phe Leu Ser Thr Ser Val Gly
1               5                   10                  15

Val Arg Val Ser Val Thr Cys Lys Ala Ser Gln Asp Val Gly Thr Asn
            20                  25                  30

Val Leu Trp Tyr Gln Gln Lys Ile Gly Gln Ser Pro Lys Pro Leu Ile
        35                  40                  45

Tyr Ser Ala Ser Tyr Arg His Ser Gly Val Pro Asp Arg Phe Thr Gly
    50                  55                  60

Ser Gly Ser Gly Thr Asp Phe Thr Leu Ile Ile Ser Asn Val Gln Ser
```

```
                65                  70                  75                  80
Glu Asp Leu Ala Glu Tyr Phe Cys Gln Gln Tyr Ser Arg Tyr Pro Leu
                    85                  90                  95

Thr Phe Gly Pro Gly Thr Lys Leu Glu Leu Lys
            100                 105

<210> SEQ ID NO 8
<211> LENGTH: 107
<212> TYPE: PRT
<213> ORGANISM: Mus sp.

<400> SEQUENCE: 8

Asp Ile Val Met Thr Gln Ser Gln Lys Phe Leu Ser Thr Ser Val Gly
1               5                   10                  15

Val Arg Val Ser Val Thr Cys Lys Ala Ser Gln Asp Val Gly Thr Asn
                20                  25                  30

Val Leu Trp Tyr Gln Gln Lys Ile Gly Gln Ser Pro Lys Ala Leu Ile
            35                  40                  45

Tyr Ser Ala Ser Tyr Arg His Ser Gly Val Pro Asp Arg Phe Thr Gly
        50                  55                  60

Ser Gly Ser Gly Thr Asp Phe Thr Leu Ile Ile Thr Asn Val Gln Ser
65                  70                  75                  80

Glu Asp Leu Ala Glu Tyr Phe Cys Gln Gln Tyr Ser Arg Tyr Pro Leu
                    85                  90                  95

Thr Phe Gly Pro Gly Thr Lys Leu Glu Leu Lys
            100                 105

<210> SEQ ID NO 9
<211> LENGTH: 107
<212> TYPE: PRT
<213> ORGANISM: Mus sp.

<400> SEQUENCE: 9

Asp Ile Val Met Thr Gln Ser Gln Lys Phe Met Ser Ala Thr Val Gly
1               5                   10                  15

Gly Arg Val Asn Ile Thr Cys Lys Ala Ser Gln Asn Val Gly Arg Ala
                20                  25                  30

Val Ala Trp Tyr Gln Gln Lys Pro Gly Gln Ser Pro Lys Leu Leu Thr
            35                  40                  45

His Ser Ala Ser Asn Arg Tyr Thr Gly Val Pro Asp Arg Phe Thr Gly
        50                  55                  60

Ser Gly Ser Gly Thr Asp Phe Thr Leu Thr Ile Thr Asn Met Gln Ser
65                  70                  75                  80

Glu Asp Leu Ala Asp Tyr Phe Cys Gln Gln Tyr Ser Ser Tyr Pro Leu
                    85                  90                  95

Thr Phe Gly Ala Gly Thr Lys Leu Asp Leu Lys
            100                 105

<210> SEQ ID NO 10
<211> LENGTH: 107
<212> TYPE: PRT
<213> ORGANISM: Mus sp.

<400> SEQUENCE: 10

Asp Ile Gln Met Thr Gln Ser Pro Ala Ser Gln Ser Ala Ser Leu Gly
1               5                   10                  15

Glu Ser Val Thr Phe Ser Cys Leu Ala Ser Gln Thr Ile Gly Thr Trp
                20                  25                  30
```

-continued

Leu Gly Trp Tyr Gln Gln Lys Pro Gly Lys Ser Pro Gln Leu Leu Ile
            35                  40                  45

Tyr Arg Ala Thr Ser Leu Ala Asp Gly Val Pro Ser Arg Phe Ser Gly
        50                  55                  60

Ser Gly Ser Gly Thr Asn Phe Ser Phe Lys Ile Ser Ser Leu Gln Ala
65                  70                  75                  80

Glu Asp Leu Ala Ser Tyr Tyr Cys Gln Gln Leu Tyr Ser Gly Pro Tyr
                85                  90                  95

Thr Phe Gly Gly Gly Thr Lys Leu Glu Ile Arg
            100                 105

<210> SEQ ID NO 11
<211> LENGTH: 119
<212> TYPE: PRT
<213> ORGANISM: Mus sp.

<400> SEQUENCE: 11

Gln Val Gln Leu Gln Gln Ser Gly Thr Glu Leu Leu Lys Pro Gly Ala
1               5                   10                  15

Ser Val Lys Leu Ser Cys Lys Ala Ser Gly Asn Thr Val Thr Ser Tyr
            20                  25                  30

Trp Met His Trp Val Lys Gln Arg Pro Gly Gln Gly Leu Glu Trp Ile
        35                  40                  45

Gly Glu Ile Leu Pro Ser Thr Gly Arg Thr Asn Tyr Asn Glu Asn Phe
    50                  55                  60

Lys Gly Lys Ala Met Leu Thr Val Asp Lys Ser Ser Thr Ala Tyr
65                  70                  75                  80

Met Gln Leu Ser Ser Leu Ala Ser Glu Asp Ser Ala Val Tyr Tyr Cys
                85                  90                  95

Thr Ile Val Tyr Phe Gly Asn Pro Trp Phe Ala Tyr Trp Gly Gln Gly
            100                 105                 110

Thr Leu Val Thr Val Ser Ala
        115

<210> SEQ ID NO 12
<211> LENGTH: 125
<212> TYPE: PRT
<213> ORGANISM: Mus sp.

<400> SEQUENCE: 12

Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Asp Asn
            20                  25                  30

Tyr Met Asn Trp Val Arg Gln Ser His Gly Lys Ser Leu Glu Trp Ile
        35                  40                  45

Gly Arg Val Asn Pro Ser Asn Gly Asp Thr Lys Tyr Asn Gln Asn Phe
    50                  55                  60

Lys Gly Lys Ala Thr Leu Thr Val Asp Lys Ser Leu Ser Thr Ala Tyr
65                  70                  75                  80

Met Gln Leu Asn Gly Leu Thr Ser Glu Asp Ser Ala Val Tyr Tyr Cys
                85                  90                  95

Gly Arg Thr Lys Asn Phe Tyr Ser Ser Tyr Tyr Asp Asp Ala Met
            100                 105                 110

Asp Tyr Trp Gly Gln Gly Thr Ser Val Thr Val Ser Ser
        115                 120                 125

<210> SEQ ID NO 13
<211> LENGTH: 124
<212> TYPE: PRT
<213> ORGANISM: Mus sp.

<400> SEQUENCE: 13

Glu Val Gln Leu Gln Gln Ser Gly Ala Glu Phe Val Arg Pro Gly Ala
1               5                   10                  15

Ser Val Lys Phe Ser Cys Thr Ala Gly Phe Asn Ile Lys Asp Asp
            20                  25                  30

Tyr Ile His Trp Val Arg Gln Arg Pro Glu Gln Gly Leu Glu Trp Val
            35                  40                  45

Gly Arg Ile Asp Pro Ala Asn Gly Asn Thr Lys Tyr Ala Pro Lys Phe
    50                  55                  60

Gln Asp Lys Ala Thr Ile Thr Ala Asp Thr Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Lys Ser Phe Pro Asn Asn Tyr Tyr Ser Tyr Asp Asp Ala Phe Ala
            100                 105                 110

Tyr Trp Gly Gln Gly Thr Leu Val Thr Val Ser Ala
        115                 120

<210> SEQ ID NO 14
<211> LENGTH: 118
<212> TYPE: PRT
<213> ORGANISM: Mus sp.

<400> SEQUENCE: 14

Gln Val Gln Leu Lys Glu Ser Gly Pro Val Leu Val Ala Pro Ser Gln
1               5                   10                  15

Ser Leu Ser Ile Thr Cys Thr Val Ser Gly Phe Ser Leu Thr Lys Phe
            20                  25                  30

Gly Val His Trp Ile Arg Gln Thr Pro Gly Lys Gly Leu Glu Trp Leu
            35                  40                  45

Gly Val Ile Trp Ala Gly Gly Pro Thr Asn Tyr Asn Ser Ala Leu Met
    50                  55                  60

Ser Arg Leu Thr Ile Ser Lys Asp Ile Ser Gln Ser Gln Val Phe Leu
65                  70                  75                  80

Arg Ile Asp Ser Leu Gln Thr Asp Asp Thr Ala Met Tyr Tyr Cys Ala
                85                  90                  95

Lys Gln Ile Tyr Tyr Ser Thr Leu Val Asp Tyr Trp Gly Gln Gly Thr
            100                 105                 110

Ser Val Thr Val Ser Ser
        115

<210> SEQ ID NO 15
<211> LENGTH: 120
<212> TYPE: PRT
<213> ORGANISM: Mus sp.

<400> SEQUENCE: 15

Gln Val Gln Leu Lys Glu Ser Gly Pro Gly Leu Val Ala Pro Ser Gln
1               5                   10                  15

Ser Leu Phe Ile Thr Cys Thr Val Ser Gly Phe Ser Leu Ser Ser Tyr
            20                  25                  30

```
Glu Ile Asn Trp Val Arg Gln Val Pro Gly Lys Gly Leu Glu Trp Leu
             35                  40                  45

Gly Val Ile Trp Thr Gly Ile Thr Thr Asn Tyr Asn Ser Ala Leu Ile
 50                  55                  60

Ser Arg Leu Ser Ile Ser Lys Asp Asn Ser Lys Ser Leu Val Phe Leu
 65                  70                  75                  80

Lys Met Asn Ser Leu Gln Thr Asp Asp Thr Ala Ile Tyr Tyr Cys Ala
                 85                  90                  95

Arg Gly Thr Gly Thr Gly Phe Tyr Tyr Ala Met Asp Tyr Trp Gly Gln
                100                 105                 110

Gly Thr Ser Val Thr Val Ser Ser
            115                 120

<210> SEQ ID NO 16
<211> LENGTH: 119
<212> TYPE: PRT
<213> ORGANISM: Mus sp.

<400> SEQUENCE: 16

Gln Val Gln Leu Gln Gln Pro Gly Ala Asp Phe Val Arg Pro Gly Ala
  1               5                  10                  15

Ser Met Arg Leu Ser Cys Lys Ala Ser Gly Tyr Ser Phe Thr Ser Ser
                 20                  25                  30

Trp Ile His Trp Val Lys Gln Arg Pro Gly Gln Gly Leu Glu Trp Ile
             35                  40                  45

Gly Glu Ile Asn Pro Gly Asn Val Arg Thr Asn Tyr Asn Glu Asn Phe
 50                  55                  60

Arg Asn Lys Ala Thr Leu Thr Val Asp Lys Ser Ser Thr Thr Ala Tyr
 65                  70                  75                  80

Met Gln Leu Arg Ser Leu Thr Ser Ala Asp Ser Ala Val Tyr Tyr Cys
                 85                  90                  95

Thr Val Val Phe Tyr Gly Glu Pro Tyr Phe Pro Tyr Trp Gly Gln Gly
                100                 105                 110

Thr Leu Val Thr Val Ser Ala
            115

<210> SEQ ID NO 17
<211> LENGTH: 119
<212> TYPE: PRT
<213> ORGANISM: Mus sp.

<400> SEQUENCE: 17

Gln Val Gln Leu Lys Glu Ser Gly Pro Gly Leu Val Ala Pro Ser Gln
  1               5                  10                  15

Ser Leu Ser Ile Thr Cys Thr Val Ser Gly Phe Ser Leu Thr Asn Tyr
                 20                  25                  30

Ala Val His Trp Val Arg Gln Phe Pro Gly Lys Gly Leu Glu Trp Leu
             35                  40                  45

Gly Val Ile Trp Ser Asp Gly Ser Thr Asp Phe Asn Ala Pro Phe Lys
 50                  55                  60

Ser Arg Leu Ser Ile Asn Lys Asp Asn Ser Lys Ser Gln Val Phe Phe
 65                  70                  75                  80

Lys Met Asn Ser Leu Gln Ile Asp Asp Thr Ala Ile Tyr Tyr Cys Ala
                 85                  90                  95

Arg Lys Gly Gly Tyr Ser Gly Ser Trp Phe Ala Tyr Trp Gly Gln Gly
                100                 105                 110
```

Thr Leu Val Thr Val Ser Ala
        115

<210> SEQ ID NO 18
<211> LENGTH: 119
<212> TYPE: PRT
<213> ORGANISM: Mus sp.

<400> SEQUENCE: 18

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Ala Val His Trp Val Arg Gln Phe Pro Gly Lys Gly Leu Glu Trp Leu
        35                  40                  45

Gly Val Ile Trp Ser Asp Gly Ser Thr Asp Tyr Asn Ala Pro Phe Lys
    50                  55                  60

Ser Arg Leu Ser Ile Asn Lys Asp Asn Ser Lys Ser Gln Val Phe Phe
65                  70                  75                  80

Lys Met Asn Ser Leu Gln Thr Asp Asp Thr Ala Ile Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ala
        115

<210> SEQ ID NO 19
<211> LENGTH: 117
<212> TYPE: PRT
<213> ORGANISM: Mus sp.

<400> SEQUENCE: 19

Gln Val Gln Leu Lys Glu Ser Gly Pro Val Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Pro Pro Gly Lys Gly Leu Glu Trp Leu
        35                  40                  45

Gly Val Ile Trp Pro Val Gly Ser Thr Asn Tyr Asn Ser Ala Leu Met
    50                  55                  60

Ser Arg Leu Ser Ile His Lys Asp Asn Ser Lys Ser Gln Val Phe Leu
65                  70                  75                  80

Arg Met Asn Ser Leu Gln Thr Asp Asp Thr Ala Ile Tyr Tyr Cys Ala
                85                  90                  95

Lys Met Asp Trp Asp Asp Phe Phe Asp Tyr Trp Gly Gln Gly Thr Thr
            100                 105                 110

Leu Thr Val Ser Ser
        115

<210> SEQ ID NO 20
<211> LENGTH: 124
<212> TYPE: PRT
<213> ORGANISM: Mus sp.

<400> SEQUENCE: 20

Glu Val Gln Leu Gln Gln Ser Gly Ala Glu Leu Val Arg Pro Gly Ala
1               5                   10                  15

Ser Val Arg Leu Ser Cys Thr Ala Ser Gly Phe Asn Ile Lys Asp Asp

```
                    20                  25                  30
Tyr Ile His Trp Val Arg Gln Arg Pro Lys Gln Gly Leu Glu Trp Leu
        35                  40                  45

Gly Arg Ile Asp Pro Ala Asn Gly Asn Thr Lys Tyr Asp Pro Arg Phe
    50                  55                  60

Gln Asp Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Lys Ser Phe Pro Asp Asn Tyr Tyr Ser Tyr Asp Asp Ala Phe Ala
            100                 105                 110

Tyr Trp Gly Gln Gly Thr Leu Val Thr Val Ser Ala
            115                 120

<210> SEQ ID NO 21
<211> LENGTH: 12
<212> TYPE: PRT
<213> ORGANISM: Mus sp.

<400> SEQUENCE: 21

Thr Ala Ser Ser Ser Val Ser Ser Ser Tyr Leu His
1               5                   10

<210> SEQ ID NO 22
<211> LENGTH: 11
<212> TYPE: PRT
<213> ORGANISM: Mus sp.

<400> SEQUENCE: 22

Leu Ala Ser Gln Thr Ile Gly Thr Trp Leu Ala
1               5                   10

<210> SEQ ID NO 23
<211> LENGTH: 11
<212> TYPE: PRT
<213> ORGANISM: Mus sp.

<400> SEQUENCE: 23

Leu Ala Ser Gln Thr Ile Gly Thr Trp Leu Gly
1               5                   10

<210> SEQ ID NO 24
<211> LENGTH: 16
<212> TYPE: PRT
<213> ORGANISM: Mus sp.

<400> SEQUENCE: 24

Arg Ser Ser Gln Asn Ile Val His Ser Asn Gly Asn Thr Tyr Leu Gln
1               5                   10                  15

<210> SEQ ID NO 25
<211> LENGTH: 11
<212> TYPE: PRT
<213> ORGANISM: Mus sp.

<400> SEQUENCE: 25

Arg Ala Ser Gln Asp Ile Tyr Lys Tyr Leu Asn
1               5                   10

<210> SEQ ID NO 26
<211> LENGTH: 12
<212> TYPE: PRT
```

<213> ORGANISM: Mus sp.

<400> SEQUENCE: 26

Thr Ala Ser Ser Ser Val Ser Ser Ser Tyr Phe His
1               5                   10

<210> SEQ ID NO 27
<211> LENGTH: 11
<212> TYPE: PRT
<213> ORGANISM: Mus sp.

<400> SEQUENCE: 27

Lys Ala Ser Gln Asp Val Gly Thr Asn Val Leu
1               5                   10

<210> SEQ ID NO 28
<211> LENGTH: 11
<212> TYPE: PRT
<213> ORGANISM: Mus sp.

<400> SEQUENCE: 28

Lys Ala Ser Gln Asn Val Gly Arg Ala Val Ala
1               5                   10

<210> SEQ ID NO 29
<211> LENGTH: 11
<212> TYPE: PRT
<213> ORGANISM: Mus sp.

<400> SEQUENCE: 29

Leu Ala Ser Gln Thr Ile Gly Thr Trp Leu Gly
1               5                   10

<210> SEQ ID NO 30
<211> LENGTH: 7
<212> TYPE: PRT
<213> ORGANISM: Mus sp.

<400> SEQUENCE: 30

Ser Thr Ser Asn Leu Ala Ser
1               5

<210> SEQ ID NO 31
<211> LENGTH: 7
<212> TYPE: PRT
<213> ORGANISM: Mus sp.

<400> SEQUENCE: 31

Ala Ala Thr Ser Leu Ala Asp
1               5

<210> SEQ ID NO 32
<211> LENGTH: 7
<212> TYPE: PRT
<213> ORGANISM: Mus sp.

<400> SEQUENCE: 32

Arg Ser Thr Thr Leu Ala Asp
1               5

<210> SEQ ID NO 33
<211> LENGTH: 7
<212> TYPE: PRT
<213> ORGANISM: Mus sp.

```
<400> SEQUENCE: 33

Lys Val Ser Asn Arg Phe Ser
1               5

<210> SEQ ID NO 34
<211> LENGTH: 7
<212> TYPE: PRT
<213> ORGANISM: Mus sp.

<400> SEQUENCE: 34

Tyr Thr Ser Gly Leu His Ser
1               5

<210> SEQ ID NO 35
<211> LENGTH: 7
<212> TYPE: PRT
<213> ORGANISM: Mus sp.

<400> SEQUENCE: 35

Arg Thr Ser Asn Leu Ala Ser
1               5

<210> SEQ ID NO 36
<211> LENGTH: 7
<212> TYPE: PRT
<213> ORGANISM: Mus sp.

<400> SEQUENCE: 36

Ser Ala Ser Tyr Arg His Ser
1               5

<210> SEQ ID NO 37
<211> LENGTH: 7
<212> TYPE: PRT
<213> ORGANISM: Mus sp.

<400> SEQUENCE: 37

Ser Ala Ser Asn Arg Tyr Thr
1               5

<210> SEQ ID NO 38
<211> LENGTH: 7
<212> TYPE: PRT
<213> ORGANISM: Mus sp.

<400> SEQUENCE: 38

Arg Ala Thr Ser Leu Ala Asp
1               5

<210> SEQ ID NO 39
<211> LENGTH: 9
<212> TYPE: PRT
<213> ORGANISM: Mus sp.

<400> SEQUENCE: 39

His Gln His His Arg Ser Pro Val Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 40

Gln Gln Val Tyr Thr Thr Pro Leu Thr
1               5

<210> SEQ ID NO 41
<211> LENGTH: 9
<212> TYPE: PRT
<213> ORGANISM: Mus sp.

<400> SEQUENCE: 41

Gln Gln Leu Tyr Ser Ala Pro Tyr Thr
1               5

<210> SEQ ID NO 42
<211> LENGTH: 9
<212> TYPE: PRT
<213> ORGANISM: Mus sp.

<400> SEQUENCE: 42

Phe Gln Gly Ser His Val Pro Phe Thr
1               5

<210> SEQ ID NO 43
<211> LENGTH: 9
<212> TYPE: PRT
<213> ORGANISM: Mus sp.

<400> SEQUENCE: 43

Gln Gln Asp Ser Lys Phe Pro Trp Thr
1               5

<210> SEQ ID NO 44
<211> LENGTH: 9
<212> TYPE: PRT
<213> ORGANISM: Mus sp.

<400> SEQUENCE: 44

His Gln Phe His Arg Ser Pro Leu Thr
1               5

<210> SEQ ID NO 45
<211> LENGTH: 9
<212> TYPE: PRT
<213> ORGANISM: Mus sp.

<400> SEQUENCE: 45

Gln Gln Tyr Ser Arg Tyr Pro Leu Thr
1               5

<210> SEQ ID NO 46
<211> LENGTH: 9
<212> TYPE: PRT
<213> ORGANISM: Mus sp.

<400> SEQUENCE: 46

Gln Gln Tyr Ser Ser Tyr Pro Leu Thr
1               5

<210> SEQ ID NO 47
<211> LENGTH: 9
<212> TYPE: PRT
<213> ORGANISM: Mus sp.

<400> SEQUENCE: 47

Gln Gln Leu Tyr Ser Gly Pro Tyr Thr
1               5

<210> SEQ ID NO 48
<211> LENGTH: 10
<212> TYPE: PRT
<213> ORGANISM: Mus sp.

<400> SEQUENCE: 48

Gly Asn Thr Val Thr Ser Tyr Trp Met His
1               5                   10

<210> SEQ ID NO 49
<211> LENGTH: 10
<212> TYPE: PRT
<213> ORGANISM: Mus sp.

<400> SEQUENCE: 49

Gly Tyr Thr Phe Thr Asp Asn Tyr Met Asn
1               5                   10

<210> SEQ ID NO 50
<211> LENGTH: 10
<212> TYPE: PRT
<213> ORGANISM: Mus sp.

<400> SEQUENCE: 50

Gly Phe Asn Ile Lys Asp Asp Tyr Ile His
1               5                   10

<210> SEQ ID NO 51
<211> LENGTH: 10
<212> TYPE: PRT
<213> ORGANISM: Mus sp.

<400> SEQUENCE: 51

Gly Phe Ser Leu Thr Lys Phe Gly Val His
1               5                   10

<210> SEQ ID NO 52
<211> LENGTH: 10
<212> TYPE: PRT
<213> ORGANISM: Mus sp.

<400> SEQUENCE: 52

Gly Phe Ser Leu Ser Ser Tyr Glu Ile Asn
1               5                   10

<210> SEQ ID NO 53
<211> LENGTH: 10
<212> TYPE: PRT
<213> ORGANISM: Mus sp.

<400> SEQUENCE: 53

Gly Tyr Ser Phe Thr Ser Ser Trp Ile His
1               5                   10

<210> SEQ ID NO 54
<211> LENGTH: 10
<212> TYPE: PRT
<213> ORGANISM: Mus sp.

<400> SEQUENCE: 54

Gly Phe Ser Leu Thr Asn Tyr Ala Val His

```
1               5                    10
```

<210> SEQ ID NO 55
<211> LENGTH: 10
<212> TYPE: PRT
<213> ORGANISM: Mus sp.

<400> SEQUENCE: 55

```
Gly Phe Ser Leu Thr Asn Tyr Gly Val His
1               5                    10
```

<210> SEQ ID NO 56
<211> LENGTH: 10
<212> TYPE: PRT
<213> ORGANISM: Mus sp.

<400> SEQUENCE: 56

```
Gly Phe Asn Ile Lys Asp Asp Tyr Ile His
1               5                    10
```

<210> SEQ ID NO 57
<211> LENGTH: 17
<212> TYPE: PRT
<213> ORGANISM: Mus sp.

<400> SEQUENCE: 57

```
Glu Ile Leu Pro Ser Thr Gly Arg Thr Asn Tyr Asn Glu Asn Phe Lys
1               5                   10                  15

Gly
```

<210> SEQ ID NO 58
<211> LENGTH: 17
<212> TYPE: PRT
<213> ORGANISM: Mus sp.

<400> SEQUENCE: 58

```
Arg Val Asn Pro Ser Asn Gly Asp Thr Lys Tyr Asn Gln Asn Phe Lys
1               5                   10                  15

Gly
```

<210> SEQ ID NO 59
<211> LENGTH: 17
<212> TYPE: PRT
<213> ORGANISM: Mus sp.

<400> SEQUENCE: 59

```
Arg Ile Asp Pro Ala Asn Gly Asn Thr Lys Tyr Ala Pro Lys Phe Gln
1               5                   10                  15

Asp
```

<210> SEQ ID NO 60
<211> LENGTH: 16
<212> TYPE: PRT
<213> ORGANISM: Mus sp.

<400> SEQUENCE: 60

```
Val Ile Trp Ala Gly Gly Pro Thr Asn Tyr Asn Ser Ala Leu Met Ser
1               5                   10                  15
```

<210> SEQ ID NO 61
<211> LENGTH: 16
<212> TYPE: PRT
<213> ORGANISM: Mus sp.

<400> SEQUENCE: 61

Val Ile Trp Thr Gly Ile Thr Thr Asn Tyr Asn Ser Ala Leu Ile Ser
1               5                   10                  15

<210> SEQ ID NO 62
<211> LENGTH: 15
<212> TYPE: PRT
<213> ORGANISM: Mus sp.

<400> SEQUENCE: 62

Glu Ile Asn Pro Gly Asn Val Arg Thr Asn Tyr Asn Glu Asn Phe
1               5                   10                  15

<210> SEQ ID NO 63
<211> LENGTH: 16
<212> TYPE: PRT
<213> ORGANISM: Mus sp.

<400> SEQUENCE: 63

Val Ile Trp Ser Asp Gly Ser Thr Asp Phe Asn Ala Pro Phe Lys Ser
1               5                   10                  15

<210> SEQ ID NO 64
<211> LENGTH: 16
<212> TYPE: PRT
<213> ORGANISM: Mus sp.

<400> SEQUENCE: 64

Val Ile Trp Ser Asp Gly Ser Thr Asp Tyr Asn Ala Pro Phe Lys Ser
1               5                   10                  15

<210> SEQ ID NO 65
<211> LENGTH: 16
<212> TYPE: PRT
<213> ORGANISM: Mus sp.

<400> SEQUENCE: 65

Val Ile Trp Pro Val Gly Ser Thr Asn Tyr Asn Ser Ala Leu Met Ser
1               5                   10                  15

<210> SEQ ID NO 66
<211> LENGTH: 17
<212> TYPE: PRT
<213> ORGANISM: Mus sp.

<400> SEQUENCE: 66

Arg Ile Asp Pro Ala Asn Gly Asn Thr Lys Tyr Asp Pro Arg Phe Gln
1               5                   10                  15

Asp

<210> SEQ ID NO 67
<211> LENGTH: 10
<212> TYPE: PRT
<213> ORGANISM: Mus sp.

<400> SEQUENCE: 67

Val Tyr Phe Gly Asn Pro Trp Phe Ala Tyr
1               5                   10

<210> SEQ ID NO 68
<211> LENGTH: 16
<212> TYPE: PRT
<213> ORGANISM: Mus sp.

<400> SEQUENCE: 68

Thr Lys Asn Phe Tyr Ser Ser Tyr Asp Asp Ala Met Asp Tyr
1               5                   10                  15

<210> SEQ ID NO 69
<211> LENGTH: 15
<212> TYPE: PRT
<213> ORGANISM: Mus sp.

<400> SEQUENCE: 69

Ser Phe Pro Asn Asn Tyr Tyr Ser Tyr Asp Asp Ala Phe Ala Tyr
1               5                   10                  15

<210> SEQ ID NO 70
<211> LENGTH: 10
<212> TYPE: PRT
<213> ORGANISM: Mus sp.

<400> SEQUENCE: 70

Gln Ile Tyr Tyr Ser Thr Leu Val Asp Tyr
1               5                   10

<210> SEQ ID NO 71
<211> LENGTH: 12
<212> TYPE: PRT
<213> ORGANISM: Mus sp.

<400> SEQUENCE: 71

Gly Thr Gly Thr Gly Phe Tyr Tyr Ala Met Asp Tyr
1               5                   10

<210> SEQ ID NO 72
<211> LENGTH: 10
<212> TYPE: PRT
<213> ORGANISM: Mus sp.

<400> SEQUENCE: 72

Val Phe Tyr Gly Glu Pro Tyr Phe Pro Tyr
1               5                   10

<210> SEQ ID NO 73
<211> LENGTH: 11
<212> TYPE: PRT
<213> ORGANISM: Mus sp.

<400> SEQUENCE: 73

Lys Gly Gly Tyr Ser Gly Ser Trp Phe Ala Tyr
1               5                   10

<210> SEQ ID NO 74
<211> LENGTH: 9
<212> TYPE: PRT
<213> ORGANISM: Mus sp.

<400> SEQUENCE: 74

Met Asp Trp Asp Asp Phe Phe Asp Tyr
1               5

<210> SEQ ID NO 75
<211> LENGTH: 15
<212> TYPE: PRT
<213> ORGANISM: Mus sp.

<400> SEQUENCE: 75

```
Ser Phe Pro Asp Asn Tyr Tyr Ser Tyr Asp Asp Ala Phe Ala Tyr
1               5                   10                  15
```

<210> SEQ ID NO 76
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

```
Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
                20                  25                  30

Tyr Phe His Trp Tyr Gln Gln Lys Pro Gly Gln Ala Pro Arg Leu Leu
            35                  40                  45

Ile Tyr Arg Thr Ser Thr Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys
            100                 105
```

<210> SEQ ID NO 77
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
                20                  25                  30

Tyr Phe His Trp Tyr Gln Gln Lys Pro Gly Gln Ala Pro Arg Leu Leu
            35                  40                  45

Ile Tyr Arg Thr Ser Ile Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys His Gln Phe His Arg Ser Pro
                85                  90                  95

Leu Thr Phe Gly Gln Gly Thr Lys Leu Glu Ile Lys
            100                 105
```

<210> SEQ ID NO 78
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Val Ser Ser Ser
            20                  25                  30

Tyr Phe His Trp Tyr Gln Gln Lys Pro Gly Gln Ala Pro Arg Leu Trp
            35                  40                  45

Ile Tyr Arg Thr Ser Arg Leu Ala Ser Gly Val Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
            85                  90                  95

Leu Thr Phe Gly Gln Gly Thr Lys Leu Glu Ile Lys
            100                 105
```

<210> SEQ ID NO 79
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

```
Glu Ile Val Leu Thr Gln Ser Pro Gly Thr Leu Ser Leu Ser Pro Gly
1               5                   10                  15

Glu Arg Ala Thr Met Thr Cys Thr Ala Ser Ser Val Ser Ser Ser
            20                  25                  30

Tyr Phe His Trp Tyr Gln Gln Lys Pro Gly Gln Ala Pro Arg Leu Leu
            35                  40                  45

Ile Tyr Arg Thr Ser Arg Leu Ala Ser Gly Val Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Phe His Arg Ser Pro
            85                  90                  95

Leu Thr Phe Gly Gln Gly Thr Lys Leu Glu Ile Lys
            100                 105
```

<210> SEQ ID NO 80
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Val Ser Ser Ser
            20                  25                  30

Tyr Phe His Trp Tyr Gln Gln Lys Pro Gly Gln Ala Pro Arg Leu Trp
            35                  40                  45

Ile Tyr Arg Thr Ser Arg Leu Ala Ser Gly Val Pro Asp Arg Phe Ser
        50                  55                  60

Gly Ser Gly Ser Gly Thr Asp Phe Thr Leu Thr Ile Ser Arg Leu Glu
65                  70                  75                  80
```

```
Pro Glu Asp Ala Ala Thr Tyr Tyr Cys His Gln Phe His Arg Ser Pro
                85                  90                  95

Leu Thr Phe Gly Ala Gly Thr Lys Leu Glu Ile Lys
            100                 105
```

<210> SEQ ID NO 81
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Gln Ile Val Leu Thr Gln Ser Pro Gly Thr Leu Ser Leu Ser Pro Gly
1               5                   10                  15

Glu Arg Val Thr Met Ser Cys Thr Ala Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Gln Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys
            100                 105
```

<210> SEQ ID NO 82
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Lys Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys His Gln Phe His Arg Ser Pro
                85                  90                  95

Leu Thr Phe Gly Gln Gly Thr Lys Leu Glu Ile Lys
            100                 105
```

<210> SEQ ID NO 83
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 83

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Val Ser Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser His Leu Ala Ser Gly Ile Pro Gly Arg Phe Ser
50                  55                  60

Gly Ser Gly Ser Gly Thr Asp Phe Thr Leu Thr Ile Ser Arg Leu Glu
65                  70                  75                  80

Pro Glu Asp Ala Ala Val Tyr Tyr Cys His Gln Phe His Arg Ser Pro
                85                  90                  95

Leu Thr Phe Gly Gln Gly Thr Lys Leu Glu Ile Lys
            100                 105

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Glu Tyr Phe Cys Gln Gln Tyr Ser Arg Tyr Pro Leu
                85                  90                  95

Thr Phe Gly Gln Gly Thr Lys Leu Glu Ile Lys
            100                 105

<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
50                  55                  60

Ser Gly Ser Gly Thr Glu Phe Thr Leu Thr Ile Ser Ser Leu Gln Ser

```
                65                  70                  75                  80
Glu Asp Phe Ala Val Tyr Tyr Cys Gln Gln Tyr Ser Arg Tyr Pro Leu
                    85                  90                  95

Thr Phe Gly Gln Gly Thr Lys Leu Glu Ile Lys
                100                 105
```

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
                20                  25                  30

Val Leu Trp Tyr Gln Gln Lys Pro Gly Gln Ala Pro Arg Pro Leu Ile
                35                  40                  45

Tyr Ser Ala Ser Tyr Arg His Ser Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Glu Tyr Tyr Cys Gln Gln Tyr Ser Arg Tyr Pro Leu
                85                  90                  95

Thr Phe Gly Gln Gly Thr Lys Leu Glu Ile Lys
                100                 105
```

<210> SEQ ID NO 87
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Arg Gln Ala Pro Gly Gln Gly Leu Glu Trp Ile
                35                  40                  45

Gly Glu Ile Asn Pro Gly Asn Val Arg Thr Asn Tyr Asn Glu Asn Phe
50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
                100                 105                 110

Thr Leu Val Thr Val Ser Ser
            115
```

<210> SEQ ID NO 88
<211> LENGTH: 119
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Ile
        35                  40                  45

Gly Glu Ile Asn Pro Gly Asn Val Arg Thr Asn Tyr Asn Glu Asn Phe
    50                  55                  60

Arg Asn Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 89
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Lys Gln Ala Pro Gly Gln Gly Leu Glu Trp Met
        35                  40                  45

Gly Glu Ile Asn Pro Gly Asn Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 90
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Met
        35                  40                  45

Gly Glu Ile Asn Pro Gly Asn Val Arg Thr Asn Tyr Asn Glu Asn Phe
    50                  55                  60

Arg Asn Arg Ala Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 91
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Met
        35                  40                  45

Gly Glu Ile Leu Pro Gly Val Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 92
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Ile
        35                  40                  45

Gly Glu Ile Asn Pro Gly Ala Val Arg Thr Asn Tyr Asn Glu Asn Phe
    50                  55                  60

```
Arg Asn Arg Val Thr Met Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Thr Val Val Phe Tyr Gly Glu Pro Tyr Phe Pro Tyr Trp Gly Gln Gly
            100                 105                 110

Thr Leu Val Thr Val Ser Ser
            115

<210> SEQ ID NO 93
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Leu Val Arg Thr Asn Tyr Asn Glu Asn Phe
    50                  55                  60

Arg Asn Lys Val Thr Met Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Val Val Phe Tyr Gly Glu Pro Tyr Phe Pro Tyr Trp Gly Gln Gly
            100                 105                 110

Thr Leu Val Thr Val Ser Ser
            115

<210> SEQ ID NO 94
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Ala Val Arg Thr Asn Tyr Asn Glu Asn Phe
    50                  55                  60

Arg Asn Lys Val Thr Met Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Val Val Phe Tyr Gly Glu Pro Tyr Phe Pro Tyr Trp Gly Gln Gly
            100                 105                 110
```

```
Thr Leu Val Thr Val Ser Ser
        115

<210> SEQ ID NO 95
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Ser Val Arg Thr Asn Tyr Asn Glu Asn Phe
    50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 96
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Asn Lys Asp Thr Ser Lys Ser Gln Val Ser Phe
65                  70                  75                  80

Lys Met Ser Ser Val Gln Ala Ala Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115

<210> SEQ ID NO 97
<211> LENGTH: 119
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 97

```
Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Thr Ser Lys Asn Gln Val Ser Leu
65                  70                  75                  80

Lys Met Asn Ser Leu Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115
```

<210> SEQ ID NO 98
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Asn Ser Lys Ser Gln Val Ser Leu
65                  70                  75                  80

Lys Met Asn Ser Val Thr Val Ala Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115
```

<210> SEQ ID NO 99
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Gln Val Gln Leu Gln Glu Ser Gly Pro Gly Leu Val Lys Pro Ser Glu
1               5                   10                  15
```

```
Thr Leu Ser Ile Thr Cys Thr Val Ser Gly Phe Ser Leu Thr Asp Tyr
            20                  25                  30

Ala Val His Trp Val Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Thr Ser Lys Asn Gln Val Ser Phe
65                  70                  75                  80

Lys Leu Ser Ser Val Thr Val Asp Asp Thr Ala Val Tyr Tyr Cys Ala
                85                  90                  95

Arg Lys Gly Gly Tyr Ser Gly Ser Trp Phe Ala Tyr Trp Gly Gln Gly
                100                 105                 110

Thr Leu Val Thr Val Ser Ser
            115

<210> SEQ ID NO 100
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Val Gln Leu Gln Glu Ser Gly Pro Gly Leu Val Ala Pro Ser Glu
1               5                   10                  15

Thr Leu Ser Leu Thr Cys Thr Val Ser Gly Phe Ser Leu Thr Asp Tyr
            20                  25                  30

Ala Val His Trp Ile Arg Gln Phe Pro Gly Lys Gly Leu Glu Trp Ile
        35                  40                  45

Gly Val Ile Trp Ser Asp Gly Ser Thr Asp Phe Asn Ala Pro Phe Lys
    50                  55                  60

Ser Arg Val Thr Ile Ser Lys Asp Thr Ser Lys Asn Gln Val Ser Phe
65                  70                  75                  80

Lys Leu Ser Ser Val Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
                100                 105                 110

Thr Leu Val Thr Val Ser Ser
            115

<210> SEQ ID NO 101
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60
```

```
Ser Arg Val Thr Ile Ser Lys Asp Asn Ser Lys Ser Gln Val Ser Phe
 65                  70                  75                  80

Lys Met Ser Ser Val Thr Ala Asp Asp Thr Ala Val Tyr Tyr Cys Ala
                 85                  90                  95

Arg Lys Gly Gly Tyr Ser Gly Ser Trp Phe Ala Tyr Trp Gly Gln Gly
            100                 105                 110

Thr Leu Val Thr Val Ser Ser
            115

<210> SEQ ID NO 102
<211> LENGTH: 7
<212> TYPE: PRT
<213> ORGANISM: Mus sp.

<400> SEQUENCE: 102

Arg Thr Ser Thr Leu Ala Ser
 1               5

<210> SEQ ID NO 103
<211> LENGTH: 7
<212> TYPE: PRT
<213> ORGANISM: Mus sp.

<400> SEQUENCE: 103

Arg Thr Ser Ile Leu Ala Ser
 1               5

<210> SEQ ID NO 104
<211> LENGTH: 7
<212> TYPE: PRT
<213> ORGANISM: Mus sp.

<400> SEQUENCE: 104

Arg Thr Ser Arg Leu Ala Ser
 1               5

<210> SEQ ID NO 105
<211> LENGTH: 7
<212> TYPE: PRT
<213> ORGANISM: Mus sp.

<400> SEQUENCE: 105

Arg Thr Ser Gln Leu Ala Ser
 1               5

<210> SEQ ID NO 106
<211> LENGTH: 7
<212> TYPE: PRT
<213> ORGANISM: Mus sp.

<400> SEQUENCE: 106

Arg Thr Ser Lys Leu Ala Ser
 1               5

<210> SEQ ID NO 107
<211> LENGTH: 10
<212> TYPE: PRT
<213> ORGANISM: Mus sp.

<400> SEQUENCE: 107

Gly Phe Ser Leu Thr Asp Tyr Ala Val His
 1               5                  10
```

<210> SEQ ID NO 108
<211> LENGTH: 15
<212> TYPE: PRT
<213> ORGANISM: Mus sp.

<400> SEQUENCE: 108

Glu Ile Leu Pro Gly Val Val Arg Thr Asn Tyr Asn Glu Asn Phe
1               5                   10                  15

<210> SEQ ID NO 109
<211> LENGTH: 15
<212> TYPE: PRT
<213> ORGANISM: Mus sp.

<400> SEQUENCE: 109

Glu Ile Asn Pro Gly Ala Val Arg Thr Asn Tyr Asn Glu Asn Phe
1               5                   10                  15

<210> SEQ ID NO 110
<211> LENGTH: 15
<212> TYPE: PRT
<213> ORGANISM: Mus sp.

<400> SEQUENCE: 110

Glu Ile Asn Pro Gly Leu Val Arg Thr Asn Tyr Asn Glu Asn Phe
1               5                   10                  15

<210> SEQ ID NO 111
<211> LENGTH: 15
<212> TYPE: PRT
<213> ORGANISM: Mus sp.

<400> SEQUENCE: 111

Glu Ile Asn Pro Gly Ser Val Arg Thr Asn Tyr Asn Glu Asn Phe
1               5                   10                  15

<210> SEQ ID NO 112
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 113
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 114
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 114

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Thr Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 115
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Ile Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 116
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Trp
        35                  40                  45

Ile Tyr Arg Thr Ser Arg Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 117
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Arg Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 118
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
            20                  25                  30

Tyr Phe His Trp Tyr Gln Gln Lys Pro Gly Gln Ala Pro Arg Leu Trp
        35                  40                  45

Ile Tyr Arg Thr Ser Arg Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Ala Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

```
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 119
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Ile Val Leu Thr Gln Ser Pro Gly Thr Leu Ser Leu Ser Pro Gly
1               5                   10                  15

Glu Arg Val Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Gln Leu Ala Ser Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 120
<211> LENGTH: 215
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 120

```
Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Val Ser Ser Ser
            20                  25                  30

Tyr Phe His Trp Tyr Gln Gln Lys Pro Gly Gln Ala Pro Arg Leu Leu
            35                  40                  45

Ile Tyr Arg Thr Ser Lys Leu Ala Ser Gly Val Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215
```

<210> SEQ ID NO 121
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
            35                  40                  45

Ile Tyr Arg Thr Ser His Leu Ala Ser Gly Ile Pro Gly Arg Phe Ser
50                  55                  60

Gly Ser Gly Ser Gly Thr Asp Phe Thr Leu Thr Ile Ser Arg Leu Glu
65                  70                  75                  80

Pro Glu Asp Ala Ala Val Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
```

```
                 115                 120                 125
Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
                195                 200                 205

Ser Phe Asn Arg Gly Glu Cys
            210                 215

<210> SEQ ID NO 122
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Glu Tyr Phe Cys Gln Gln Tyr Ser Arg Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 123
<211> LENGTH: 214
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 123

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Arg Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 124
<211> LENGTH: 214
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 124

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Glu Tyr Tyr Cys Gln Gln Tyr Ser Arg Tyr Pro Leu
                85                  90                  95

Thr Phe Gly Gln Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 125
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Asn Val Arg Thr Asn Tyr Asn Glu Asn Phe
    50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255
```

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 126
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Ile
        35                  40                  45

Gly Glu Ile Asn Pro Gly Asn Val Arg Thr Asn Tyr Asn Glu Asn Phe
    50                  55                  60

Arg Asn Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 127
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Lys Gln Ala Pro Gly Gln Gly Leu Glu Trp Met
        35                  40                  45

Gly Glu Ile Asn Pro Gly Asn Val Arg Thr Asn Tyr Asn Glu Asn Phe
    50                  55                  60
```

```
Arg Asn Lys Val Thr Met Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Thr Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 128
<211> LENGTH: 449
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Met
        35                  40                  45

Gly Glu Ile Asn Pro Gly Asn Val Arg Thr Asn Tyr Asn Glu Asn Phe
    50                  55                  60

Arg Asn Arg Ala Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 129
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Met
        35                  40                  45

Gly Glu Ile Leu Pro Gly Val Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys

<210> SEQ ID NO 130
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Ser Ser
                20                  25                  30
Trp Ile His Trp Val Arg Gln Arg Pro Gly Gln Gly Leu Glu Trp Ile
            35                  40                  45
Gly Glu Ile Asn Pro Gly Ala Val Arg Thr Asn Tyr Asn Glu Asn Phe
50                  55                  60
Arg Asn Arg Val Thr Met Thr Val Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Thr Val Val Phe Tyr Gly Glu Pro Tyr Phe Pro Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190

```
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
            435                 440                 445
Lys

<210> SEQ ID NO 131
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Ser Ser
            20                  25                  30
Trp Ile His Trp Val Arg Gln Ala Pro Gly Gln Gly Leu Glu Trp Ile
        35                  40                  45
Gly Glu Ile Asn Pro Gly Leu Val Arg Thr Asn Tyr Asn Glu Asn Phe
    50                  55                  60
Arg Asn Lys Val Thr Met Thr Val Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
```

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 132
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
            35                  40                  45

Gly Glu Ile Asn Pro Gly Ala Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
                    420                 425                 430
Ala Leu His Asn His Tyr Thr Gln Lys Ser Leu Ser Leu Ser Pro Gly
            435                 440                 445

Lys

<210> SEQ ID NO 133
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Ser Val Arg Thr Asn Tyr Asn Glu Asn Phe
    50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

-continued

```
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
                355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
                435                 440                 445
Lys

<210> SEQ ID NO 134
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Val Gln Leu Gln Glu Ser Gly Pro Gly Leu Val Lys Pro Ser Glu
1               5                   10                  15
Thr Leu Ser Ile Thr Cys Thr Val Ser Gly Phe Ser Leu Thr Asp Tyr
                20                  25                  30
Ala Val His Trp Ile Arg Gln Pro Pro Gly Lys Gly Leu Glu Trp Ile
            35                  40                  45
Gly Val Ile Trp Ser Asp Gly Ser Thr Asp Tyr Asn Ala Pro Phe Lys
        50                  55                  60
Ser Arg Val Thr Ile Asn Lys Asp Thr Ser Lys Ser Gln Val Ser Phe
65                  70                  75                  80
Lys Met Ser Ser Val Gln Ala Ala Asp Thr Ala Val Tyr Tyr Cys Ala
                85                  90                  95
Arg Lys Gly Gly Tyr Ser Gly Ser Trp Phe Ala Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
        210                 215                 220
Thr His Thr Cys Pro Pro Cys Pro Ala Pro Glu Ala Ala Gly Gly Pro
```

```
                225                 230                 235                 240
Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys
```

<210> SEQ ID NO 135
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

```
Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
                20                  25                  30

Ala Val His Trp Ile Arg Gln Pro Pro Gly Lys Gly Leu Glu Trp Ile
            35                  40                  45

Gly Val Ile Trp Ser Asp Gly Ser Thr Asp Tyr Asn Ala Pro Phe Lys
        50                  55                  60

Ser Arg Val Thr Ile Ser Lys Asp Thr Ser Lys Asn Gln Val Ser Leu
65                  70                  75                  80

Lys Met Asn Ser Leu Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
```

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 136
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
```

```
                35                  40                  45
Gly Val Ile Trp Ser Asp Gly Ser Thr Asp Tyr Asn Ala Pro Phe Lys
 50                  55                  60

Ser Arg Val Thr Ile Ser Lys Asp Asn Ser Lys Ser Gln Val Ser Leu
 65                  70                  75                  80

Lys Met Asn Ser Val Thr Val Ala Asp Thr Ala Val Tyr Tyr Cys Ala
                 85                  90                  95

Arg Lys Gly Gly Tyr Ser Gly Ser Trp Phe Ala Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 137
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 137

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Val Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Thr Ser Lys Asn Gln Val Ser Phe
65                  70                  75                  80

Lys Leu Ser Ser Val Thr Val Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 138
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Gln Glu Ser Gly Pro Gly Leu Val Ala Pro Ser Glu
1               5                   10                  15

Thr Leu Ser Leu Thr Cys Thr Val Ser Gly Phe Ser Leu Thr Asp Tyr
            20                  25                  30

Ala Val His Trp Ile Arg Gln Phe Pro Gly Lys Gly Leu Glu Trp Ile
        35                  40                  45

Gly Val Ile Trp Ser Asp Gly Ser Thr Asp Phe Asn Ala Pro Phe Lys
    50                  55                  60

Ser Arg Val Thr Ile Ser Lys Asp Thr Ser Lys Asn Gln Val Ser Phe
65                  70                  75                  80

Lys Leu Ser Ser Val Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 139
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Asn Ser Lys Ser Gln Val Ser Phe
65                  70                  75                  80

Lys Met Ser Ser Val Thr Ala Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 140
<211> LENGTH: 7
<212> TYPE: PRT
<213> ORGANISM: Mus sp.

<400> SEQUENCE: 140

Arg Thr Ser His Leu Ala Ser
1               5
```